United States Patent
Zhou et al.

(10) Patent No.: US 9,006,433 B2
(45) Date of Patent: Apr. 14, 2015

(54) SUBSTITUTED PYRIMIDINES

(75) Inventors: Changyou Zhou, Beijing (CN); Wuxin Zou, Beijing (CN); Yuxia Hua, Beijing (CN); Qun Dang, Rahway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 206 days.

(21) Appl. No.: 13/635,275

(22) PCT Filed: Apr. 18, 2011

(86) PCT No.: PCT/US2011/032829
§ 371 (c)(1),
(2), (4) Date: Sep. 14, 2012

(87) PCT Pub. No.: WO2011/133444
PCT Pub. Date: Oct. 27, 2011

(65) Prior Publication Data
US 2013/0018053 A1 Jan. 17, 2013

Related U.S. Application Data

(60) Provisional application No. 61/334,432, filed on May 13, 2010.

(30) Foreign Application Priority Data

Apr. 21, 2010 (WO) ................ PCT/CN2010/071974

(51) Int. Cl.
*A61K 31/506* (2006.01)
*C07D 403/04* (2006.01)
*C07D 401/14* (2006.01)
*C07D 403/14* (2006.01)
*C07D 405/14* (2006.01)

(52) U.S. Cl.
CPC ............ *C07D 403/04* (2013.01); *C07D 401/14* (2013.01); *C07D 403/14* (2013.01); *C07D 405/14* (2013.01)

(58) Field of Classification Search
CPC ........................... A61K 31/506; C07D 403/04
USPC ............. 514/252.02, 273; 544/320, 321, 238
See application file for complete search history.

(56) References Cited

U.S. PATENT DOCUMENTS

2011/0021531 A1 1/2011 Chobanian et al.

FOREIGN PATENT DOCUMENTS

| WO | WO97/03688 | 2/1997 |
|---|---|---|
| WO | WO2004/033652 | 4/2004 |
| WO | WO2011/094209 | 8/2011 |
| WO | WO2011/126960 | 10/2011 |

OTHER PUBLICATIONS

Pil'O, S.G. et al., Synthesis of New 5-Mercapto-1,3-oxazole Derivatives on the Basis of 2-Acylamino-3,3-Dichloroacrylonitriles and Their Analogs, Russian Journal of General Chemistry, Pleiades Publishing Ltd, 2002, pp. 1714-1723, vol. 72, No. 11.
Kreisberg J.D. et al., "Pummerer Reaction Methodology for the Synthesis of 5-Thiophenyl Substituted Oxazoles", Tetrahedron Letters, 2002, pp. 7393-7396, No. 43.
Du, W. et al., "Heterocyclic Sulfonxide and Sulfone Inhibitors of Fatty Acid Amide Hydrolase", Bioorganic & Medicinal Chemistry Letters, 2005, pp. 103-106, No. 15.
Liu, X.H. et al., "Novel 2,4,5-Trisubstituted Oxazole Derivatives: Synthesis and Antiproliferative Activity", European Journal of Medicinal Chemistry, 2009, pp. 3930-3935, No. 44.
International Preliminary Report on Patentability, PCT/US09/52171 (Feb. 8, 2011).

*Primary Examiner* — James O. Wilson
*Assistant Examiner* — Ebenezer O Sackey
(74) *Attorney, Agent, or Firm* — Matthew A. Leff; John C. Todaro

(57) ABSTRACT

The present invention relates to substituted pyrimidines useful as HIF prolyl hydroxylase inhibitors to treat anemia and like conditions.

2 Claims, No Drawings

SUBSTITUTED PYRIMIDINES

CROSS REFERENCE TO RELATED APPLICATIONS

This application is a U.S. National Phase application under 35 U.S.C. §371 of PCT Application No. PCT/US2011/032829, filed Apr. 18, 2011, which claims priority under 35 U.S.C. §119(e) from U.S. Provisional Application Ser. No. 61/334,432, filed May 13, 2010.

This application claims the benefit of International Application. No. PCT/CN2010/071974, filed Apr. 21, 2010, the disclosure of which is incorporated by reference herein in its entirety.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)—, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

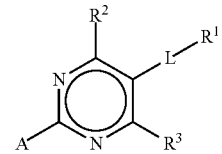

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

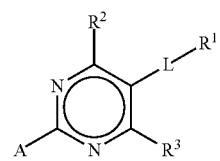

wherein

A is heteroaryl optionally substituted with one or more $R^9$ substituents;

L is chosen from a bond, aryl, heteroaryl, —($C_{1-3}$ alkyl)$_{0-1}$S ($C_{1-3}$ alkyl)$_{0-1}$-, —$C_{1-3}$ alkyl)$_{0-1}$NR$^a$CO—, —($C_{1-3}$ alkyl)$_{0-1}$NR$^a$CO$_2$—, —($C_{1-3}$ alkyl)$_{0-1}$CO$_2$—, —($C_{1-3}$ alkyl)$_{0-1}$NR$^a$SO$_2$—, —($C_{1-3}$ alkyl)$_{0-1}$NR$^a$O—, —($C_{1-3}$ alkyl)$_{0-1}$NR$^{aC}$SNR$^b$—, —($C_{1-3}$ alkyl)$_{0-1}$ NR$^a$CONR$^b$—, and —($C_{1-3}$ alkyl)$_{0-1}$NR$^a$COS—;

$R^2$ and $R^3$ are independently selected from hydrogen, halogen, hydroxyl, $C_{1-6}$ alkyl, $C_{3-6}$ heterocycloalkyl and $C_{3-6}$ cycloalkyl wherein said alkyl, heterocycloalkyl and cycloalkyl are each optionally substituted with one or more substituents selected from: hydroxyl, —SR$^a$, —NR$^a_2$ or —CO$_2$—R$^a$;

R¹ is selected from
halogen,
$C_{1-10}$ alkyl,
—$C2_{-10}$ alkenyl,
—$C_{2-10}$ alkynyl,
cycloalkyl $C_{0-10}$ alkyl(oxy)$_{0-1}$,
heterocyclyl $C_{0-10}$ alkyl(oxy)$_{0-1}$,
aryl$C_{0-10}$ alkyl(oxy)$_{0-1}$,
$C_{1-10}$ alkoxy (carbonyl)$_{0-1}$ $C_{0-10}$alkyl,
carboxyl $C_{0-10}$ alkyl,
carboxyl aryl,
carboxylcycloalkyl,
carboxylheterocyclyl,
$C_{1-10}$alkyloxy $C_{0-10}$alkyl,
hydroxy $C_{0-10}$alkyl,
hydroxycarbonyl$C_{0-10}$alkoxy,
$C_{1-10}$ alkylthio,
$C_{1-10}$ alkylsulfinyl,
aryl $C_{0-10}$ alkylsulfinyl,
heterocyclyl $C_{1-10}$ alkylsulfinyl,
cycloalkyl $C_{0-10}$ alkylsulfinyl,
$C_{1-10}$ alkylsulfonyl,
aryl $C_{0-10}$ alkylsulfonyl,
heterocyclyl$C_{0-10}$ alkylsulfonyl,
cycloalkyl $C_{0-10}$ alkylsulfonyl,
nitro,
perfluoro$C_{1-6}$alkyl, and
perfluoro$C_{1-6}$alkoxy;
wherein in R¹ said alkyl, alkenyl, alkynyl, cycloalkenyl, aryl, perfluoralkyl, perfluoroalkoxy, heterocyclyl, and cycloalkyl are each optionally substituted with one or more R⁹ substituents;
optionally, R¹ and L are linked together to form a ring of 5 to 8 atoms optionally substituted with one or more substituents R⁹; where said ring has 0, 1, or 2 heteroatoms independently selected from —NR$^b$—, —O— and —S(O)$_n$—;
R⁹ is selected from halogen, hydroxy, oxo, cyano, aryl, heterocyclyl, cycloalkyl, —$C_{1-6}$ alkyl, —$C_{1-6}$ alkoxy, aryloxy, heterocyclyloxy, —O$_{(0-1)}$($C_{1-10}$)perfluoroalkyl, —CO$_2$R$^a$, —NR$^b$R$^c$, —CONR$^b$R$^c$, —OCO$_2$R$^a$, —OCONR$^b$R$^c$, —NR$^d$CO$_2$R$^a$, NR$^d$CONR$^b$R$^c$, —SC$_{0-6}$ alkyl and —S(O)$_n$R$^d$, wherein said aryl, heteroaryl, heterocycloalkyl, alkoxy, aryloxy, heteroaryloxy, heterocycloalkyloxy are optionally substituted by one or more substituents R¹⁰;
R¹⁰ is selected from hydroxy, aryl, heterocycloalkyl, heteroaryl, halogen, oxo, —$C_{1-6}$ alkyl, $C_{1-6}$ alkoxy, halogen, CO$_2$H, cyano, O(C=O)$_{0-1}$$C_{1-6}$ alkyl, NO$_2$, trifluoromethoxy, trifluoroethoxy, —O$_{0-1}$)($C_{1-10}$)perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$ alkyl, $C_{0-10}$ alkylaminosulfonylamino$C_{0-10}$ alkyl, $C_{0-10}$ alkylsulthnylamino$C_{0-10}$ alkyl, $C_{0-10}$ alkylsulfonyl, $C_{0-10}$ alkylaminosulfonyl, $C_{0-10}$ alkylaminocarbonyl, —(C=O)N($C_{0-6}$ alkyl)$_2$, —S($C_{0-6}$ alkyl), and NH$_2$;
n is 1 or 2;
R$^a$ is chosen from hydrogen; —$C_{1-10}$ alkyl, —($C_{1-6}$ alkyl)$C_{3-8}$ cycloalkyl; and —($C_{1-6}$ alkyl)phenyl; and
R$^b$, R$^c$, and R$^d$ are each independently chosen from hydrogen, —$C_{1-10}$ alkyl, $C_{3-8}$ cycloalkyl, aryl, and heterocyclyl.

Illustrative but nonlimiting examples of compounds of the invention are the following:

N-(4-hydroxy-2-(1H-pyrazol-1-yl)pyrimidin-5-yl)-2,2-diphenylacetamide;
2-chloro-N-(4-hydroxy-2-(1H-pyrazol-1-yl)pyrimidin-5-yl)benzamide;
3-chloro-N-(4-hydroxy-2-(1H-pyrazol-1-yl)pyrimidin-5-yl)benzamide;
4-chloro-N-(4-hydroxy-2-(1H-pyrazol-1-yl)pyrimidin-5-yl)benzamide;
3-(trifluoromethyl)-N-(4-hydroxy-2-(1H-pyrazol-1-yl)pyrimidin-5-yl)benzamide;
4-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-(naphthalen-3-yl)acetamide;
2-cyano-N-(4-hydroxy-2-(1H-pyrazol-1-yl)pyrimidin-5-yl)benzamide;
3-cyano-N-(4-hydroxy-2-(1H-pyrazol-1-yl)pyrimidin-5-yl)benzamide;
4-cyano-N-(4-hydroxy-2-(1H-pyrazol-1-yl)pyrimidin-5-yl)benzamide;
2-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-methoxybenzamide;
N-(4-hydroxy-2-(1H-pyrazol-1-yl)pyrimidin-5-yl)-3-methoxybenzamide;
N-(4-hydroxy-2-(1H-pyrazol-1-yl)pyrimidin-5-yl)-4-methoxybenzamide;
N-(4-hydroxy-2-(1H-pyrazol-1-yl)pyrimidin-5-yl)-2-(methyl sulfonyl)benzamide;
N-(4-hydroxy-2-(1H-pyrazol-1-yl)pyrimidin-5-yl)-3-(methylsulfonyl)benzamide;
N-(4-hydroxy-2-(1H-pyrazol-1-yl)pyrimidin-5-yl)-4-(methylsulfonyl)benzamide;
N-[4-hydroxy-2-(1H-pyrazol-1-yl)pyrimidin-5-yl]biphenyl-2-carboxamide;
N-[4-hydroxy-2-(1H-pyrazol-1-yl)pyrimidin-5-yl]biphenyl-3-carboxamide;
N-[4-hydroxy-2-(1H-pyrazol-1-yl)pyrimidin-5-yl]biphenyl-4-carboxamide;
N-(4-hydroxy-2-(1H-pyrazol-1-yl)pyrimidin-5-yl)-2-phenoxybenzamide;
N-(4-hydroxy-2-(1H-pyrazol-1-yl)pyrimidin-5-yl)-3-phenoxybenzamide;
N-(4-hydroxy-2-(1H-pyrazol-1-yl)pyrimidin-5-yl)-4-phenoxybenzamide;
2-(2-chlorophenyl)-N-(4-hydroxy-2-(1H-pyrazol-1-yl)pyrimidin-5-yl)acetamide;
2-(3-chlorophenyl)-N-(4-hydroxy-2-(1H-pyrazol-1-yl)pyrimidin-5-yl)acetamide;
2-(4-chlorophenyl)-N-(4-hydroxy-2-(1H-pyrazol-1-yl)pyrimidin-5-yl)acetamide;
2-(3-cyanophenyl)-N-(4-hydroxy-2-(1H-pyrazol-1-yl)pyrimidin-5-yl)acetamide;
2-(2-(trifluoromethyl)phenyl)-N-(4-hydroxy-2-(1H-pyrazol-1-yl)pyrimidin-5-yl)acetamide;
2-(3-(trifluoromethyl)phenyl)-N-(4-hydroxy-2-(1H-pyrazol-1-yl)pyrimidin-5-yl)acetamide;
2-(4-(trifluoromethyl)phenyl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(2-methoxyphenyl)acetamide;
N-(4-hydroxy-2-(1H-pyrazol-1-yl)pyrimidin-5-yl)-2-(3-methoxyphenyl)acetamide;
N-(4-hydroxy-2-(1H-pyrazol-1-yl)pyrimidin-5-yl)-2-(4-methoxyphenyl)acetamide;
N-(4-hydroxy-2-(1H-pyrazol-1-yl)pyrimidin-5-yl)-2-phenylpropanamide;
N-(4-hydroxy-2-(1H-pyrazol-1-yl)pyrimidin-5-yl)-2-phenylbutanamide;
N-(4-hydroxy-2-(1H-pyrazol-1-yl)pyrimidin-5-yl)-3-methyl-2-phenylbutanamide;

N-(4-hydroxy-2-(1H-pyrazol-1-yl)pyrimidin-5-yl)-3-methyl-2-phenylpentanamide;
N-(4-hydroxy-2-(1H-pyrazol-1-yl)pyrimidin-5-yl)-2-methyl-2-phenylpropanamide;
N-(4-hydroxy-2-(1H-pyrazol-1-yl)pyrimidin-5-yl)-1-phenylcyclopropanecarboxamide;
N-(4-hydroxy-2-(1H-pyrazol-1-yl)pyrimidin-5-yl)-2-(naphthalen-1-yl)acetamide;
2-(benzo[d][1,3]dioxol-5-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(pyridin-4-yl)acetamide;
2-(biphenyl-4-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)heptanamide;
N-(4-hydroxy-2-(1H-pyrazol-1-yl)pyrimidin-5-yl)-3-phenylpropanamide;
N-(4-hydroxy-2-(1H-pyrazol-1-yl)pyrimidin-5-yl)-4-phenylbutanamide;
N-(4-hydroxy-2-(1H-pyrazol-1-yl)pyrimidin-5-yl)cyclohexanecarboxamide;
tert-butyl-4-(4-hydroxy-2-(1H-pyrazol-1-yl)pyrimidin-5-ylcarbamoyl)piperidine-1-carboxylate;
2-cyclohexyl-N-(4-hydroxy-2-(1H-pyrazol01.01-1-yl)pyrimidin-5-yl)acetamide;
tert-butyl 3-(4-hydroxy-2-(1H-pyrazol-1-yl)pyrimidin-5-ylcarbamoyl)piperidine-1-carboxylate;
tert-butyl-4-((4-hydroxy-2-(1H-pyrazol-1-yl)pyrimidin-5-ylcarbamoyl)methyl)piperidine-1-carboxylate;
tert-butyl 3-(4-hydroxy-2-(1H-pyrazol-1-yl)pyrimidin-5-ylcarbamoyl)pyrrolidine-1-carboxylate;
1,2,3,4-tetrahydro-N-(4-hydroxy-2-(1H-pyrazol-1-yl)pyrimidin-5-yl)naphthalene-1-carboxamide;
2,3-dihydro-N-(4-hydroxy-2-(1H-pyrazol-1-yl)pyrimidin-5-yl)-1H-indene-1-carboxamide;
1,2,3,4-tetrahydro-N-(4-hydroxy-2-(1H-pyrazol-1-yl)pyrimidin-5-yl)naphthalene-2-carboxamide;
2,3-dihydro-N-(4-hydroxy-2-(1H-pyrazol-1-yl)pyrimidin-5-yl)-1H-indene-2-carboxamide;
4-chloro-N-[4-hydroxy-2-(1H-pyrazol-1-yl)pyrimidin-5-yl]benzenesulfonamide;
1-(4-chlorophenyl)-N-[4-hydroxy-2-(1H-pyrazol-1-yl)pyrimidin-5-yl]methanesulfonamide;
3-chloro-N-[4-hydroxy-2-(1H-pyrazol-1-yl)pyrimidin-5-yl]benzenesulfonamide;
N-[4-hydroxy-2-(1H-pyrazol-1-yl)pyrimidin-5-yl]-1-[4-(trifluoromethyl)phenyl]methanesulfonamide;
1-(4-hydroxy-2-(1H-pyrazol-1-yl)pyrimidin-5-yl)-3-phenylurea;
1-benzyl-3-(4-hydroxy-2-(1H-pyrazol-1-yl)pyrimidin-5-yl)urea;
1-(4-hydroxy-2-(1H-pyrazol-1-yl)pyrimidin-5-yl)-3-(1-phenylethyl)urea;
1-cyclohexyl-3-(4-hydroxy-2-(1H-pyrazol-1-yl)pyrimidin-5-yl)urea;
1-cyclopentyl-3-(4-hydroxy-2-(1H-pyrazol-1-yl)pyrimidin-5-yl)urea;
ert-butyl-3-(4-hydroxy-2-(1H-pyrazol-1-yl)pyrimidin-5-yl)urea;
3-(4-hydroxy-2-(1H-pyrazol-1-yl)pyrimidin-5-yl)-1,1-diphenylurea;
3-(4-hydroxy-2-(1H-pyrazol-1-yl)pyrimidin-5-yl)-1-isopropyl-1-phenylurea;
phenyl 4-hydroxy-2-(1H-pyrazol-1-yl)pyrimidin-5-yl carbamate;
cyclohexyl 4-hydroxy-2-(1H-pyrazol-1-yl)pyrimidin-5-yl carbamate;
cyclopentyl 4-hydroxy-2-(1H-pyrazol-1-yl)pyrimidin-5-yl carbamate;
tert-butyl 4-hydroxy-2-(1H-pyrazol-1-yl)pyrimidin-5-yl carbamate;
butyl 4-hydroxy-2-(1H-pyrazol-1-yl)pyrimidin-5-ylcarbamate;
4-methoxyphenyl 4-hydroxy-2-(1H-pyrazol-1-yl)pyrimidin-5-yl carbamate;
3,3-dimethylbutyl 4-hydroxy-2-(1H-pyrazol-1-yl)pyrimidin-5-ylcarbamate;
phenethyl 4-hydroxy-2-(1H-pyrazol-1-yl)pyrimidin-5-ylcarbamate;
biphenyl-4-yl-4-hydroxy-2-(1H-pyrazol-1-yl)pyrimidin-5-yl carbamate;
naphthalen-2-yl-4-hydroxy-2-(1H-pyrazol-1-yl)pyrimidin-5-yl carbamate;
1-benzhydryl-3-(4-hydroxy-2-(1H-pyrazol-1-yl)pyrimidin-5-yl)thiourea;
1-(4-hydroxy-2-(1H-pyrazol-1-yl)pyrimidin-5-yl)-3-(1-phenylethyl)thiourea;
1-(4-hydroxy-2-(1H-pyrazol-1-yl)pyrimidin-5-yl)-3-(2-phenylpropan-2-yl)thiourea;
benzhydryl 4-hydroxy-2-(1H-pyrazol-1-yl)pyrimidine-5-carboxylate;
N-(4-hydroxy-2-(pyridin-2-yl)pyrimidin-5-yl)-2,2-diphenylacetamide;
5-(1-phenyl-1H-pyrazol-4-yl)-2-(1H-pyrazol-1-yl)pyrimidin-4-ol;
5-(1-benzyl-1H-pyrazol-4-yl)-2-(1H-pyrazol-1-yl)pyrimidin-4-ol;
5-phenyl-2-(1H-pyrazol-1-yl)pyrimidin-4-ol;
N-(4-chlorophenyl)-2-(4-hydroxy-2-(1H-pyrazol-1-yl)pyrimidin-5-yl)acetamide;
N-cyclohexyl-2-(4-hydroxy-2-(1H-pyrazol-1-yl)pyrimidin-5-yl)acetamide;
2-(4-hydroxy-2-(1H-pyrazol-1-yl)pyrimidin-5-yl)-N-isopropylacetamide;
4-hydroxy-2-(pyridazin-3-yl)-N-tosylpyrimidine-5-carboxamide;
and pharmaceutically acceptable salts and solvates thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_0$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), NHC(O)OC$_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond; or when the term appears at the terminus of a substituent, $C_{0-6}$ alkyl means hydrogen or C1-6alkyl. Similarly, when an integer defining the presence of a certain number of atoms in a group is equal to zero, it means that the atoms adjacent thereto are connected directly by a bond. For example, in the structure

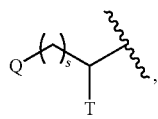

wherein s is an integer equal to zero, 1 or 2, the structure is

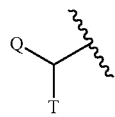

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

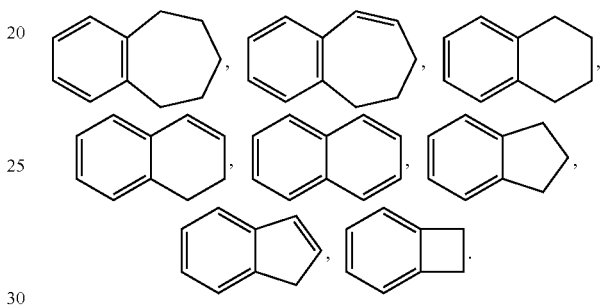

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S, Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl (i.e.,

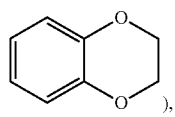

), imidazo(2,1-b)(1,3)thiazole, (i.e.,

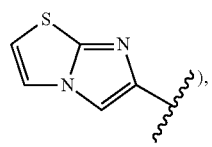 [SMILES: *c1cn2ccsc2n1]

), and benzo-1,3-dioxolyl (i.e.,

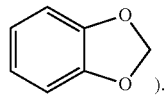

).

In certain contexts herein,

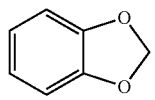

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)— ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

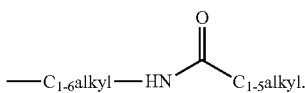

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment, A, includes, but is not limited to, the following: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl, wherein A is optionally substituted with one or more $R^9$ substituents.

In a variant of this embodiment, the heterocyclyl moiety in A includes azabenzimidazole, benzoimidazolyl, benzothiazolyl, benzothienyl, benzotriazolyl, benzothiophenyl, benzoxazolyl, furanyl, imidazolyl, indolyl, indazolyl, isobenzofuryl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridinyl, pyrimidyl, quinazolinyl, quinolyl, quinoxalinyl, quinoxalinyl, tetrahydroisoquinolinyl, tetrazolyl, tetrazolopyridyl, thiadiazolyl, thiazolyl, thienyl, dihydrobenzoimidazolyl, phenothiazinyl, dihydrobenzofuryl, dihydrobenzothiophenyl, dihydrobenzoxazolyl, methylenedioxybenzoyl, tetrahydrofuryl, tetrahydrothienyl, 2,3-dihydrobenzofuryl, 2,3-dihydrobenzo-1,4-dioxinyl, imidazo(2,1-b)(1,3)thiazole, and benzo-1,3-dioxolyl, wherein A is optionally substituted with one or more $R^9$ substituents.

In another embodiment, A is selected from: benzoimidazolyl, benzothiazolyl, benzothienyl, benzotriazolyl, benzothiophenyl, benzoxazolyl, furanyl, imidazolyl, indolyl, indazolyl, isobenzofuryl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridinyl, pyrimidyl, tetrazolyl, tetrazolopyridyl, thiadiazolyl, thiazolyl, and thienyl, wherein A is optionally substituted with one or more $R^9$ substituents.

In another embodiment, A is selected from: pyrazinyl, pyrazolyl, pyridopyridinyl, pyridazinyl, pyridinyl, pyrimidyl, tetrazolyl, tetrazolopyridyl, thiadiazolyl, thiazolyl, and thienyl, wherein A is optionally substituted with one or more $R^9$ substituents.

In another embodiment, A is selected from pyrazinyl, pyrazolyl, pyridazinyl, pyridinyl, and pyrimidyl, wherein A is optionally substituted with one or more $R^9$ substituents. In a variant of this embodiment, A is selected from pyrazolyl, pyridinyl, pyridazinyl, and pyrimidyl, wherein A is optionally substituted with one or more $R^9$ substituents. In yet another variant of this invention, A is chosen from pyrazolyl and pyridazinyl, wherein A is optionally substituted with one or more $R^9$ substituents.

In one embodiment of the invention, $R^1$ is selected from halogen, $C_{1-10}$ alkyl, —$C2_{-10}$ alkenyl, —$C_{2-10}$ alkynyl, cycloalkyl $C_{0-10}$ alkyl(oxy)$_{0-1}$, heterocyclyl $C_{0-10}$ alkyl (oxy)$_{0-1}$, aryl$C_{0-10}$ alkyl(oxy)$_{0-1}$, $C_{1-10}$ alkoxy (carbonyl)$_{0-1}$$C_{0-10}$ alkyl, carboxyl $C_{0-10}$ alkyl, carboxyl aryl, carboxylcycloalkyl, carboxylheterocyclyl, $C_{1-10}$alkyloxy $C_{0-10}$alkyl, hydroxy $C_{0-10}$alkyl, hydroxycarbonyl $C_{0-10}$alkoxy, $C_{1-10}$alkylthio, $C_{1-10}$ alkylsulfinyl, aryl $C_{0-10}$ alkylsulfinyl, heterocyclyl $C_{0-10}$ alkylsulfinyl, cycloalkyl $C_{0-10}$ alkylsulfinyl, $C_{1-10}$ alkylsulfonyl, aryl $C_{0-10}$ alkylsulfonyl, heteroeyclyl$C_{0-10}$ alkylsulfonyl, cycloalkyl $C_{0-10}$ alkylsulfonyl, nitro, perfluoro$C_{1-6}$alkyl, and perfluoro$C_{1-6}$alkoxy; wherein in $R^1$ is optionally substituted with one or more $R^9$ substituents.

In another embodiment, $R^1$ is selected from halogen, $C_{1-10}$ alkyl, —$C2_{-10}$ alkenyl, —$C_{2-10}$ alkynyl, cycloalkyl $C_{0-10}$ alkyl(oxy)$_{0-1}$, heterocyclyl $C_{0-10}$ alkyl(oxy)$_{0-1}$, aryl$C_{0-10}$ alkyl(oxy)$_{0-1}$, $C_{1-10}$ alkoxy (carbonyl)$_{0-1}$$C_{0-10}$ alkyl, carboxyl $C_{0-10}$ alkyl, carboxyl aryl, carboxylcycloalkyl, carboxylheterocyclyl, $C_{1-10}$alkyloxy hydroxy $C_{0-10}$alkyl, hydroxycarbonyl$C_{0-10}$alkoxy, $C_{1-10}$ alkylthio, $C_{1-10}$ alkylsulfinyl, aryl $C_{0-10}$ alkylsulfinyl, heterocyclyl $C_{0-10}$ alkylsulfinyl, cycloalkyl $C_{0-10}$ alkylsulfinyl, $C_{1-10}$ alkylsulfonyl, aryl $C_{0-10}$ alkylsulfonyl, heterocyclyl$C_{0-10}$ alkylsulfonyl, cycloalkyl $C_{0-10}$ alkylsulfonyl, nitro, perfluoroC$_{1-6}$allyl, and perfluoroC$_{1-6}$alkoxy; wherein in R$^1$ is optionally substituted with one or more R$^9$ substituents.

In another embodiment, R$^1$ is selected from halogen, phenylmethyl, pyridinyl, phenyl, C$_{1-10}$ alkyl, naphtholinyl C$_{1-6}$ alkyl, cyclopropyl, phenyl C$_{1-6}$ alkyl, cyclohexyl, piperidinyl, pyrrolidinyl, 1,2,3,4-tetrahydronaphthalinenyl, 2,3-dihydro-1H-indinyl, benzyl, phenylethyl, cyclopentyl, tertbutyl, wherein in R$^1$ is optionally substituted with one or more R$^9$ substituents.

In another embodiment of the invention, R$^1$ is selected from: cycloalkyl C$_{0-10}$ alkyl(oxy)$_{0-1}$, heterocyclyl C$_{0-10}$ alkyl (oxy)$_{0-1}$, arylC$_{0-10}$ alkyl(oxy)$_{0-1}$, perfluorC$_{1-6}$alkyl, perfluoro C$_{1-6}$alkoxy, and C$_{1-10}$ alkoxy (carbonyl)$_{0-1}$C$_{0-10}$ alkyl, wherein R$^1$ is optionally substituted with one or more R$^9$ substituents.

In one embodiment of the invention, R$^2$ is selected from hydrogen, halogen, hydroxyl, —C$_{1-6}$ alkyl, C$_{3-6}$ heterocycloalkyl and C$_{3-6}$ cycloalkyl wherein said alkyl, heterocycloalkyl and cycloalkyl are each optionally substituted with one or more substituents selected from: hydroxyl, —SR$^a$, —NR$^a_2$ or —CO$_2$—R$^a$.

In another embodiment, R$^3$ is selected from hydrogen, halogen, hydroxyl, —C$_{1-6}$ alkyl, C$_{3-6}$ heterocycloalkyl and C$_{3-6}$ cycloalkyl wherein said alkyl, heterocycloalkyl and cycloalkyl are each optionally substituted with one or more substituents selected from: hydroxyl, —SR$^a$, —NR$^a_2$ or —CO$_2$—R$^a$.

In one embodiment of the invention L is selected from: is chosen from —(C$_{1-3}$ alkyl)$_{0-1}$NR$^a$CO—, —(C$_{1-3}$ alkyl)$_{0-1}$NR$^a$CO$_2$—, (C$_{1-3}$ alkyl)$_{0-1}$CO$_2$—, alkyl)$_{0-1}$NR$^a$SO$_2$—, —(C$_{1-3}$ alkyl)$_{0-1}$NR$^a$CSNR$^b$—, and —(C$_{1-3}$ alkyl)$_{0-1}$NR$^a$CONR$^b$—.

In another embodiment, L is selected from (C$_{1-3}$ alkyl)0-1NRaCO—, —(C1-3 alkyl)0-1NRaCO2-, and —(C1-3 alkyl)0-1CO2-. In a variant of this embodiment, L is —(C1-3 alkyl)0-1NRaCO—.

In one embodiment, R9 is selected from halogen, hydroxy, oxo, cyano, aryl, heterocyclyl, cycloalkyl, —C1-6 alkyl, —C1-6 alkoxy, aryloxy, heterocyclyloxy, —O(0-1)(C1-10) perfluoroalkyl, —CO2Ra, —OCO2Ra, —OCONRbRc, —SC0-6 alkyl and —S(O)$_n$Rd, wherein R9 is optionally substituted by one or more substituents R10.

In another embodiment, R9 is selected from halogen, hydroxy, cyano, aryl, heterocyclyl, cycloalkyl, —C1-6 alkyl, —C1-6 alkoxy, aryloxy, heterocyclyloxy, —O(0-1)(C1-10) perfluoroalkyl, —CO2Ra, and —OCO2Ra wherein R9 is optionally substituted by one or more substituents R10.

In one embodiment, R10 is selected from hydroxy, aryl, heterocycloalkyl, heteroaryl, halogen, oxo, —C$_{1-6}$ alkyl, C$_{1-6}$ alkoxy, CO$_2$H, cyano, O(C=O)$_{0-1}$C$_{1-6}$ alkyl, trifluoromethoxy, trifluoroethoxy, —O$_{(0-1)}$(C$_{1-10}$)perfluoroalkyl, C$_{0-10}$ alkylaminocarbonyl, —(C=O)N(C$_{0-6}$ alkyl)$_2$, —S(C$_{0-6}$ alkyl), and NH$_2$.

In another embodiment, R$^{10}$ is selected from hydroxy, aryl, heterocycloalkyl, heteroaryl, halogen, oxo, —C$_{1-6}$ alkyl, C$_{1-6}$ alkoxy, CO$_2$H, cyano, O(C=O)$_{0-1}$C$_{1-6}$ alkyl, trifluoromethoxy, trifluoroethoxy, —O$_{(0-1)}$(C$_{1-10}$)perfluoroallyl, C$_{0-10}$ alkylaminocarbonyl, and NH$_2$.

Another embodiment of the invention includes the following compounds:

N-(4-hydroxy-2-(1H-pyrazol-1-yl)pyrimidin-5-yl)-2,2-diphenylacetamide;
2-chloro-N-(4-hydroxy-2-(1H-pyrazol-1-yl)pyrimidin-5-yl) benzamide;
3-chloro-N-(4-hydroxy-2-(1H-pyrazol-1-yl)pyrimidin-5-yl) benzamide;
3-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-(naphthalen-3-yl)acetamide;
2-(trifluoromethyl)-N-(4-hydroxy-2-(1H-pyrazol-1-yl)pyrimidin-5-yl)benzamide;
N-[4-hydroxy-2-(1H-pyrazol-1-yl)pyrimidin-5-yl]biphenyl-4-carboxamide;
N-(4-hydroxy-2-(1H-pyrazol-1-yl)pyrimidin-5-yl)-3-phenoxybenzamide;
N-(4-hydroxy-2-(1H-pyrazol-1-yl)pyrimidin-5-yl)-4-phenoxybenzamide;
2-(2-chlorophenyl)-N-(4-hydroxy-2-(1H-pyrazol-1-yl)pyrimidin-5-yl)acetamide;
2-(3-chlorophenyl)-N-(4-hydroxy-2-(1H-pyrazol-1-yl)pyrimidin-5-yl)acetamide;
2-(4-chlorophenyl)-N-(4-hydroxy-2-(1H-pyrazol-1-yl)pyrimidin-5-yl)acetamide;
2-(3-cyanophenyl)-N-(4-hydroxy-2-(1H-pyrazol-1-yl)pyrimidin-5-yl)acetamide;
2-(2-(trifluoromethyl)phenyl)-N-(4-hydroxy-2-(1H-pyrazol-1-yl)pyrimidin-5-yl)acetamide;
2-(3-(trifluoromethyl)phenyl)-N-(4-hydroxy-2-(1H-pyrazol-1-yl)pyrimidin-5-yl)acetamide;
2-(4-(trifluoromethyl)phenyl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(2-methoxyphenyl)acetamide;
N-(4-hydroxy-2-(1H-pyrazol-1-yl)pyrimidin-5-yl)-2-(3-methoxyphenypacetamide;
N-(4-hydroxy-2-(1H-pyrazol-1-yl)pyrimidin-5-yl)-2-(4-methoxyphenyl)acetamide;
N-(4-hydroxy-2-(1H-pyrazol-1-yl)pyrimidin-5-yl)-2-phenylpropanamide;
N-(4-hydroxy-2-(1H-pyrazol-1-yl)pyrimidin-5-yl)-2-phenylbutanamide;
N-(4-hydroxy-2-(1H-pyrazol-1-yl)pyrimidin-5-yl)-3-methyl-2-phenylpentanamide;
N-(4-hydroxy-2-(1H-pyrazol-1-yl)pyrimidin-5-yl)-2-methyl-2-phenylpropanamide;
N-(4-hydroxy-2-(1H-pyrazol-1-yl)pyrimidin-5-yl)-2-(naphthalen-1-yl)acetamide;
2-(benzo[d][1,3]dioxol-5-yl)-N-(4-hydroxy-2-(1H-pyrazol-1-yl)pyrimidin-5-yl)acetamide;
2-(biphenyl-4-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)heptanamide;
N-(4-hydroxy-2-(1H-pyrazol-1-yl)pyrimidin-5-yl)-4-phenylbutanamide;
tert-butyl-4-(4-hydroxy-2-(1H-pyrazol-1-yl)pyrimidin-5-ylcarbamoyl)piperidine-1-carboxylate;
2-cyclohexyl-N-(4-hydroxy-2-(1H-pyrazol01.01-1-yl)pyrimidin-5-yl)acetamide;
1,2,3,4-tetrahydro-N-(4-hydroxy-2-(1H-pyrazol-1-yl)pyrimidin-5-yl)naphthalene-1-carboxamide;
2,3-dihydro-N-(4-hydroxy-2-(1H-pyrazol-1-yl)pyrimidin-5-yl)-1H-indene-1-carboxamide;
2,3-dihydro-N-(4-hydroxy-2-(1H-pyrazol-1-yl)pyrimidin-5-yl)-1H-indene-2-carboxamide;
1-benzyl-3-(4-hydroxy-2-(1H-pyrazol-1-yl)pyrimidin-5-yl) urea;
1-(4-hydroxy-2-(1H-pyrazol-1-yl)pyrimidin-5-yl)-3-(1-phenylethyl)urea;
3-(4-hydroxy-2-(1H-pyrazol-1-yl)pyrimidin-5-yl)-1,1-diphenylurea;

1-benzhydryl-3-(4-hydroxy-2-(1H-pyrazol-1-yl)pyrimidin-5-yl)thiourea;
1-(4-hydroxy-2-(1H-pyrazol-1-yl)pyrimidin-5-yl)-3-(1-phenylethyl)thiourea;
and pharmaceutically acceptable salts and solvates thereof.

Structural representations of compounds having substituents terminating with a methyl group may display the terminal methyl group either using the characters "CH$_3$", e.g. "—C$_{1\text{-}13}$" or using a straight line representing the presence of the methyl group, e.g., "—", i.e.,

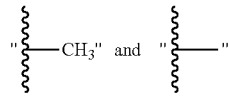

have equivalent meanings.

For variable definitions containing terms having repeated terms, e.g., (CR$^i$R$^j$)$_r$, where r is the integer 2, R$^i$ is a defined variable, and R$^j$ is a defined variable, the value of R$^i$ may differ in each instance in which it occurs, and the value of R$^j$ may differ in each instance in which it occurs. For example, if R$^i$ and R$^j$ are independently selected from the group consisting of methyl, ethyl, propyl and butyl, then (CR$^i$R$^j$)$_2$ can be

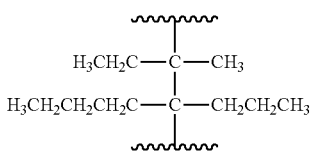

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms).

Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, infrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdennal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in. *Remington's Pharmaceutical Sciences, A. Osol, a standard reference text in this field.*

For administration by inhalation, the compounds of the present invention may be conveniently delivered in the form of an aerosol spray presentation from pressurized packs or nebulisers.

The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient. Abbreviations Used in the Description of the Preparation of the Compounds of the Present Invention:

AcOH Acetic acid
$Ag_2O$ Silver oxide
Aq Aqueous
Bn Benzyl
BnBr benzylbromide
BnCl benzylchloride
BnOH benzylalcohol
Brine Saturated aqueous sodium chloride solution
CDI Carbonyl diimidazole
DBU 1,8-diazabicyclo[5.4.0]undec-7-ene
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide
EDC or EDCI 1-(3-dimethylaminopropyl)-3-ethylcarboiimide hydrogenchloride salt
EtOAc or EA Ethyl acetate
Et (et) Ethyl
EtOH Ethanol
$Et_2O$ or ether Diethyl ether Et₃N triethylamine
G Grams
h or hr Hour
HATU O-(7-Azabenzotriazol-1-yl)-N,N,N',N'-tetramethyluronium hexafluorophosphate
HCl Hydrochloric acid
HOBt 1-hydroxybenzatriazole
HPLC High-performance liquid chromatography
i-PrOH or IPA Isopropyl alcohol
$K_2CO_3$ Potassium carbonate
KOH Potassium hydroxide
LiOH Lithium hydroxide
Mg Milligrams
mL Milliliters
Mmol Millimole
MeOH Methanol
Min Minutes
ms or MS Mass spectrum
Mg Microgram(s)
μL Microliters
NaOEt Sodium ethoxide
NaOMe Sodium methoxide
$Na_2SO_4$ Sodium sulfate
NHAc Acetamido
NHCbz Benzyloxycarboxamido
NaOH Sodium hydroxide
$NaN_3$ Sodium azide
$NH_4OH$ ammonium hydroxide
Pd/C Palladium on carbon
$Pd(OH)_2$ Palladium hydroxide
Ph Phenyl group
$PPh_3$ Triphenyphosphine
$R_f$ Retention time
Rt Room temperature
TEA Triethylamine
TFA Trifluoroacetic acid
THF Tetrahydrofuran
$TMSCHN_2$ (trimethylsilyl)diazomethane
V/V Volume/Volume
V Volume
Synthesis The compounds of this invention may be prepared by employing reactions as shown in the following schemes, in addition to other manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The following schemes and descriptions illustrate methods which may be employed for the synthesis of the novel compounds described in this invention. All substituents are as defined above unless indicated otherwise. Several strategies based upon synthetic transformations known in the literature of organic synthesis may be employed for the preparation of the title compounds of general formula I. The choice of the method employed is influenced by the selection of the desired substituent groups ($R^1$ through $R^3$, L and A) in the title compounds of general formula I.

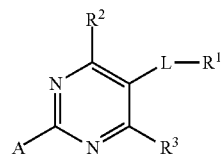

Pyrimidine intermediates useful for the preparation of compounds of formula I of the present invention are either purchased or prepared using suitable procedures reported in the literature (sometimes with minor modifications). One generally useful method for the synthesis of pyrimidines suitable for the preparation of the title compounds of general formula I wherein the substituent $R^3$ is a hydroxyl group is illustrated in Scheme 1.

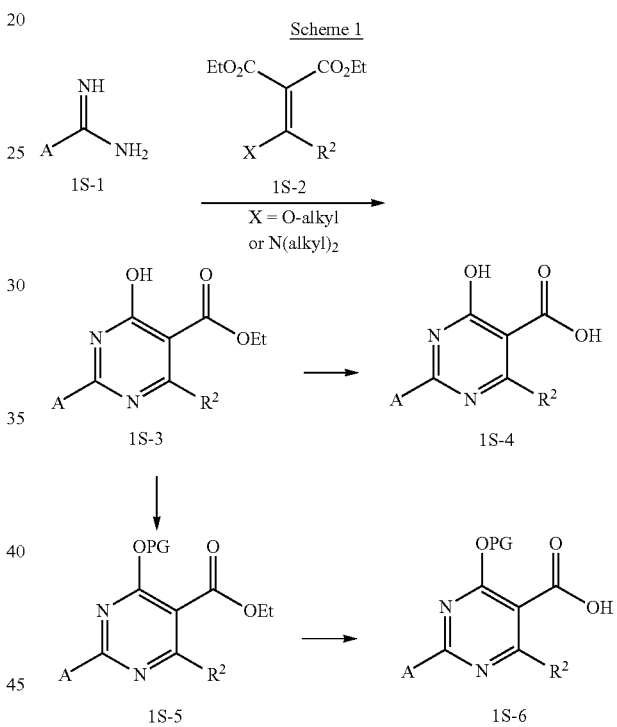

This method involves the initial synthesis of substituted 4-hydroxypyrimidine-5-carboxylates of general formula 1S-4 and 1S-6. The synthesis of 4-hydroxypyrimidine-5-carboxylates exemplified in scheme 1 is based upon reported methods (Dosteit, P.; Imbert, T.; Antler, J. F.; Langlois, M.; Bucher, B.; Mocquet, G. *Eur. J. Med. Chem.* 1982, 17, 437-44. Juby, P. P.; Hudyma, T. W.; Brown, M.; Essery, J. M.; Partyka, R. A. *J. Med. Chem.* 1979, 22, 263-9).

In this method, an amidine or a suitable salt thereof of general formula 1S-1 is reacted with an optionally substituted diethyl methylenemalonate of general formula 1S-2. This reaction is usually conducted using a suitable base such as sodium or potassium ethoxide in ethanol, although other reaction conditions may also be applied. The alkoxide base and the alcohol solvent are chosen to correspond to the esters present in reagent 1S-2 to prevent the formation of mixtures of esters in the product of general formula 1S-3. When required, the reaction is conducted at elevated temperature, typically at the reflux temperature of the solvent until reaction is complete (generally within 1-4 hours). It is also convenient to conduct this reaction under microwave heating in sealed reaction vessels. In this instance, the reaction is generally conducted at temperatures between 80 and 120° C. and the reactions are typically completed in 5-30 minutes.

Compounds of general formula 1S-3 are useful intermediates to prepare compounds of formula I of the present invention. For example, compounds of general formula 1S-3 may be hydrolyzed using a suitable base (e.g. sodium or potassium hydroxide) to give acids of formula 1S-4; alternatively, they are converted to compounds of formula 1S-5, in which the hydroxyl group of the pyrimidine core is protected with a desired protecting group (e.g. PG is benzyl, para-methoxybenzyl, trityl, or Cert-butyl-dimethyl silyl). Hydrolysis of compounds of formula 1S-5 gives acids of general formula 1S-6, which is readily achieved under suitable ester hydrolysis reaction conditions (Wuts, P. G. M.; Greene, T. W., Protecting Groups in Organic Synthesis, John Wiley and Sons, 4$^{th}$ Edition, 2007).

When amidines of general formula 1S-1 are not commercially available, they may be prepared by a variety of methods known in the literature. Amidines are commonly prepared from nitriles using the Pinner reaction and variations thereof (see Amidines and N-substituted amidines. Dunn, Peter J. in Comprehensive Organic Functional Group Transformations 1995, 5, 741-82, 1161-308 Editor(s): Katritzky, Alan R.; Meth-Cohn, Otto; Rees, Charles Wayne. Publisher: Elsevier, Oxford, 151UK). Amidines may also be prepared from esters using the method reported by Gielen et al. (Gielen, H.; Alonso-Alija, C.; Hendrix, M.; Niewohner, U.; Schauss, D. Tetrahedron Lett. 2002, 43, 419-21).

In instances where the substituent A is selected to be a five-membered heterocyclic ring, it is possible that this heterocyclic group be bonded to the carbon atom at the 2-position of the pyrimidine ring through either a carbon-carbon or a carbon-nitrogen bond. In the case of attachment through a carbon-carbon bond, the precursor for the substituent A is an amidine of general formula 1S-1 and the method using 1S-1 for the synthesis of the title compound of general formula I is as described in the preceding reaction schemes.

When a substituent A is attached through a carbon-nitrogen bond, the precursor for the substituent A is a guanidine of general formula 2S-7. In this example, the synthesis begins with the condensation of the guanidine derivative of general formula 2S-7 with compounds of general formula 2S-8 (or a diethyl ethoxymethylenemalonate of general formula 1S-2 when it is desired that R$^3$=OH) to afford the substituted pyrimidine-5-carboxylate derivative of general formula 2S-9. Ester hydrolysis as described above affords compounds of formula 2S-10, which is useful to prepare compounds of general formula I wherein the group A is a five-membered heterocyclic group attached to the pyrimidine 2-position with a carbon-nitrogen bond.

Scheme 2

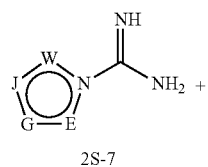

2S-7

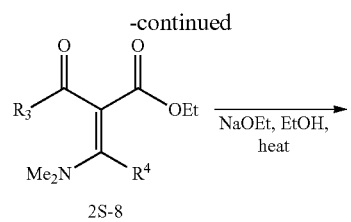

2S-8

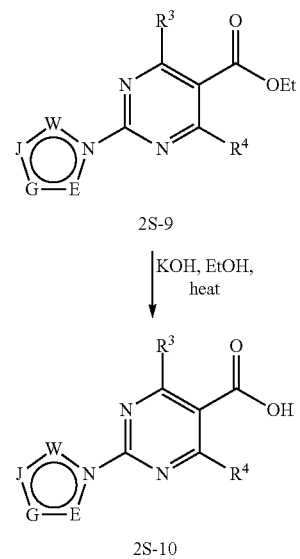

2S-9

2S-10

In cases when the guanidine derivative (2S-7) bearing the desired substituents is not commercially available, it may be synthesized using reported methods for guanidine synthesis (e.g. the guanidinylation of amines). Numerous methods for the guanidinylation of amines are reported (see Katritzky, A. R.; Rogovoy, B. V. ARKIVOC 2005, 4, 49-87; http://www.ar-kat-usa.org/ark/journal/2005/104_Zefirov/1256/1256.pdf). One general method is shown in Scheme 3, which entails the reaction of compounds of formula 3S-11 with 3,5-dimethyl-1-pyrazolylformamidinium nitrate to afford a guanidine of general formula 3S-12 using the method described by Fletcher et al. (Fletcher, Ganellin, C. R.; Piergentili, A.; Dunn, P. M.; Jenkinson, D. H. Bioorg. Med. Chem. 2007, 15, 5457-79).

Scheme 3

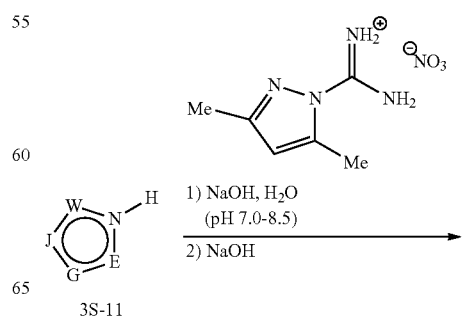

3S-11

-continued

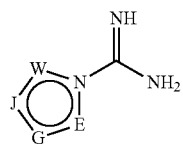

3S-12

It is recognized that the title compounds of general formula I prepared as described above may be further modified using known methods and that the starting materials selected for use in the reaction schemes above may contain functional groups to enable said further transformation. For instance, aromatic rings in the title compounds of general formula 1 may be subjected to a variety of aromatic substitution reactions such as nitration, halogenation and the like. Aromatic substituent groups in the title compounds of general formula I bearing leaving groups such as halogens, triflates or the like, can be employed in a variety of metal-catalyzed cross coupling reactions to incorporate new substitution patterns. For example, palladium-catalyzed cross coupling reactions such as those described by Suzuki, Stille, Buchwald and others, may be used to introduce a variety of new substituent groups. Substituent groups that may be introduced using such cross-coupling methods include, but are not limited to, alkyl, alkenyl, alkynyl and aryl groups as well as acyl groups (e.g. carboxylic acids, esters, amides, or ketones), hydroxyl and amino or substituted amino groups.

Other pyrimidines with various substituents at the 5-position (wherein R" is not a carboxylate) are also prepared via cyclization reactions described in Schemes 1 & 2, which are exemplified in Scheme 4.

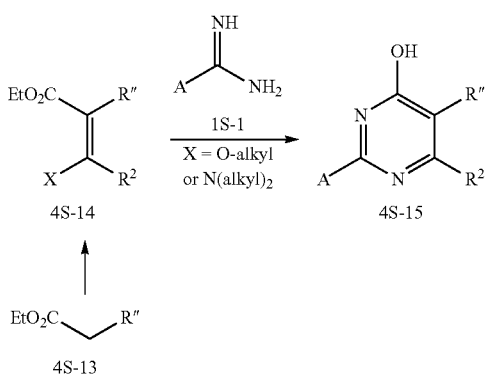

For example, compounds of formula 4S-15 are prepared when amidines 1S-1 are cyclized with esters 4S-14 wherein X=O-alkyl under reaction conditions exemplified as in Scheme 1. Alternatively, compounds of formula 4S-14 wherein X=N(alkyl)$_2$ are also cyclized with amidines 1S-1 to give compounds of formula 4S-15 (Chen, W.; Feng, J.; Tu, H. *Huaxue Tongbao,* 2006, 69, 623-6). The esters 4S-14 can be prepared by reaction of esters 4S-13 with a substituted carboxamide dimethyl acetal.

The methods presented in reaction Schemes 1 and 2 may be further generalized when it is desired to prepare compounds of general formula I where neither of the R$^3$ or R$^4$ substituents are hydroxyl groups.

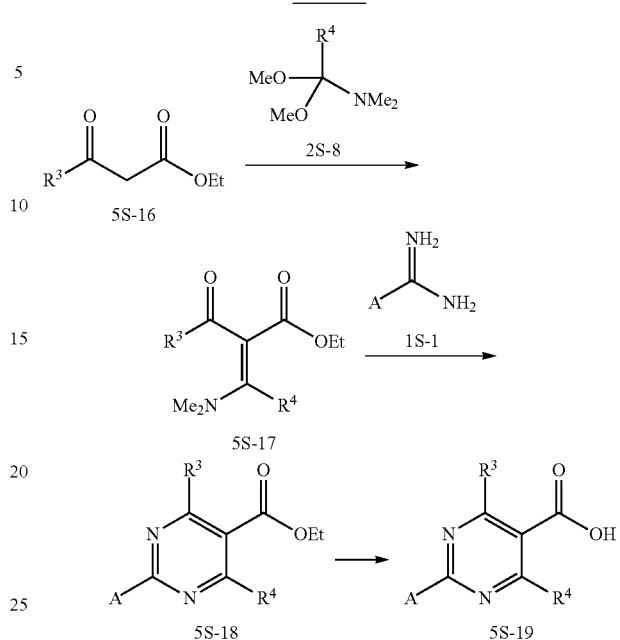

Reaction Scheme 5 illustrates the process beginning with a beta-ketoester of general formula 5S-16 bearing the R$^3$ substituent. The ester of general formula 5S-16 is condensed with a carboxamide dimethyl acetal of general formula 2S-8 to afford the vinylogous amide of general formula 5S-17. The intermediate 5S-17 is then reacted with an amidine derivative of general formula 1S-1 using the method of Schenone et al. (Schenone, P.; Sansebastiano, L.; Mosti, L. *J. Heterocyclic Chem.* 1990, 27, 295) to afford the alkyl pyrimidine-5-carboxylate of general formula 5S-18. Hydrolysis of compounds of formula 5S-18 under suitable conditions (e.g. KOH or NaOH in EtOH—H$_2$O, heating when necessary) produces compounds of formula 5S-19. The compounds of general formula 5S-19 are then converted to the title compounds of general formula I using the methods described previously.

In one aspect, compounds of formula I are prepared via pyrimidine ring formation reactions (e.g. Schemes 1, 2, 4, 5) with the desired substituents (e.g. A, R$^2$, R$^3$ and L) at various positions. In another aspect, the desired substituents on the pyrimidine core can be introduced after the pyrimidine ring is formed, which can be achieved using synthetic methods reported in the literature. For example, the hydroxyl group present at the pyrimidine 4-position in compounds of general formulae 1S-3, 1S-4, or 4S-15 may be converted to a halogen substituent upon reaction with a suitable halogenating reagent (e.g. POCl$_3$, BBr$_3$, etc.).

Compounds of general formula I wherein L is an amino or an amino derivative can be prepared from suitable pyrimidine derivatives such as 1S-4, 1S-6, 2S-10 and 5S-19 using synthetic methods reported in the literature. For example, carboxylic acids of formula 5S-19 are converted to their corresponding amines of formula 6S-20 using suitable methods such as Curtis rearrangement reactions, Scheme 6. The amino group in compounds of formula 6S-20 is further derivatized using common synthetic methods such as amide bond formation reactions (e.g. CDT couplings, EDCI couplings, reactions with acyl chlorides, etc.), sulfonamide bond formation reactions (e.g. reactions with sulfonyl chlorides in the presence of a suitable base), reductive amination reactions with a suitable carbonyl compounds (e.g. aldehydes and ketones). For example, compounds of formula I wherein L is —NHCO— and/or —NHSO$_2$— are prepared from compounds of formula 6S-20 as depicted in Scheme 6. In another aspect, carboxylic acids such as compounds of formula 5S-19 can be converted to their corresponding acyl azide such as compounds of formula 6S-22, and under suitable thermal rearrangement reaction conditions acyl azides such as 6S-22 can be converted to their corresponding isocyanate, and subsequent reactions of the resulting isocyanate with various nucleophiles such as alcohols, amines and thiols can produce compounds of formula 6S-23 wherein L is a carbamate (—NHCOO—), urea (—NHCONH—), or thiocarbamate (—NHCOS—). (March's advanced organic chemistry, Wiley-interscience, 2007; Comprehensive Organic Transformations: a guide to functional group preparetions by Richard Larock, Wiley-VCH, 2000)

on Waters C18 XBridge 3.5 μm 3.0×50 mm column with gradient 10:90-98:2 v/v CH$_3$CN/H$_2$O+v 0.025% NH$_4$OH over 3.25 min then hold at 98:2 CH$_3$CN+v 0.025% NH$_4$OH for 2.25 min; flow rate 1.0 mL/min, UV wavelength 254 nm. Concentration of solutions was carried out on a rotary evaporator under reduced pressure. Flash chromatography was performed using a Biotage Horizon or SP1 Flash Chromatography apparatus (Dyax Corp.) on silica gel (32-63 μM particle size, KP-Sil 60 Å packing material type) in pre-packed cartridges or using an ISCO CombiFlash™ Sq 16× or CombiFlash® Companion™ apparatus on silica gel (32-63 μM, 60 Å) in pre-packed cartridges. Microwave reactions were carried out on a Biotage Initiator™ 2.0 or CEM Discover™ system. Preparative HPLC/MS Standard Method: Mass analysis was performed on a Waters Micromass® ZQ™ with electrospray ionization in positive ion detection mode. High performance liquid chromatography (HPLC) was conducted Scheme 6

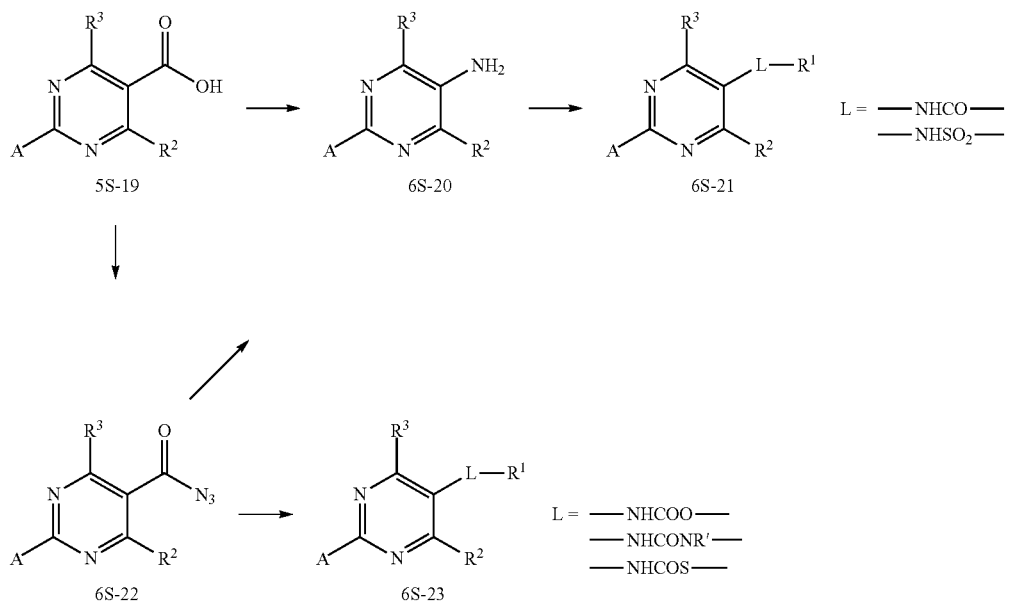

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60E-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O v 0.05% TFA over 3.75 min then hold at 100 CH$_3$CN v 0.05% TFA for 1.75 min; flow rate 1.0 mL/min, UV wavelength 254 nm (all HPLC/MS data was generated with this method unless indicated otherwise). Analytical HPLC/MS—Basic Method: Mass analysis was performed on a Waters Micromass® ZQ™ with electrospray ionization in positive ion detection mode. High performance liquid chromatography (HPLC) was conducted on an Agilent 1100 series HPLC on a Waters Prep. HPLC System on Waters C18 Sunfire 5 μm 30×100 mm column with gradient 10:90-100 v/v CH$_3$CN/H$_2$O v 0.1% TFA over 12 min; flow rate 50 mL/min, UV wavelength 210-400 nm.

Preparative HPLC/MS—Non-Polar Method

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 μm 30×100 mm column with gradient 40:60-100 v/v CH$_3$CN/H$_2$O+v 0.1% TFA over 10 min then hold at 100 CH$_3$CN+v 0.1% TFA for 4 min; flow rate 50 mL/min, UV wavelength 210-400 nm.

Preparative HPLC/MS—Basic Method.

Mass analysis was performed on a Waters Micromass ZQ™ with electrospray ionization in positive ion detection mode. High performance liquid chromatography (HPLC) was conducted on a Waters Prep. HPLC System on Waters C18)(Bridge 5 μm 50×150 mm column with gradient 10:90-

35:65 v/v CH$_3$CN/H$_2$O (pH=10 with NH$_4$OH) over 10 min; flow rate 120 mL/min, UV wavelength 210-400 nm.

Example 1

Synthesis of Intermediate 1-h

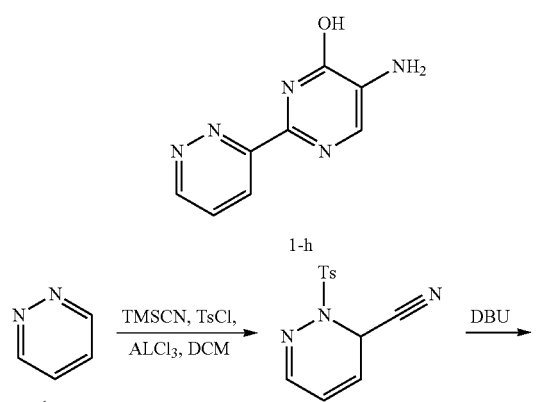

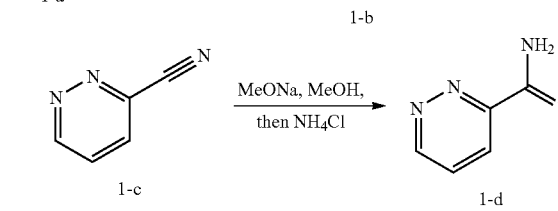

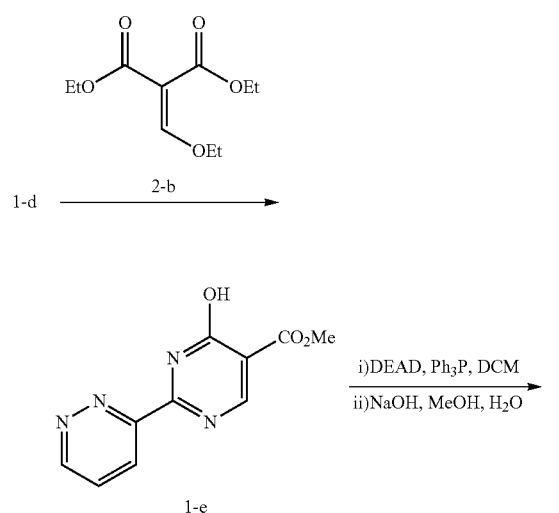

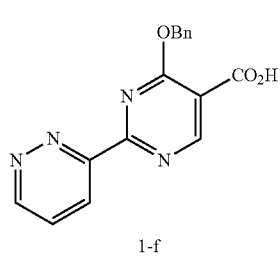

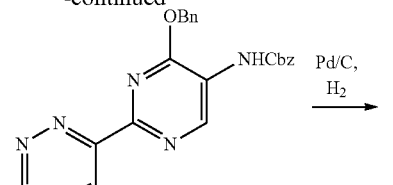

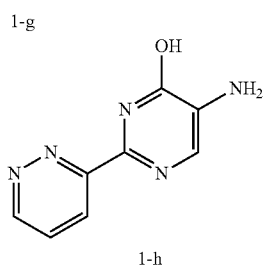

Step A: 2-Tosyl-2,3-dihydropyridazine-3-carbonitrile (1-b)

A solution of pyridazine (5 mL, 69.12 mmol) (Sigma-Aldrich), aluminum chloride (28 mg, 0.21 mmol) and TMSCN (16.75 mmol) in DCM (60 mL) was stirred under a nitrogen atomosphere at 0° C. for 20 min. A solution of TsCl (22.75 g, 119.7 mmol) in DCM (40 mL) was added dropwise. The reaction was warmed to room temperature, stirred for an additional 60 h, and concentrated in vacuo. The residue ws washed with EtOH (150 mL) and the resulting solids were filtered to afford the title compound 1-b (15 g, 83%). $^1$H NMR (300 MHz, CDCl$_3$) δ7.93 (d, J=8.4 Hz, 2H), 7.38 (d, J=1.8 Hz, 2H), 6.23-6.21 (m, 2H), 5.79 d, J=6.3 Hz, 1H), 2.44 (s, 3H). LC-MS: (M+H)$^+$=262.

Step B: Pyridazine-3-carbonitrile (1-c)

To a solution of compound 1-b (9.0 g, 34.4 mmol) in THF (100 mL) was added DBU (6.5 ml, 68.9 mmol). The reaction was stirred at room temperature under a nitrogen atmosphere for 1 h. Saturated aqueous NH$_4$Cl (100 mL) was poured into water (150 mL). The aqueous medium was extracted with EtOAc, dried, filtered and concentrated. The residue was washed with hexane (100 mL) to afford the title compound 1-c (2.7 g, 75%). $^1$H NMR (300 MHz, CDCl$_3$) δ 9.40 (dd, J=1.5, 5.1 Hz), 7.88 (dd, J=1.8, 8.4 Hz), 7.70 (dd, J=5.1, 8.4 Hz). LC-MS: (M+H)$^+$=106.

Step C: Pyridazine-3-carboximidamide hydrochloride (11-d)

To a solution of compound 1-c (2.7 g, 25.7 mmol) in MeOH (25 mL) was added sodium methoxide (139 mg, 0.257 mmol). The reaction was stirred at room temperature overnight when ammonium chloride (1.65 g, 30.8 mmol) was added. The reaction was refluxed for 3 h, cooled to room temperature and concentrated to afford the crude product of 1-d (3.8 g, 93%). $^1$H NMR (300 MHz, DMSO-d$_6$) δ 9.38 (dd, J=1.5, 5.1 Hz, 1H), 8.30 (dd, J=1.5, 8.7 Hz, 1H), 7.92 (dd, J=5.1, 8.4 Hz, 1H). LC-MS: (M+H)$^+$123.

Step D: Methyl 4-hydroxy-2-(pyridazin-3-yl)pyrimidine-5-carboxylate (1-e)

A mixture of crude compound 1-d (20.0 g, 34.4 mmol), diethyl ethoxymethylenemalonate (35.0 g 162 mmol) and sodium methoxide (10.0 g, 185 mmol) in MeOH (1000 mL) was refluxed overnight. The reaction mixture was cooled and concentrated to remove the solvent and the residue was added to water (500 mL), extracted with EtOAc (500 mL). The organic phase was adjusted to pH=2 by addition of aq. HCl. The solids were filtered to afford the product 11-e (15.0 g, 39%). LC-MS: (M+H)$^+$=233.

Step E: 4-(benzyloxy)-2-(pyridazin-3-yl)pyrimidine-5-carboxylic acid (1-f)

A mixture of compound 11-e (1.5 g, 6.316 mmol) and PPh$_3$ (3.39 g, 12.98 mmol) in THF(50 mL) was drop wise added with DEAD (2.26 g, 12.98 mmol) and stirred at room temperature for 30 min. Then BnOH (0.84 g, 7.75 mmol) was added and the mixture was stirred for additional 12 h at room temperature. The reaction mixture was concentrated. The residue was purified by chromatography column with eluent PE: EA=2:1 to afford crude 11-f.

A solution of the crude compound (2.1 g, crude) in MeOH (30 mL) was added with aqueous LiOH (0.55 g, 12.9 mmol, 1M) and stirred at room temperature for overnight. The reaction mixture was concentrated, dissolved in water (30 mL), and extracted with EtOAc (50 mL). The aqueous layer was adjusted to pH=2 by addition of aq. HCl. The solids were filtered to afford the product 1-f (400 mg, 21%) LC-MS: (M+H)$^+$=309.

Step F: 4-(benzyloxy)-2-(pyridazin-3-yl)pyrimidine-5-carboxylic acid (1-g)

A mixture of compound 1-f (200 mg, 0.649 mmol), DPPA (196 mg, 0.71 mmol), Et$_3$N (197 mg, 1.95 mmol) and BnOH (105 mg, 0.97 mmol) in THF/toluene (20 mL, 1:1) was stirred at 65° C. overnight. The reaction mixture was concentrated and purified by chromatography column with eluent PE: EA=2:1 to afford the product 1-g (160 mg, 60%). LC-MS: (M+H)$^+$=414.

Step G: 4-(benzyloxy)-2-(pyridazin-3-yl)pyrimidine-5-carboxylic acid (1-h)

A solution of compound 1-g (160 mg, 0.387 mmol) in MeOH (5 mL) was added with Pd/C (10%, 0.15 g) and stirred under hydrogen for 5 h. The mixture was filtered and the solution was concentrated to afford the crude product 11-h (450 mg). LC-MS: (M+H)$^+$=190.

Example 2

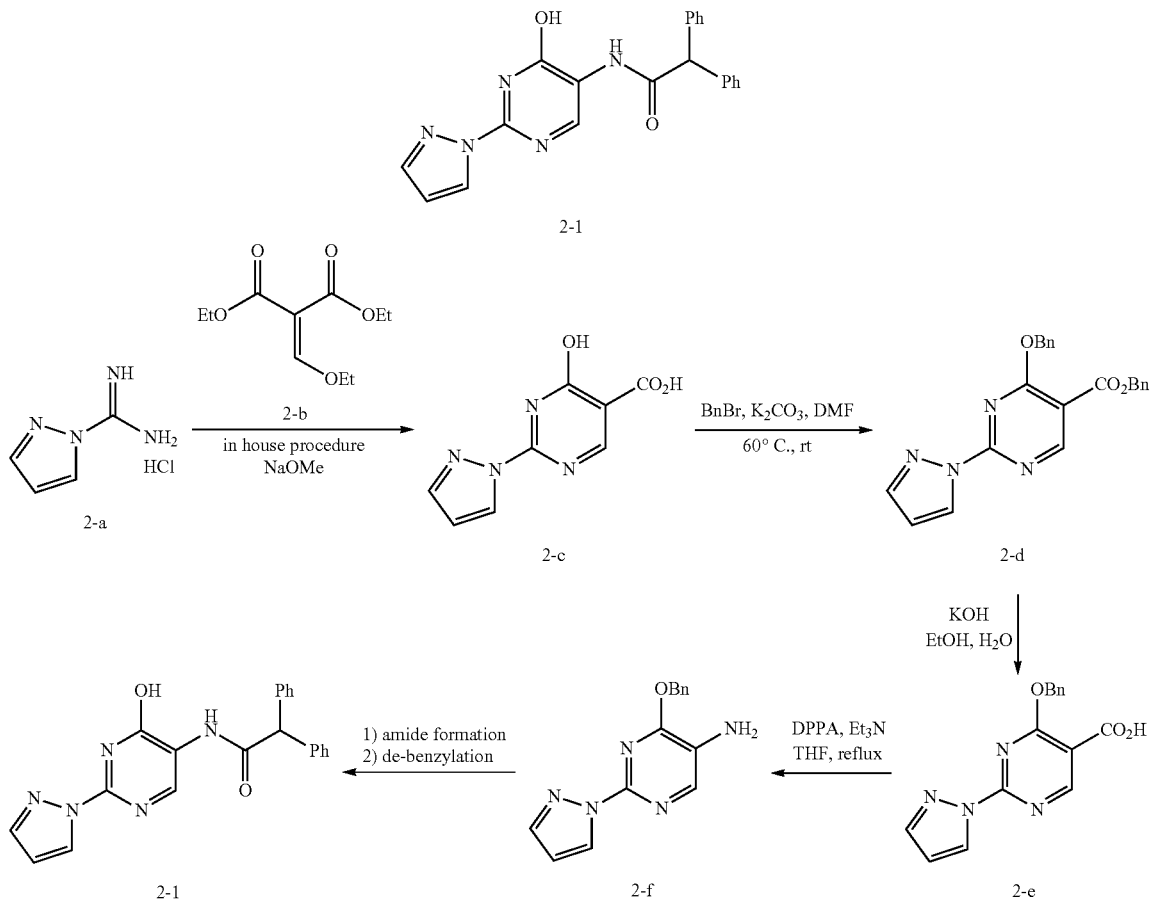

Step A: 4-hydroxy-2-(1H-pyrazol-1-yl)pyrimidine-5-carboxylic acid (2-e)

To 1H-pyrazole-1-carboximidamide hydrochloride (Sigma-Aldrich), 2-a, (44.22 g, 299 mmol) in EtOH (500 mL) was added sodium methoxide (102 mL, 448 mmol, 25 wt% in MeOH) and diethyl ethoxymethylenemalonate (Sigma-Aldrich), 2-b, (61.0 mL, 299 mmol, 99%). The reaction was heated for about 40 min at 75° C. and then cooled slightly (71° C.) before adding potassium hydroxide (33.5 g, 597) in water (125 mL). The reaction was heated to 75° C. for 1 h. During this time an additional portion of EtOH (100 mL) was added to improve mixing. The reaction was cooled to 40° C. before adding aqueous HCl (81.3 mL, 991 mmol, 37%) in portions. The reaction aged for 1 h 40 min and then Et2O (180 mL) was added. The solids were filtered and rinsed with EtOH, Et2O, and then hexane. The solid was then suspended in aqueous HCl (300 mL, 0.67 M), filtered and washed with aqueous HCl (300 mL, 1 M), 2:1 Et$_2$O:EtOH (350 mL), 1:1 Et$_2$O:EtOH (200 mL), Et$_2$O (150 mL) and then hexane (150 mL) to afford the compound, 2-c. HPLC/MS: 207.2 (M+1); Rt=0.61 min.

Step B: Benzyl 4-(benzyloxy)-2-(1H-pyrazol-1-yl)pyrimidine-5-carboxylate (2-d)

To a solution of 4-hydroxy-2-(1H-pyrazol-1-yl)pyrimidine-5-carboxylic acid, 2-c, (1 g, 4.85 mmol) in DMF (40 ml) was added K$_2$CO$_3$ (2.34 g, 16.98 mmol) and benzyl bromide (1.83 g, 10.67 mmol). The mixture was heated at 70° C. for 16 hours. The solution was then cooled to room temperature and diluted with water followed by extraction with ethyl acetate. The combined organic layer was washed with water, dried over sodium sulfate and concentrated under vacuum to provide the crude product, 2-d, as a solid (1.2 g).

Step C: 4-(benzyloxy)-2-(1H-pyrazol-1-yl)pyrimidine-5-carboxylic acid (2-e)

To a solution of benzyl 4-(benzyloxy)-2-(1H-pyrazol-1-yl)pyrimidine-5-carboxylate, 2-d, (2 g crude) in EtOH(20 ml)/THF (20 ml)/water (20 ml) was added KOH (0.87 g, 15.5 mmol). The mixture was stirred at room temperature for 12 hours. The mixture was then concentrated under vacuum and the residue was diluted with water and basified to pH=2 with HCl followed by extraction with ethyl acetate. The organic layer was brine washed, dried over sodium sulfate and concentrated under vacuum. The residue was purified on a silica gel column with the eluent of petroleum ether/ethyl acetate=7/1 to afford the compound 2-e (200 mg, 13%).

Step D: 4-(benzyloxy)-2-(1H-pyrazol-1-yl)pyrimidin-5-amine (2-f)

4-(benzyloxy)-2-(1H-pyrazol-1-yl)pyrimidine-5-carboxylic acid, 2-e, (200 mg, 0.68 mmol) was dissolved in THF (20 ml) and treated with Et$_3$N (204 mg, 2.02 mmol) and DPPA (204 mg, 0.74 mmol). The mixture was heated at 66° C. for 12 hours. Then water was added and the resulting mixture was continued to stir at reflux for 2 h. After that the mixture was concentrated under vacuum. The residue was diluted with aq. K$_2$CO$_3$ followed by extraction with ethyl acetate. The organic layer was dried over sodium sulfate and concentrated under vacuum. The residue was purified on silica gel column with the eluent of dichloromethane/methanol=50/1 (Rf=0.7) to provide compound 2-f (72 mg, 40%).

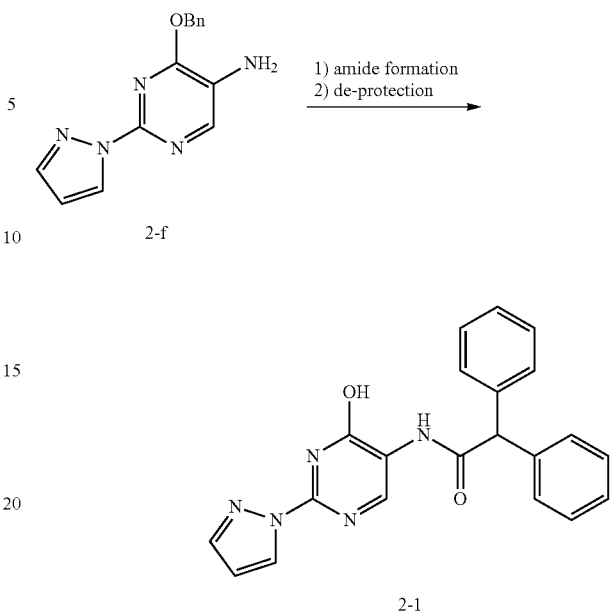

Step E: N-(4-hydroxy-2-(1H-pyrazol-1-yl)pyrimidin-5-yl)-2,2-diphenylacetamide (2-1)

2,2-diphenylacetic acid (110 mg, 0.52 mmol) was dissolved in DMF (10 mL) and EDC (100 mg, 0.52 mmol) and HOBt (70 mg, 0.52 mmol) were added. The mixture was stirred at rt for 5 mins before Et$_3$N (130 mg, 1.3 mmol) and compound 2-f (115 mg, 0.43 mmol) were added. The resulting mixture was stirred at the ambient temperature for 24 h. The resulting mixture was diluted with water followed by extraction with ethyl acetate. The organic layer was washed with brine; dried over sodium sulfate and concentrated under vacuum. The residue was purified on silica gel column with the eluent of ethyl acetate/petroleum ether=1/3 (R$_f$=0.7) to afford an intermediate (80 mg, 40%).

The intermediate, prepared as above, was hydrogenated with hydrogen balloon in methanol (15 mL) and Pd/C (20 mg) at room temperature for 16 hours. The mixture was filtered and the filtrate was concentrated under vacuum. The residue was purified by prep-HPLC to provide the product, 2-1, as a white solid (10 mg). $^1$H NMR (300 MHz, CD$_3$OD): δ 8.78 (s, 1H), 8.48 (d, J=2.4 Hz, 1H), 7.83 (s, 1H), 7.24 (m, 10H), 6.58 (s, 1H), 5.37 (s, 1H). LC-MS: (M+H)$^+$=372.

Intermediate 3-e

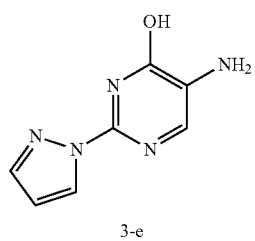

3-e

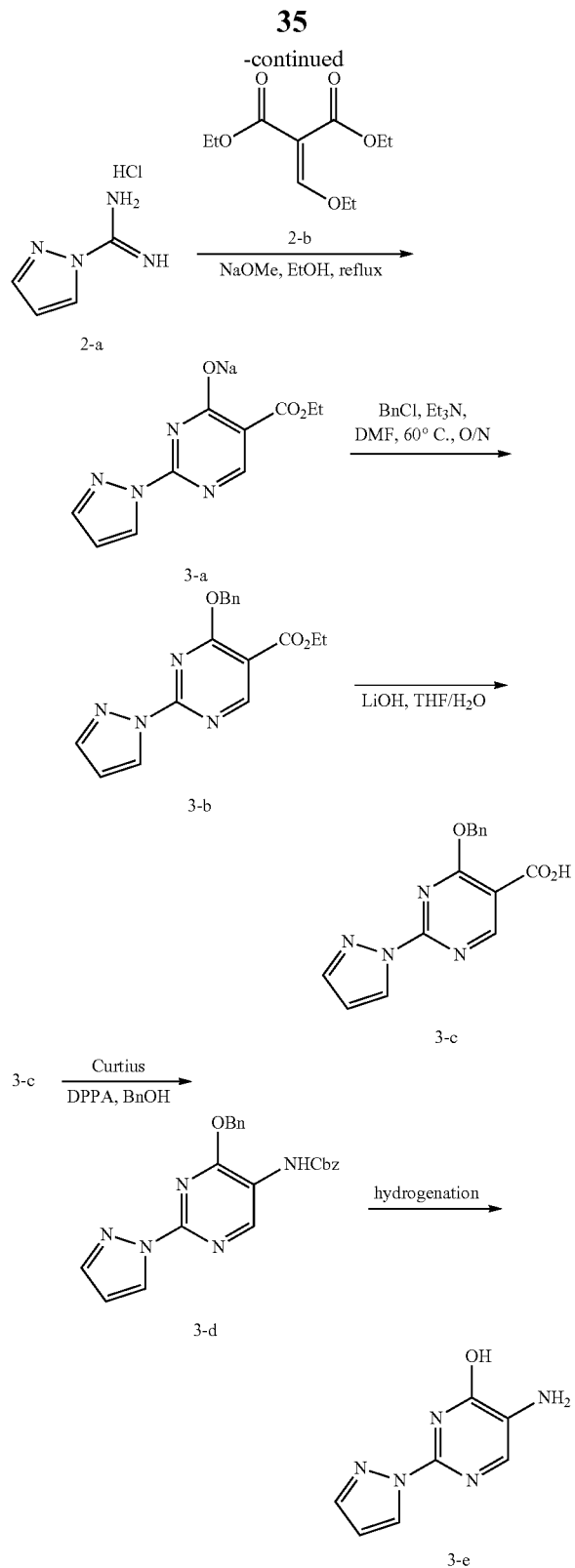

ml) was added sodium methoxide (12.3 g, 0.23 mol) and diethyl ethoxymethylenemalonate, compound 2-b from Example 2, (30 ml, 0.15 mol). The reaction was heated for about 40 min at 75° C. and then cooled to room temperature. The mixture was filtered and the solid was washed with ethanol and ether and dried under vacuum to give compound 3-a (21 g, 60%). $^1$H NMR (DMSO-d6, 300 MHz): δ 8.50 (m, 2H), 7.70 (s, 1H), 6.47 (m, 1H), 4.13 (m, 2H), 1.24 (m, 3H).

Step B: Ethyl 4-(benzyloxy)-2-(1H-pyrazol-1-yl)pyrimidine-5-carboxylate (3-b)

To a solution of ethyl 4-hydroxy-2-(1H-pyrazol-1-yl)pyrimidine-5-carboxylate, 3-a, (0.62 g, 2.7 mmol) in DMF (7 ml) were added benzyl chloride (0.5 g, 3.99 mmol) and Et$_3$N (0.8 g, 7.97 mmol). The resulting mixture was then heated at 60° C. for 12 hours. Then the mixture was cooled to room temperature and diluted with water followed by extraction with ethyl acetate. The organic layer was washed with brine, dried over sodium sulfate and concentrated under vacuum. The residue was purified on silica gel column with the eluent of ethyl acetate/petroleum ether=1/1 (Rf=0.7) to afford the compound, 3-b, (0.36 g, 42%).

Step C: 4-(benzyloxy)-2-(1H-pyrazol-1-yl)pyrimidine-5-carboxylic acid (3-c)

Ethyl 4-(benzyloxy)-2-(1H-pyrazol-1-yl)pyrimidine-5-carboxylate, 3-b, (150 g, 0.46 mol) in THF (1.5 L) was treated with LiOH monohydrate (58 g, 1.39 mol) in water (60 ml) at room temperature for 3 hours. The mixture was concentrated under vacuum and diluted with water (200 ml) followed by extraction with ethyl acetate. The aqueous layer was acidified to pH=2 with 10% HCl and solid crushed out from the solution which was then filtered and washed with water to afford the compound, 3-c. (40 g, 29%).

Step D: Benzyl 4-(benzyloxy)-2-(1H-pyrazol-1-yl)pyrimidin-5-ylcarbamate (3-d)

To a solution of 4-(benzyloxy)-2-(1H-pyrazol-1-yl)pyrimidine-5-carboxylic acid, 3-c, (2 g, 6.76 mmol) in dry THF (40 ml) and toluene (40 ml) were added Et$_3$N (2.04 g, 20.3 mmol), DPPA (2.04 g, 7.43 mmol) and benzyl alcohol (1.1 g, 10.1 mmol). The resulting mixture was heated at 60° C. for 12 hours. The mixture was concentrated under vacuum and the residue was purified on silica gel column with the eluent of ethyl acetate/petroleum ether=1/5 (Rf=0.6) to provide the compound, 3-d (1.96 g, 72.6%). $^1$H NMR (DMSO-d$_6$, 300 MHz): δ 9.39 (br, 1H), 8.73 (s, 1H), 8.62 (s, 1H), 7.83 (s, 1H), 7.56 (m, 2H), 7.33 (m, 8H), 6.57 (m, 1H), 5.58 (s, 2H), 5.16 (s, 2H).

Step E: 5-amino-2-(1H-pyrazol-1-yl)pyrimidin-4-ol (3-e)

Benzyl 4-(benzyloxy)-2-(1H-pyrazol-1-yl)pyrimidin-5-ylcarbamate, 3-d, (1.96 g, 4.9 mmol) was hydrogenated with hydrogen ballon in THF (20 ml) and Pd/C (200 mg) at room temperature for 12 hours. The mixture was filtered through a celite pad and the filtrate was concentrated under vacuum to Step A: Ethyl 4-hydroxy-2-(1H-pyrazol-1-yl)pyrimidine-5-carboxylate (3-a)

1H-pyrazole-1-carboximidamide hydrochloride, compound 2-a from Example 2, (22.11 g, 0.15 mol) in EtOH (250 provide the compound, 3-e (0.8 g, 93%). $^1$H NMR (DMSO-$d_6$, 300 MHz): δ 8.39 (s, 1H), 7.80 (s, 1H), 7.20 (s, 1H), 6.56 (m, 1H), 5.00 (br, 2H).

Example 3

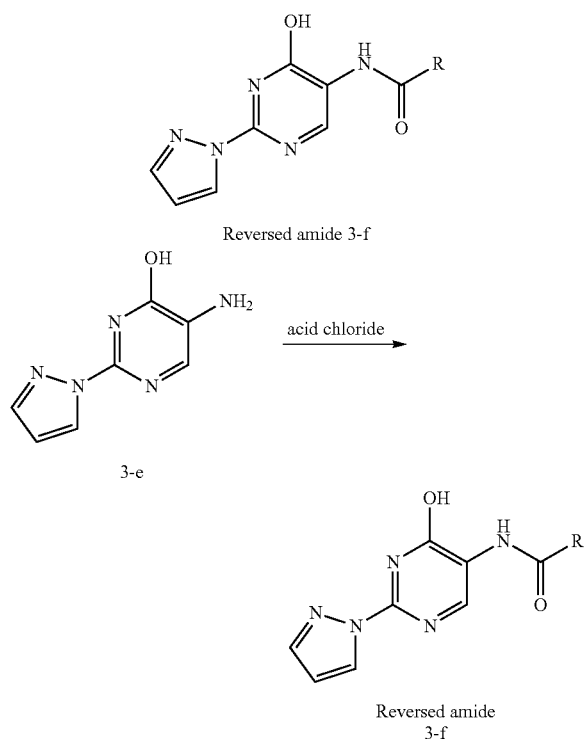

Reversed amide 3-f

Step A: Preparation of Acid Chloride

An appropriate carboxylic acid (commercially available, purchased and used as received, 1 mmol) containing the desired R group of compounds 3-f was heated at reflux in excess thionylchloride for 2 hours. The cooled reaction mixture was concentrated under vacuum and the residue was co-evaporated with anhydrous dichloromethane to give the desired acid chloride.

Step B: Preparation of Amides (Reversed Amide 3-f)

5-amino-2-(1H-pyrazol-1-yl)pyrimidin-4-ol, 3-e, (1 mmol) and $Et_3N$ (2 mmols) were dissolved in dichloromethane (5 ml) and cooled to 0° C. The appropriate concentrated acid chloride (1 mmol) made in Step A was further diluted in dichloromethane (5 ml) to form a mixture. This acid chloride mixture was then added dropwise to the solution containing 3-e and $Et_3N$ to form a reaction mixture. The reaction mixture was allowed to stir at room temperature for additional 3 hours. The reaction mixture was concentrated under vacuum and the residue was taken into THF (10 ml) and treated with 2N lithium hydroxide (10 ml). The mixture was stirred at room temperature for 30 min to 12 hours. For some of the compounds (ca. 20%) a solid precipitated out, thus the solid was collected via filtration to provide the product. For compounds that did not precipitate out, the THF layer was separated and concentrated to afford the crude product, which was further purified by recrystallization using a mixed solvent system of petroleum ether/ethyl acetate/methanol (solvent ratio was optimized for each compound to produce the best crystallization conditions).

Table 1 discloses compounds 3-1 through 3-55 that were made in accordance to the general procedure outlined in Example 3 and by utilizing the appropriate carboxylic acid.

TABLE 1

| Example | Name | $^1$H NMR | Structure |
| --- | --- | --- | --- |
| 3-1 | 2-chloro-N-(4-hydroxy-2-(1H-pyrazol-1-yl)pyrimidin-5-yl)benzamide | $^1$H NMR (DMSO-$d_6$, 300 MHz,): δ 8.94(s, 1H), 8.68(s, 1H), 8.41(s, 1H), 7.48(m, 5H), 6.38(s, 1H). (M + Na)$^+$ = 338 | 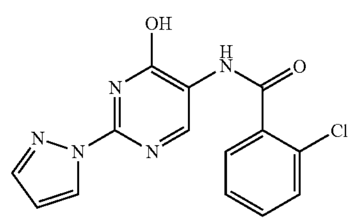 [SMILES: O=C(Nc1cnc(-n2cccn2)nc1O)c1ccccc1Cl] |
| 3-2 | 3-chloro-N-(4-hydroxy-2-(1H-pyrazol-1-yl)pyrimidin-5-yl)benzamide | $^1$H NMR (DMSO-$d_6$, 300 MHz,): δ 9.21(s, 1H), 8.60(s, 1H), 8.40(s, 1H), 7.80(m, 2H), 7.62(m, 3H), 6.38(s, 1H). (M + Na)$^+$ = 338 | 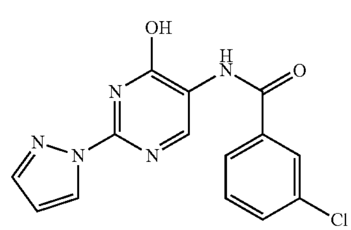 [SMILES: O=C(Nc1cnc(-n2cccn2)nc1O)c1cccc(Cl)c1] |

TABLE 1-continued

| Example | Name | $^1$H NMR |
|---|---|---|
| 3-3 | 4-chloro-N-(4-hydroxy-2-(1H-pyrazol-1-yl)pyrimidin-5-yl)benzamide | $^1$H NMR (DMSO-d$_6$, 300 MHz,): δ 9.20(s, 1H), 8.60(s, 1H), 8.40(s, 1H), 7.90(m, 2H), 7.59(m, 3H), 6.38(s, 1H). (M + Na)$^+$ = 338 |
| 3-4 | 3-(trifluoromethyl)-N-(4-hydroxy-2-(1H-pyrazol-1-yl)pyrimidin-5-yl)benzamide | $^1$H NMR (DMSO-d$_6$, 300 MHz,): δ 9.34(s, 1H), 8.65(s, 1H), 8.42(m, 1H), 8.19(m, 2H), 7.80(m, 1H), 7.70(m, 1H), 7.62(s, 1H), 6.38(s, 1H). (M + Na)$^+$ = 372 |
| 3-5 | 4-(trifluoromethyl)-N-(4-hydroxy-2-(1H-pyrazol-1-yl)pyrimidin-5-yl)benzamide | $^1$H NMR (DMSO-d$_6$, 300 MHz,): δ 13.00(br, 1H), 9.60(br, 1H), 8.50(m, 2H), 8.12(m, 2H), 7.93(m, 3H), 6.68(s, 1H). (M + Na)$^+$ = 372 |
| 3-6 | N-(4-hydroxy-2-(1H-pyrazol-1-yl)pyrimidin-5-yl)-2-(naphthalen-3-yl)acetamide | $^1$H NMR (CD$_3$OD, 300 MHz,): δ 8.85(s, 1H), 8.48(s, 1H), 7.88(m, 4H), 7.60(s, 1H), 7.50(m, 3H), 6.46(s, 1H), 3.97(s, 2H), 1.93(s, 1H),. (M + H)$^+$ = 346.2 |
| 3-7 | 2-cyano-N-(4-hydroxy-2-(1H-pyrazol-1-yl)pyrimidin-5-yl)benzamide | $^1$H NMR (DMSO-d6, 300 MHz,): δ 13.68(br, 1H), 8.45(s, 1H), 8.06(s, 1H), 7.74(s, 1H), 7.66(m, 4H), 6.40(s, 1H). (M + H)$^+$ = 307.1. |
| 3-8 | 3-cyano-N-(4-hydroxy-2-(1H-pyrazol-1-yl)pyrimidin-5-yl)benzamide | $^1$H NMR (DMSO-d6, 300 MHz,): δ 9.28(s, 1H), 8.63(s, 1H), 8.50(s, 1H), 8.40(s, 1H), 8.30(s, 1H), 7.75(s, 1H), 7.61(m, 2H), 6.37(s, 1H). (M + H)$^+$ = 307.1. |

TABLE 1-continued

| Example | Name | ¹H NMR | Structure |
|---|---|---|---|
| 3-9 | 4-cyano-N-(4-hydroxy-2-(1H-pyrazol-1-yl)pyrimidin-5-yl)benzamide | ¹H NMR (DMSO-d6, 300 MHz,): δ 9.31(s, 1H), 8.67(s, 1H), 8.45(s, 1H), 8.00(m, 4H), 7.62(s, 1H), 6.40(s, 1H). (M + Na)⁺ = 329.1. | 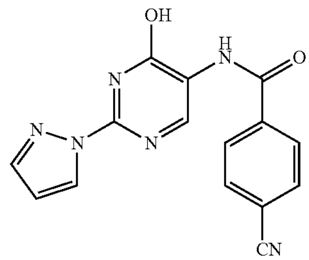 [SMILES: N#Cc1ccc(C(=O)Nc2cnc(-n3cccn3)nc2O)cc1] |
| 3-10 | 2-(trifluoromethyl)-N-(4-hydroxy-2-(1H-pyrazol-1-yl)pyrimidin-5-yl)benzamide | ¹H NMR (DMSO-d6, 300 MHz,): δ 8.88(s, 1H), 8.67(s, 1H), 8.41(s, 1H), 7.65(m, 6H), 6.41(s, 1H). (M + H)⁺ = 350.1. | 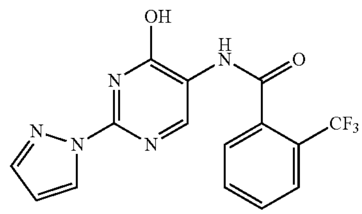 [SMILES: O=C(Nc1cnc(-n2cccn2)nc1O)c1ccccc1C(F)(F)F] |
| 3-11 | N-(4-hydroxy-2-(1H-pyrazol-1-yl)pyrimidin-5-yl)-2-methoxybenzamide | ¹H NMR (DMSO-d6, 300 MHz,): δ 10.57(s, 1H), 8.79(s, 1H), 8.39(s, 1H), 8.00(s, 1H), 7.20(m, 2H), 7.10(m, 2H), 6.38(s, 1H), 4.02(s, 3H). (M + H)⁺ = 312.2. | 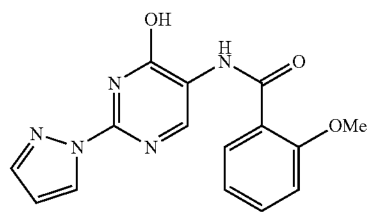 [SMILES: COc1ccccc1C(=O)Nc1cnc(-n2cccn2)nc1O] |
| 3-12 | N-(4-hydroxy-2-(1H-pyrazol-1-yl)pyrimidin-5-yl)-3-methoxybenzamide | ¹H NMR (DMSO-d6, 300 MHz,): δ 9.11(s, 1H), 8.67(s, 1H), 8.40(s, 1H), 7.61(s, 1H), 7.39(m, 3H), 7.15(s, 1H), 6.38(s, 1H), 3.83(s, 3H). (M + H)⁺ = 312.2. | 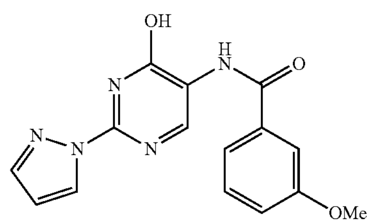 [SMILES: COc1cccc(C(=O)Nc2cnc(-n3cccn3)nc2O)c1] |
| 3-13 | N-(4-hydroxy-2-(1H-pyrazol-1-yl)pyrimidin-5-yl)-4-methoxybenzamide | ¹H NMR (DMSO-d6, 300 MHz,): δ 9.05(s, 1H), 8.65(s, 1H), 8.39(s, 1H), 7.82(m, 2H), 7.59(s, 1H), 7.04(m, 2H), 6.36(s, 1H), 3.82(s, 3H). (M + H)⁺ = 312.1. | 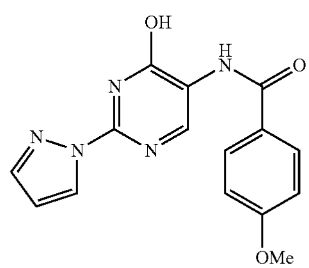 [SMILES: COc1ccc(C(=O)Nc2cnc(-n3cccn3)nc2O)cc1] |
| 3-14 | N-(4-hydroxy-2-(1H-pyrazol-1-yl)pyrimidin-5-yl)-2-(methylsulfonyl)benzamide | ¹H NMR (DMSO-d6, 300 MHz,): δ 8.88(s, 1H), 8.62(s, 1H), 8.39(s, 1H), 8.00(s, 1H), 7.74(m, 3H), 7.60(s, 1H), 6.38(s, 1H), 3.42(s, 3H). (M + H)⁺ = 360.0. | 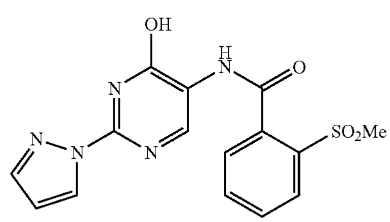 [SMILES: CS(=O)(=O)c1ccccc1C(=O)Nc1cnc(-n2cccn2)nc1O] |

TABLE 1-continued

| Example | Name | ¹H NMR | Structure |
|---|---|---|---|
| 3-15 | N-(4-hydroxy-2-(1H-pyrazol-1-yl)pyrimidin-5-yl)-3-(methylsulfonyl)benzamide | ¹H NMR (DMSO-d6, 300 MHz,): δ 9.42(s, 1H), 8.74(s, 1H), 8.44(m, 2H), 8.20(m, 2H), 7.90(s, 1H), 7.69(s, 1H), 6.46(s, 1H), 3.39(s, 3H). (M + H)⁺ = 359.9. | 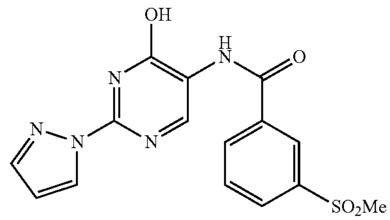 [SMILES: CS(=O)(=O)c1cccc(C(=O)Nc2cnc(-n3cccn3)nc2O)c1] |
| 3-16 | N-(4-hydroxy-2-(1H-pyrazol-1-yl)pyrimidin-5-yl)-4-(methylsulfonyl)benzamide | ¹H NMR (DMSO-d6, 300 MHz,): δ 9.32(s, 1H), 8.70(s, 1H), 8.50(s, 1H), 8.08(m, 4H), 7.63(s, 1H), 6.40(s, 1H), 3.29(s, 3H). (M + H)⁺ = 360.1. | 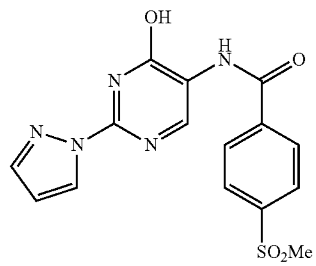 [SMILES: CS(=O)(=O)c1ccc(C(=O)Nc2cnc(-n3cccn3)nc2O)cc1] |
| 3-17 | N-[4-hydroxy-2-(1H-pyrazol-1-yl)pyrimidin-5-yl]biphenyl-2-carboxamide | ¹H NMR (DMSO-d6, 300 MHz,): δ 8.48(s, 1H), 8.32(m, 2H), 7.36(m, 11H), 6.33(s, 1H). (M + H)⁺ = 358.0. | 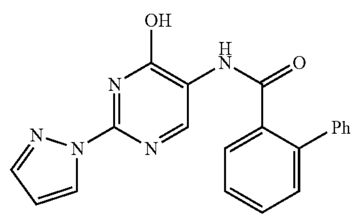 [SMILES: O=C(Nc1cnc(-n2cccn2)nc1O)c1ccccc1-c1ccccc1] |
| 3-18 | N-[4-hydroxy-2-(1H-pyrazol-1-yl)pyrimidin-5-yl]biphenyl-3-carboxamide | ¹H NMR (DMSO-d6, 300 MHz,): δ 9.25(s, 1H), 8.70(s, 1H), 8.40(s, 1H), 8.10(s, 1H), 7.50(m, 9H), 6.38(s, 1H). (M + H)⁺ = 358.0. | 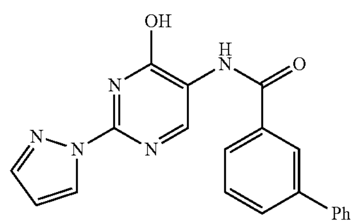 [SMILES: O=C(Nc1cnc(-n2cccn2)nc1O)c1cccc(-c2ccccc2)c1] |
| 3-19 | N-[4-hydroxy-2-(1H-pyrazol-1-yl)pyrimidin-5-yl]biphenyl-4-carboxamide | ¹H NMR (DMSO-d6, 300 MHz,): δ 9.23(s, 1H), 8.72(s, 1H), 8.40(s, 1H), 7.51(m, 10H), 6.40(s, 1H). (M + H)⁺ = 358.1. | 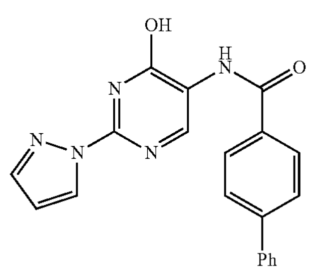 [SMILES: O=C(Nc1cnc(-n2cccn2)nc1O)c1ccc(-c2ccccc2)cc1] |
| 3-20 | N-(4-hydroxy-2-(1H-pyrazol-1-yl)pyrimidin-5-yl)-2-phenoxybenzamide | ¹H NMR (DMSO-d6, 300 MHz,): δ 10.27(s, 1H), 8.73(s, 1H), 8.30(s, 1H), 8.06(s, 1H), 7.13(m, 9H), 6.34(s, 1H). (M + H)⁺ = 374.0. | 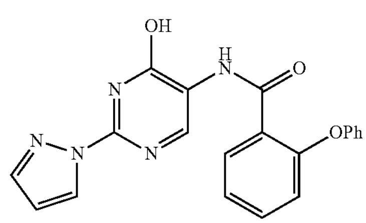 [SMILES: O=C(Nc1cnc(-n2cccn2)nc1O)c1ccccc1Oc1ccccc1] |

TABLE 1-continued

| Example | Name | $^1$H NMR | Structure |
|---|---|---|---|
| 3-21 | N-(4-hydroxy-2-(1H-pyrazol-1-yl)pyrimidin-5-yl)-3-phenoxybenzamide | $^1$H NMR (DMSO-d6, 300 MHz,): δ 9.14(s, 1H), 8.62(s, 1H), 8.39(s, 1H), 7.07(m, 10H), 6.37(s, 1H). (M + H)$^+$ = 373.9. | 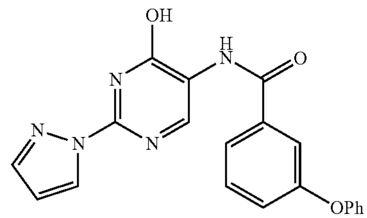 [SMILES: O=C(Nc1cnc(-n2cccn2)nc1O)c1cccc(Oc2ccccc2)c1] |
| 3-22 | N-(4-hydroxy-2-(1H-pyrazol-1-yl)pyrimidin-5-yl)-4-phenoxybenzamide | $^1$H NMR (DMSO-d6, 300 MHz,): δ 9.11(s, 1H), 8.70(s, 1H), 8.40(s, 1H), 7.90(m, 2H), 7.60(s, 1H), 7.40(m, 2H), 7.08(m, 5H), 6.38(s, 1H). (M + H)$^+$ = 374.1. | 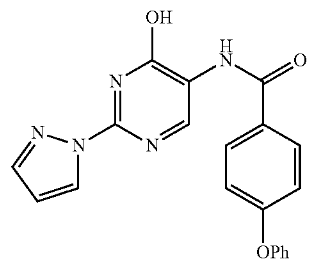 [SMILES: O=C(Nc1cnc(-n2cccn2)nc1O)c1ccc(Oc2ccccc2)cc1] |
| 3-23 | 2-(2-chlorophenyl)-N-(4-hydroxy-2-(1H-pyrazol-1-yl)pyrimidin-5-yl)acetamide | $^1$H NMR (DMSO-d6, 300 MHz,): δ 8.76(s, 1H), 8.55(s, 1H), 8.38(s, 1H), 7.60(s, 1H), 7.45(m, 2H), 7.33(m, 2H), 6.37(s, 1H), 3.90(s, 2H). (M + H)$^+$ = 330.0. | 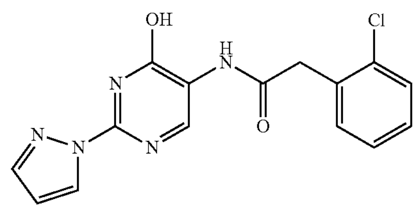 [SMILES: O=C(Cc1ccccc1Cl)Nc1cnc(-n2cccn2)nc1O] |
| 3-24 | 2-(3-chlorophenyl)-N-(4-hydroxy-2-(1H-pyrazol-1-yl)pyrimidin-5-yl)acetamide | $^1$H NMR (DMSO-d6, 300 MHz,): δ 8.94(s, 1H), 8.54(s, 1H), 8.40(s, 1H), 7.50(s, 1H), 7.31(m, 4H), 6.35(s, 1H), 3.76(s, 2H). (M + H)$^+$ = 330.1. | 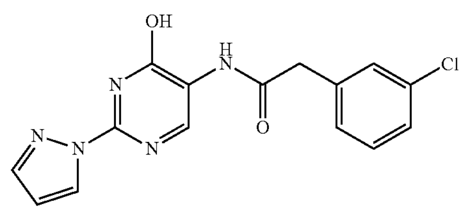 [SMILES: O=C(Cc1cccc(Cl)c1)Nc1cnc(-n2cccn2)nc1O] |
| 3-25 | 2-(4-chlorophenyl)-N-(4-hydroxy-2-(1H-pyrazol-1-yl)pyrimidin-5-yl)acetamide | $^1$H NMR (DMSO-d6, 300 MHz,): δ 8.84(s, 1H), 8.55(s, 1H), 8.38(s, 1H), 7.58(s, 1H), 7.38(m, 4H), 6.35(s, 1H), 3.75(s, 2H). (M + H)$^+$ = 330.1. | 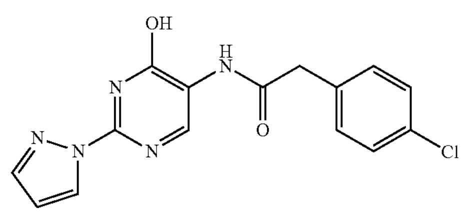 [SMILES: O=C(Cc1ccc(Cl)cc1)Nc1cnc(-n2cccn2)nc1O] |
| 3-26 | 2-(3-cyanophenyl)-N-(4-hydroxy-2-(1H-pyrazol-1-yl)pyrimidin-5-yl)acetamide | $^1$H NMR (DMSO-d6, 300 MHz,): δ 9.72(s, 1H), 8.51(m, 2H), 7.96(s, 1H), 7.53(m, 4H), 6.65(s, 1H), 3.91(s, 2H). (M + H)$^+$ = 321.0. | 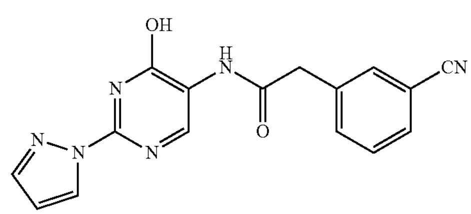 [SMILES: N#Cc1cccc(CC(=O)Nc2cnc(-n3cccn3)nc2O)c1] |
| 3-27 | 2-(2-(trifluoromethyl)phenyl)-N-(4-hydroxy-2-(1H-pyrazol-1-yl)pyrimidin-5-yl)acetamide | $^1$H NMR (DMSO-d6, 300 MHz,): δ 8.81(s, 1H), 8.50(s, 1H), 8.40(s, 1H), 7.55(m, 5H), 6.34(s, 1H), 3.96(s, 2H). (M + H)$^+$ = 364.0. | 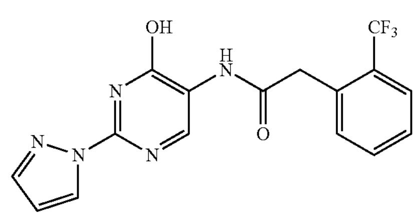 |

TABLE 1-continued

| Example | Name | $^1$H NMR | Structure |
|---|---|---|---|
| 3-28 | 2-(3-(trifluoromethyl)phenyl)-N-(4-hydroxy-2-(1H-pyrazol-1-yl)pyrimidin-5-yl)acetamide | $^1$H NMR (DMSO-d6, 300 MHz,): δ 9.02(s, 1H), 8.56(s, 1H), 8.40(s, 1H), 7.58(m, 5H), 6.36(s, 1H), 3.88(s, 2H). (M + H)$^+$ = 364.0. | 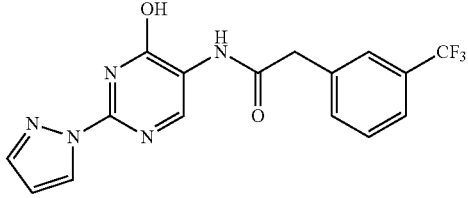 [SMILES: O=C(Cc1cccc(C(F)(F)F)c1)Nc1cnc(-n2cccn2)nc1O] |
| 3-29 | 2-(4-(trifluoromethyl)phenyl)-N-(4-hydroxy-2-(1H-pyrazol-1-yl)pyrimidin-5-yl)acetamide | $^1$H NMR (DMSO-d6, 300 MHz,): δ 12.96(br, 1H), 9.69(s, 1H), 8.52(m, 2H), 7.69(s, 1H), 7.58(m, 4H), 6.58(s, 1H), 3.95(s, 2H). (M + H)$^+$ = 364.2. | 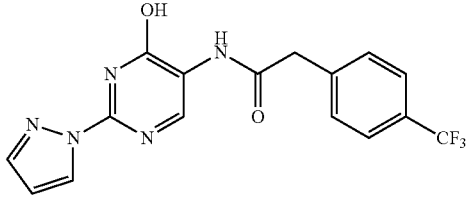 [SMILES: O=C(Cc1ccc(C(F)(F)F)cc1)Nc1cnc(-n2cccn2)nc1O] |
| 3-30 | N-(4-hydroxy-2-(1H-pyrazol-1-yl)pyrimidin-5-yl)-2-(2-methoxyphenyl)acetamide | $^1$H NMR (DMSO-d6, 300 MHz,): δ 12.82(br, 1H), 9.23(s, 1H), 8.51(s, 2H), 7.96(s, 1H), 7.19(m, 2H), 6.96(m, 2H), 6.64(s, 1H), 3.78(s, 5H). (M + H)$^+$ = 326.0. | 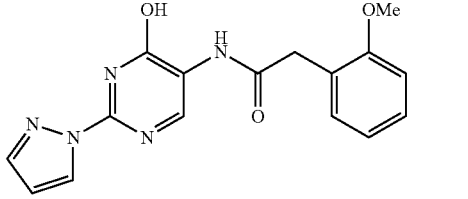 [SMILES: COc1ccccc1CC(=O)Nc1cnc(-n2cccn2)nc1O] |
| 3-31 | N-(4-hydroxy-2-(1H-pyrazol-1-yl)pyrimidin-5-yl)-2-(3-methoxyphenyl)acetamide | $^1$H NMR (DMSO-d6, 300 MHz,): δ 12.71(br, 1H), 9.50(s, 1H), 8.50(m, 2H), 7.97(s, 1H), 7.19(s, 1H), 6.81(m, 3H), 6.64(s, 1H), 3.77(s, 5H). (M + H)$^+$ = 326.1. | 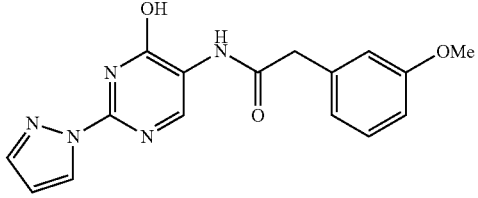 [SMILES: COc1cccc(CC(=O)Nc2cnc(-n3cccn3)nc2O)c1] |
| 3-32 | N-(4-hydroxy-2-(1H-pyrazol-1-yl)pyrimidin-5-yl)-2-(4-methoxyphenyl)acetamide | $^1$H NMR (DMSO-d6, 300 MHz,): δ 8.70(s, 1H), 8.55(s, 1H), 834(s, 1H), 7.57(s, 1H), 7.30(m, 2H), 6.88(m, 2H), 6.35(s, 1H), 3.72(s, 3H), 3.62(s, 2H). (M + H)$^+$ = 326.1. | 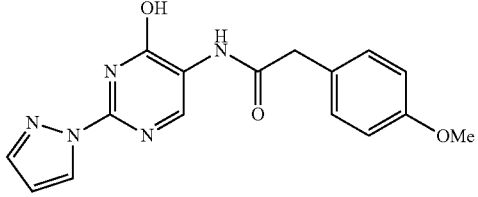 [SMILES: COc1ccc(CC(=O)Nc2cnc(-n3cccn3)nc2O)cc1] |
| 3-33 | N-(4-hydroxy-2-(1H-pyrazol-1-yl)pyrimidin-5-yl)-2-phenylpropanamide | $^1$H NMR (DMSO-d6, 300 MHz,): δ 8.69(s, 1H), 8.57(s, 1H), 8.35(s, 1H), 7.58(s, 1H), 7.32(m, 5H), 6.35(s, 1H), 4.02(m, 1H), 1.38(d, J = 6 Hz, 3H). (M + H)$^+$ = 310.0. | 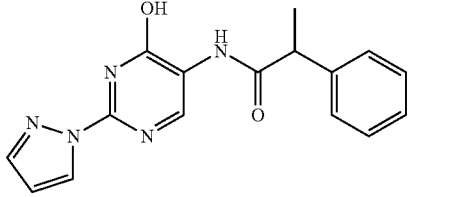 [SMILES: CC(C(=O)Nc1cnc(-n2cccn2)nc1O)c1ccccc1] |
| 3-34 | N-(4-hydroxy-2-(1H-pyrazol-1-yl)pyrimidin-5-yl)-2-phenylbutanamide | $^1$H NMR (DMSO-d6, 300 MHz,): δ 8.74(s, 1H), 8.58(s, 1H), 8.35(s, 1H), 7.58(s, 1H), 7.29(m, 5H), 6.34(s, 1H), 3.77(m, 1H), 2.00(m, 1H), 1.60(m, 1H), 0.82(m, 3H). (M + H)$^+$ = 324.0. | 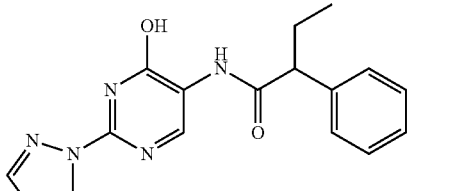 |

TABLE 1-continued

| Example | Name | ¹H NMR | Structure |
|---|---|---|---|
| 3-35 | N-(4-hydroxy-2-(1H-pyrazol-1-yl)pyrimidin-5-yl)-3-methyl-2-phenylbutanamide | ¹H NMR (DMSO-d6, 300 MHz,): δ 8.79(s, 1H), 8.57(s, 1H), 8.34(s, 1H), 7.58(s, 1H), 7.28(m, 5H), 6.35(s, 1H), 3.51(d, J = 9 Hz, 1H), 2.20(m, 1H), 0.96(d, J = 9 Hz, 3H), 0.61(d, J = 6 Hz, 3H). (M + H)⁺ = 338.1. | 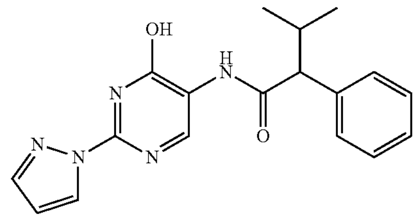 [SMILES: CC(C)C(C(=O)Nc1cnc(-n2cccn2)nc1O)c1ccccc1] |
| 3-36 | N-(4-hydroxy-2-(1H-pyrazol-1-yl)pyrimidin-5-yl)-3-methyl-2-phenylpentanamide | ¹H NMR (DMSO-d6, 300 MHz,): δ 8.79(s, 1H), 8.56(s, 1H), 8.33(s, 1H), 7.56(s, 1H), 7.40(m, 2H), 7.25(m, 3H), 6.33(s, 1H), 3.58(m, 1H), 2.13(m, 1H), 1.51(m, 1H), 1.10(m, 1H), 0.89(m, 3H), 0.59(m, 1H). (M + H)⁺ = 352.0. | 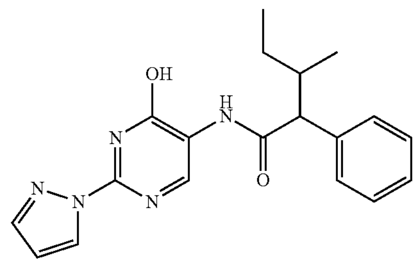 [SMILES: CCC(C)C(C(=O)Nc1cnc(-n2cccn2)nc1O)c1ccccc1] |
| 3-37 | N-(4-hydroxy-2-(1H-pyrazol-1-yl)pyrimidin-5-yl)-2-methyl-2-phenylpropanamide | ¹H NMR (DMSO-d6, 300 MHz,): δ 8.55(s, 1H), 8.32(s, 1H), 8.18(s, 1H), 7.56(s, 1H), 7.35(m, 5H), 6.33(s, 1H), 1.55(s, 6H). (M + H)⁺ = 324.0. | 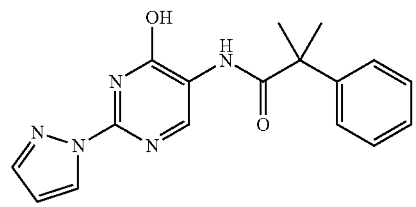 [SMILES: CC(C)(C(=O)Nc1cnc(-n2cccn2)nc1O)c1ccccc1] |
| 3-38 | N-(4-hydroxy-2-(1H-pyrazol-1-yl)pyrimidin-5-yl)-1-phenylcyclopropanecarboxamide | ¹H NMR (DMSO-d6, 300 MHz,): δ 8.54(s, 1H), 8.32(s, 1H), 8.11(s, 1H), 7.56(s, 1H), 7.39(m, 5H), 6.33(s, 1H), 1.46(s, 2H), 1.05(s, 2H). (M + H)⁺ = 322.0. | 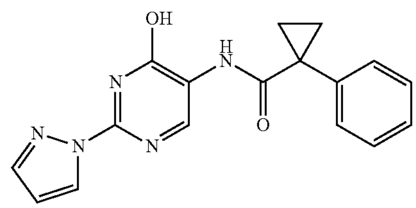 [SMILES: O=C(Nc1cnc(-n2cccn2)nc1O)C1(c2ccccc2)CC1] |
| 3-39 | N-(4-hydroxy-2-(1H-pyrazol-1-yl)pyrimidin-5-yl)-2-(naphthalen-1-yl)acetamide | ¹H NMR (DMSO-d6, 300 MHz,): δ 9.59(s, 1H), 8.50(m, 2H), 8.10(m, 1H), 7.80(m, 3H), 7.48(m, 5H), 6.62(s, 1H), 4.31(s, 2H). (M + H)⁺ = 345.9. | 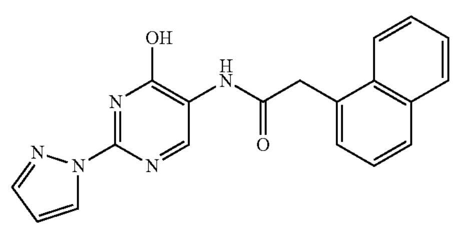 [SMILES: O=C(Cc1cccc2ccccc12)Nc1cnc(-n2cccn2)nc1O] |
| 3-40 | 2-(benzo[d][1,3]dioxol-5-yl)-N-(4-hydroxy-2-(1H-pyrazol-1-yl)pyrimidin-5-yl)acetamide | ¹H NMR (DMSO-d6, 300 MHz,): δ 8.80(s, 1H), 8.59(s, 1H), 8.40(s, 1H), 7.63(s, 1H), 6.90(m, 3H), 6.40(s, 1H), 6.04(s, 2H), 3.67(s, 2H). (M + H)⁺ = 339.8. | 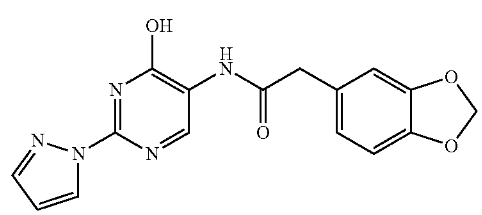 [SMILES: O=C(Cc1ccc2c(c1)OCO2)Nc1cnc(-n2cccn2)nc1O] |
| 3-41 | N-(4-hydroxy-2-(1H-pyrazol-1-yl)pyrimidin-5-yl)-2-(pyridin-4-yl)acetamide | ¹H NMR (DMSO-d6, 300 MHz,): δ 12.90(br, 1H), 9.75(s, 1H), 8.47(m, 4H), 7.95(s, 1H), 7.30(d, J = 6 Hz, 2H), 6.63(s, 1H), 3.87(s, 2H). (M + H)⁺ = 297.1. | 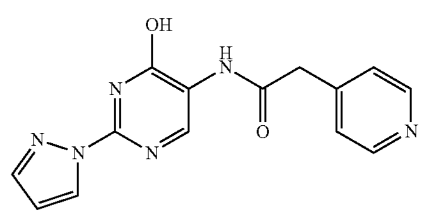 [SMILES: O=C(Cc1ccncc1)Nc1cnc(-n2cccn2)nc1O] |

TABLE 1-continued

| Example | Name | ¹H NMR | Structure |
|---|---|---|---|
| 3-42 | 2-(biphenyl-4-yl)-N-(4-hydroxy-2-(1H-pyrazol-1-yl)pyrimidin-5-yl)acetamide | H NMR (DMSO-d6, 300 MHz,): δ 8.94(s, 1H), 8.61(s, 1H), 8.40(s, 1H), 7.66(m, 6H), 7.50(m, 6H), 6.42(s, 1H), 3.83(s, 2H). (M + H)⁺ = 371.9. | 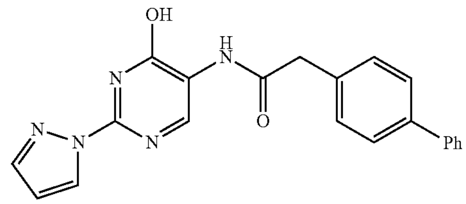 [SMILES: O=C(Cc1ccc(-c2ccccc2)cc1)Nc1cnc(-n2cccn2)nc1O] |
| 3-43 | N-(4-hydroxy-2-(1H-pyrazol-1-yl)pyrimidin-5-yl)heptanamide | ¹H NMR (DMSO-d6, 300 MHz,): δ 8.56(d, 2H), 8.36(q, 1H), 7.59(s, 1H), 6.36(s, 1H), 3.33(s, 1H), 2.49(t, 2H), 1.54(t, 2H), 1.26(m, 6H), 0.86(t, 3H). (M + H)⁺ = 290.0. | 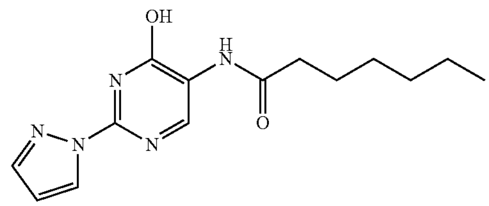 [SMILES: CCCCCCC(=O)Nc1cnc(-n2cccn2)nc1O] |
| 3-44 | N-(4-hydroxy-2-(1H-pyrazol-1-yl)pyrimidin-5-yl)-3-phenylpropanamide | ¹H NMR (DMSO-d6, 300 MHz,): δ 8.71(s, 1H), 8.58(s, 1H), 8.36(d, 1H), 7.59(s, 1H), 7.24(m, 5H), 6.36(s, 1H), 2.68(t, 2H), 2.49(t, 2H). (M + H)⁺ = 310.0. | 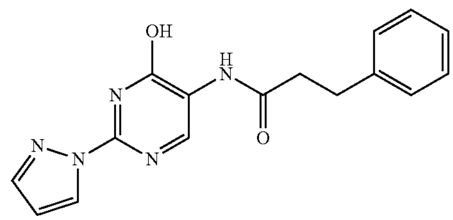 [SMILES: O=C(CCc1ccccc1)Nc1cnc(-n2cccn2)nc1O] |
| 3-45 | N-(4-hydroxy-2-(1H-pyrazol-1-yl)pyrimidin-5-yl)-4-phenylbutanamide | ¹H NMR (DMSO-d6, 300 MHz,): δ 8.55(d, 2H), 8.35(d, 1H), 7.58(s, 1H), 7.21(m, 5H), 6.34(s, 1H), 2.99(t, 2H), 2.36(t, 2H), 1.82(m, 2H). (M + H)⁺ = 324.0. | 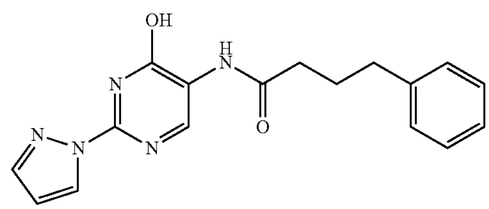 [SMILES: O=C(CCCc1ccccc1)Nc1cnc(-n2cccn2)nc1O] |
| 3-46 | N-(4-hydroxy-2-(1H-pyrazol-1-yl)pyrimidin-5-yl)cyclohexanecarboxaide | ¹H NMR (DMSO-d6, 300 MHz,): δ 8.51(d, 2H), 8.36(d, 2H), 7.59(s, 1H), 6.37(s, 1H), 2.41(m, 1H), 1.69(m, 5H), 1.28(m, 5H). (M + H)⁺ = 288.0. | 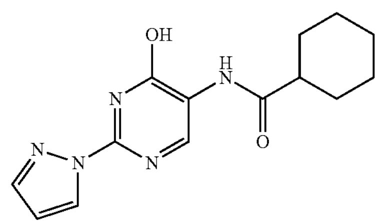 [SMILES: O=C(Nc1cnc(-n2cccn2)nc1O)C1CCCCC1] |
| 3-47 | tert-butyl4-(4-hydroxy-2-(1H-pyrazol-1-yl)pyrimidin-5-ylcarbamoyl)piperidine-1-carboxylate | ¹H NMR (DMSO-d6, 300 MHz,): δ 12.75(s, 1H), 9.37(s, 1H), 8.52(s, 1H), 7.97(s, 1H), 6.64(m, 3H), 3.93(d, 2H), 2.69(m, 3H), 1.70(d, 2H), 1.38(s, 10H). (M + Na)⁺ = 411.0. | 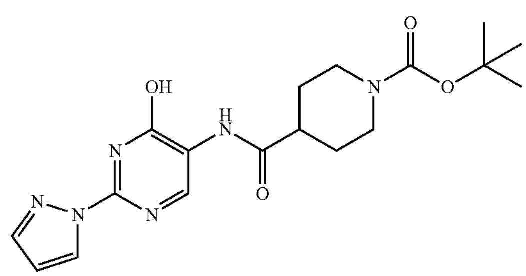 [SMILES: CC(C)(C)OC(=O)N1CCC(C(=O)Nc2cnc(-n3cccn3)nc2O)CC1] |
| 3-48 | 2-cyclohexyl-N-(4-hydroxy-2-(1H-pyrazol-1-yl)pyrimidin-5-yl)acetamide | ¹H NMR (DMSO-d6, 300 MHz,): δ 12.73(s, 1H), 9.25(s, 1H), 8.52(d, 2H), 7.97(s, 1H), 6.65(s, 1H), 2.32(d, 2H), 1.62(m, 7H), 1.15(m, 6H). (M + H)⁺ = 302.2. | 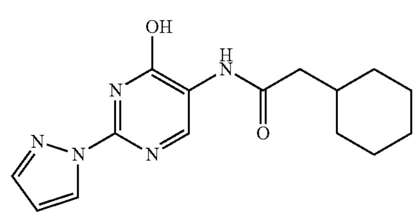 [SMILES: O=C(CC1CCCCC1)Nc1cnc(-n2cccn2)nc1O] |

TABLE 1-continued

| Example | Name | ¹H NMR | Structure |
|---------|------|--------|-----------|
| 3-49 | tert-butyl3-(4-hydroxy-2-(1H-pyrazol-1-yl)pyrimidin-5-ylcarbamoyl)piperidine-1-carboxylate | ¹H NMR (DMSO-d6, 300 MHz,): δ 10.57(s, 1H), 8.91(s, 1H), 8.37(d, 1H), 8.02(s, 1H), 7.72(s, 1H), 6.51(s, 1H), 4.02(m, 2H), 2.78(m, 2H), 2.47(s, 1H), 2.03(m, 1H), 1.45(m, 12H). (M + H)⁺ = 389.2. | 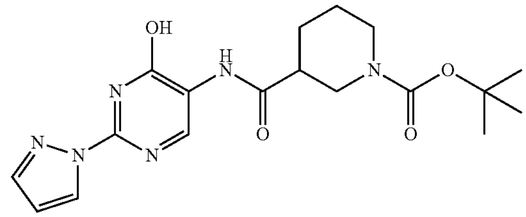 [SMILES: CC(C)(C)OC(=O)N1CCCC(C(=O)Nc2cnc(-n3cccn3)nc2O)C1] |
| 3-50 | tert-butyl4-((4-hydroxy-2-(1H-pyrazol-1-yl) pyrimidin-5-ylcarbamoyl)methyl)piperidine-1-carboxylate | ¹H NMR (DMSO-d6, 300 MHz,): δ 12.89(s, 1H), 9.33(s, 1H), 8.50(d, 2H), 7.95(s, 1H), 6.63(s, 1H), 3.85(d, 2H), 2.62(s, 2H), 2.48(d, 2H), 1.72(s, 1H), 1.37(m, 9H), 1.04(m, 2H). (M + Na)⁺ = 425.0. | 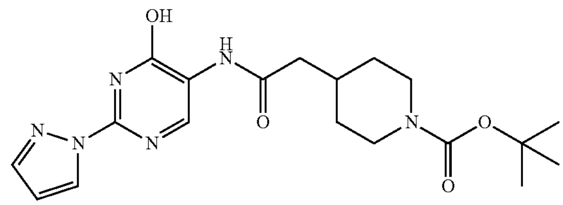 [SMILES: CC(C)(C)OC(=O)N1CCC(CC(=O)Nc2cnc(-n3cccn3)nc2O)CC1] |
| 3-51 | tert-butyl3-(4-hydroxy-2-(1H-pyrazol-1-yl)pyrimidin-5-ylcarbamoyl)pyrrolidine-1-carboxylate | ¹H NMR (DMSO-d6, 300 MHz,): δ 12.92(s, 1H), 9.55(s, 1H), 8.51(d, 2H), 7.95(s, 1H), 6.63(s, 1H), 3.28(m, 7H), 1.92(m, 2H), 1.38(s, 9H). (M + Na)⁺ = 397.0. | 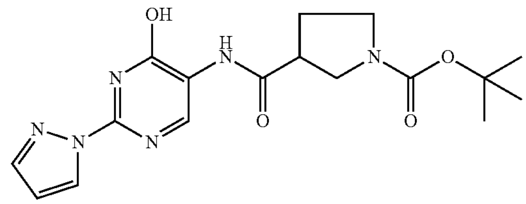 [SMILES: CC(C)(C)OC(=O)N1CCC(C(=O)Nc2cnc(-n3cccn3)nc2O)C1] |
| 3-52 | 1,2,3,4-tetrahydro-N-(4-hydroxy-2-(1H-pyrazol-1-yl)pyrimidin-5-yl)naphthalene-1-carboxamide | ¹H NMR (DMSO-d6, 300 MHz,): δ 8.56(m, 2H), 8.36(s, 1H), 7.58(s, 1H), 7.10(s, 4H), 6.35(s, 1H), 3.98(s, 1H), 2.75(s, 2H), 1.67(m, 4H). (M + H)⁺ = 336.1. | 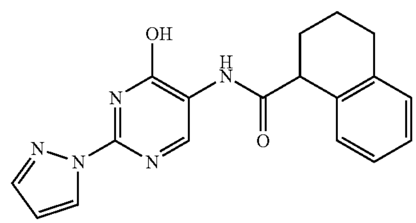 [SMILES: O=C(Nc1cnc(-n2cccn2)nc1O)C1CCCc2ccccc21] |
| 3-53 | 2,3-dihydro-N-(4-hydroxy-2-(1H-pyrazol-1-yl)pyrimidin-5-yl)-1H-indene-1-carboxamide | ¹H NMR (DMSO-d6, 300 MHz,): δ 8.90(s, 1H), 8.53(s, 1H), 8.36(s, 1H), 7.57(s, 1H), 7.15(m, 4H), 635(s, 1H), 4.26(t, 1H), 2.82(m, 2H), 2.26(m, 2H). | 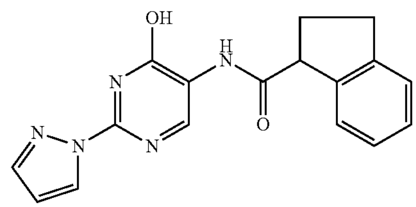 [SMILES: O=C(Nc1cnc(-n2cccn2)nc1O)C1CCc2ccccc21] |
| 3-54 | 1,2,3,4-tetrahydro-N-(4-hydroxy-2-(1H-pyrazol-1-yl)pyrimidin-5-yl)naphthalene-2-carboxamide | ¹H NMR (DMSO-d6, 300 MHz,): δ 8.75(s, 1H), 8.60(s, 1H), 8.36(s, 1H), 7.58(s, 1H), 7.07(s, 4H), 6.36(s, 1H), 2.68(m, 6H), 1.72(s, 1H), 1.62(s, 1H). (M + H)⁺ = 336.2. | 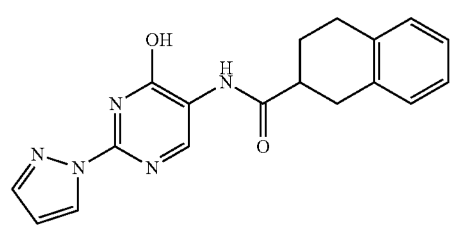 [SMILES: O=C(Nc1cnc(-n2cccn2)nc1O)C1CCc2ccccc2C1] |
| 3-55 | 2,3-dihydro-N-(4-hydroxy-2-(1H-pyrazol-1-yl)pyrimidin-5-yl)-1H-indene-2-carboxamide | ¹H NMR (DMSO-d6, 300 MHz,): δ 8.82(s, 1H), 8.59(s, 1H), 8.38(s, 1H), 7.59(s, 1H), 7.13(m, 4H), 6.37(s, 1H), 3.56(m, 1H), 3.10(m, 4H). (M + H)⁺ = 322.1. | 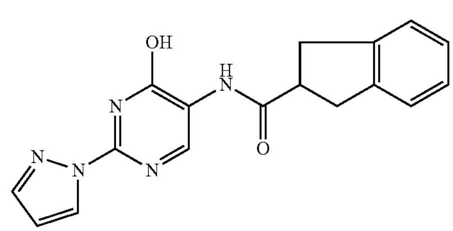 [SMILES: O=C(Nc1cnc(-n2cccn2)nc1O)C1Cc2ccccc2C1] |

Example 4

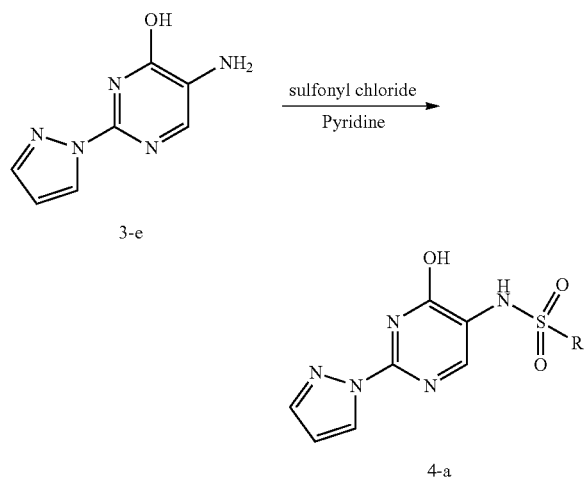

General Procedure for Compound 4-a 5-amino-2-(1H-pyrazol-1-yl) (1.44 mmol) (3-e) was dissolved pyridine(5 ml) and cooled to 0° C. Sulfonyl chloride (1.58 mmol) was added dropwise. The resulting mixture was allowed to stir at room temperature for additional 3 hours. The mixture was concentrated under vacuum and the residue was diluted with formic acid (10 ml) and water (10 ml). A solid precipitated out of solution. The solid was then filtered out of solution. The crude solid was recrystallized (methanol, ethyl acetate or tetrafuran) to provide the product.

Compounds 4-1 through 4-4 were prepared in a manner similar to that described in the general procedure of Example 4-a by substituting the appropriate R group. Table 2 shows compounds 4-1 through 4-4.

TABLE 2

| Example | Name | $^1$H NMR | Structure |
|---|---|---|---|
| 4-1 | 4-chloro-N-[4-hydroxy-2-(1H-pyrazol-1-yl)pyrimidin-5-yl]benzenesulfonamide | $^1$H NMR (DMSO-$d_6$, 300 MHz,): δ 13.05(br, 1H), 9.90(s, 1H), 8.47(s, 1H), 7.62(m, 6H), 6.61(s, 1H). $(M + H)^+$ = 352.1. | 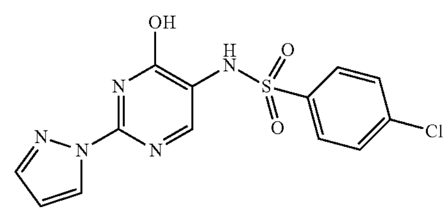 [SMILES: O=S(=O)(Nc1cnc(-n2cccn2)nc1O)c1ccc(Cl)cc1] |
| 4-2 | 1-(4-chlorophenyl)-N-[4-hydroxy-2-(1H-pyrazol-1-yl)pyrimidin-5-yl]methanesulfonamide | $^1$H NMR (DMSO-$d_6$, 300 MHz,): δ 13.20(br, 1H), 9.13(br, 1H), 8.52(s, 1H), 7.95(s, 1H), 7.41(m, 4H), 6.65(s, 1H), 4.58(s, 2H). $(M + H)^+$ = 366.1. | 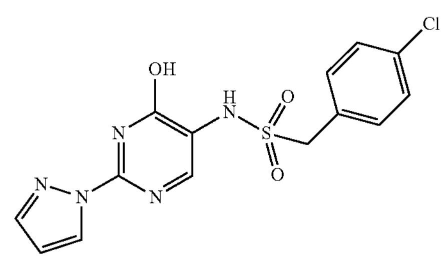 [SMILES: O=S(=O)(Cc1ccc(Cl)cc1)Nc1cnc(-n2cccn2)nc1O] |
| 4-3 | 3-chloro-N-[4-hydroxy-2-(1H-pyrazol-1-yl)pyrimidin-5-yl]benzenesulfonamide | $^1$H NMR (DMSO-$d_6$, 300 MHz,): δ 13.05(br, 1H), 10.01(br, 1H), 8.47(s, 1H), 7.71(m, 5H), 6.62(s, 1H). $(M + Na)^+$ = 374.0. | 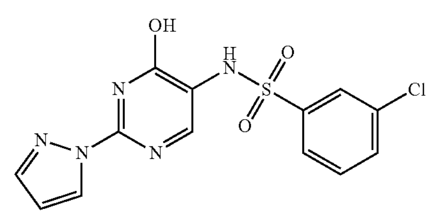 [SMILES: O=S(=O)(Nc1cnc(-n2cccn2)nc1O)c1cccc(Cl)c1] |
| 4-4 | N-[4-hydroxy-2-(1H-pyrazol-1-yl)pyrimidin-5-yl]-1-[4-(trifluoromethyl)phenyl]methanesulfonamide | $^1$H NMR (DMSO-$d_6$, 300 MHz,): δ 13.24(br, 1H), 9.21(br, 1H), 8.51(s, 1H), 7.65(m, 6H), 6.65(s, 1H), 4.70(s, 2H). $(M + H)^+$ = 400.1. | 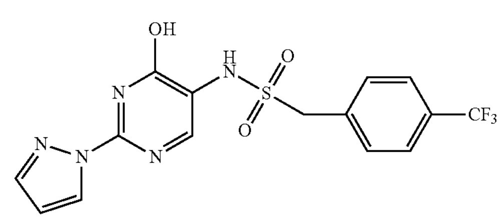 [SMILES: O=S(=O)(Cc1ccc(C(F)(F)F)cc1)Nc1cnc(-n2cccn2)nc1O] |

Example 5

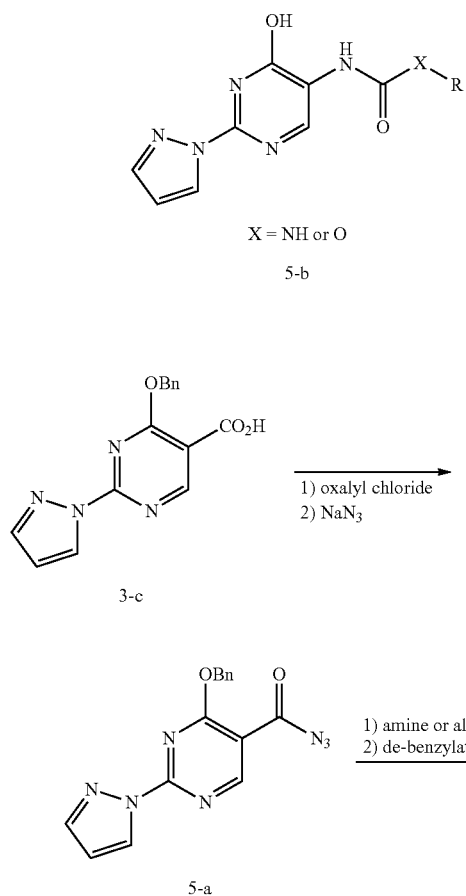

Step A: Azido(4-(benzyloxy)-2-(1H-pyrazol-1-yl)pyrimidin-5-yl)methanone (5-a)

4-(benzyloxy)-2-(1H-pyrazol-1-yl)pyrimidine-5-carboxylic acid (3-c) was synthesized in a manner outlined in Steps A through Step C of the synthesis of Intermediate 3-e. To a solution of 4-(benzyloxy)-2-(1H-pyrazol-1-yl)pyrimidine-5-carboxylic acid, 3-c, (500 mg, 1.69 mmol) in dry dichloromethane (10 ml) was added dropwise oxalyl chloride (0.29 ml, 3.38 mmol) at 0° C. and a catalytic amount of DMF (3-5 drops). The mixture was stirred at room temperature for 3 hours. Then the mixture was concentrated under vacuum and the residue was dissolved in acetone (10 ml). Et$_3$N (205 mg, 2.03 mmol) was added at 0° C. and the mixture was stirred for 5 mins before sodium azide (988 mg, 15.2 mmol) in water (1 ml) was added. The resulting mixture was stirred at room temperature for 1 h. Subsequently, the mixture was diluted with water and filtered. The solid was washed with water (5-10 mL) and then taken into approximately 20-30 mL of dichloromethane. The organic layer was dried over sodium sulfate and concentrated under vacuum to provide compound 5-a as a solid (130 mg) which was used in Step B without any further purification. (M+H)$^+$=322.

Step B: The Synthesis of the Carbamate/Urea (5-b)

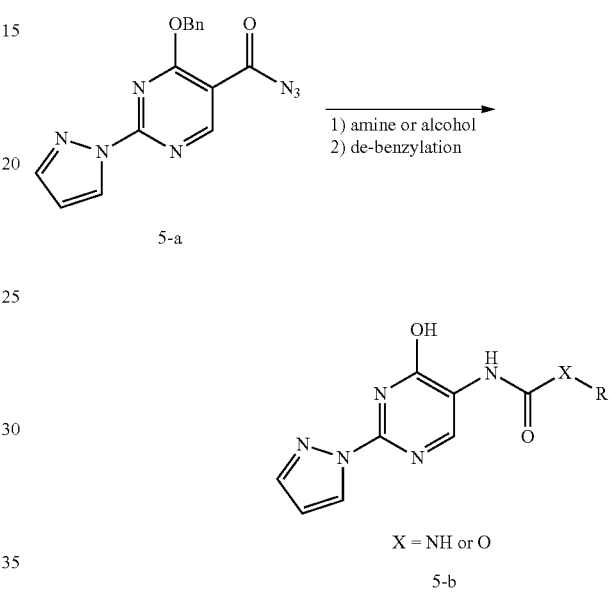

Step B(1): Curtis Rearrangement

To a solution of azido(4-(benzyloxy)-2-(1H-pyrazol-1-yl)pyrimidin-5-yl)methanone, 5-a, (1 mmol) in anhydrous toluene (10 ml) was added the appropriate amine or alcohol (purchased and used as received, 1.2 mmol). The resulting mixture was heated at reflux under nitrogen 5 hours. The mixture was concentrated under vacuum and the residue was purified on silica gel column with the eluent of ethyl acetate/petroleum ether=1/2, v/v, (Rf=0.2) to provide the desired product.

Step B(2): De-benzylation (Carbamate/Urea 1)

The desired urea or carbamate obtained in Step B(1) was dissolved in THF (10 ml) and treated with Pd(OH)$_2$(10% amount). The mixture underwent hydrogenation at room temperature and 1 atm (a balloon filled with hydrogen) of hydrogen for 5 hours. The mixture was filtered and the filtrate was concentrated under vacuum. The residue was purified by prep-HPLC to provide the desired product.

Table 3 discloses compounds 5-1 through 5-11 that were made in accordance to the general procedure outlined in Example 5 and by utilizing the appropriate urea or carbamate.

TABLE 3

| Example | Name | ¹H NMR | Structure |
|---|---|---|---|
| 5-1 | 1-(4-hydroxy-2-(1H-pyrazol-1-yl)pyrimidin-5-yl)-3-phenylurea | ¹H NMR (DMSO-d$_6$, 300 MHz,): δ 12.91(br, 1H), 9.50(s, 1H), 8.52(m, 3H), 7.97(s, 1H), 7.45(m, 2H), 7.26(m, 2H), 690(m, 1H), 6.65 (s, 1H). (M + H)⁺ = 297.1 | 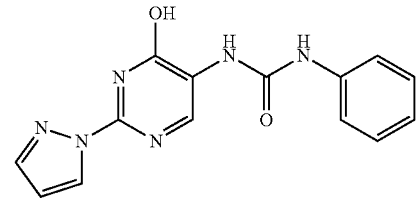 [SMILES: O=C(Nc1ccccc1)Nc1cnc(-n2cccn2)nc1O] |
| 5-2 | 1-benzyl-3-(4-hydroxy-2-(1H-pyrazol-1-yl)pyrimidin-5-yl)urea | ¹H NMR (DMSO-d$_6$, 300 MHz,): δ 12.80(br, 1H), 8.32(m, 3H), 7.94(s, 1H), 7.29(m, 6H), 6.63(s, 1H), 4.28 (d, J = 6 Hz, 2H). (M + H)⁺ = 311.2. | 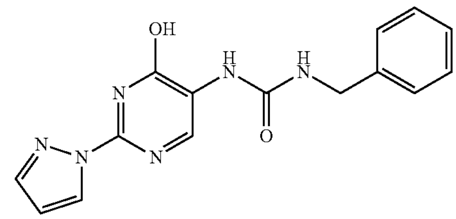 [SMILES: O=C(NCc1ccccc1)Nc1cnc(-n2cccn2)nc1O] |
| 5-3 | 1-(4-hydroxy-2-(1H-pyrazol-1-yl)pyrimidin-5-yl)-3-(1-phenylethyl)urea | ¹H NMR (DMSO-d$_6$, 300 MHz,): δ 12.63(br, 1H), 8.46(s, 1H), 8.23(m, 1H), 7.95(s, 1H), 7.60(s, 1H), 7.20(m, 5H), 6.62(s, 1H), 4.77 (m, 1H), 1.36 (d, J = 6 Hz, 3H). (M + H)⁺ = 325.1. | 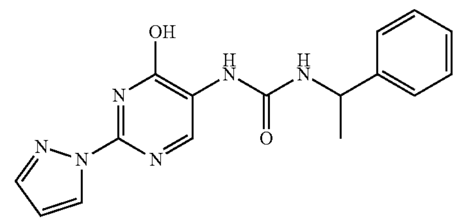 [SMILES: CC(NC(=O)Nc1cnc(-n2cccn2)nc1O)c1ccccc1] |
| 5-4 | 1-cyclohexyl-3-(4-hydroxy-2-(1H-pyrazol-1-yl)pyrimidin-5-yl)urea | ¹H NMR (DMSO-d$_6$, 300 MHz,): δ 12.65(br, 1H), 8.14(m, 3H), 7.95(s, 1H), 7.06(s, 1H), 6.64(s, 1H), 3.32 (m, 1H), 1.16(m, 10H). (M + H)⁺ = 303.2. | 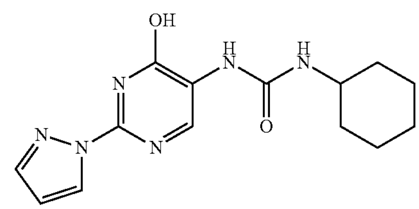 [SMILES: O=C(Nc1cnc(-n2cccn2)nc1O)NC1CCCCC1] |
| 5-5 | 1-cyclopentyl-3-(4-hydroxy-2-(1H-pyrazol-1-yl)pyrimidin-5-yl)urea | ¹H NMR (DMSO-d$_6$, 300 MHz,): δ 12.85(br, 1H), 8.54(s, 1H), 8.40(s, 1H), 8.14(s, 1H), 8.00(s, 1H), 7.17(s, 1H), 6.69(s, 1H), 3.93(m, 1H), 1.60(m, 8H). (M + H)⁺ = 288.9. | 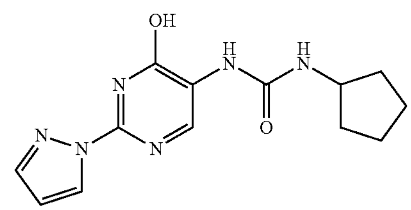 [SMILES: O=C(Nc1cnc(-n2cccn2)nc1O)NC1CCCC1] |
| 5-6 | ert-butyl-3-(4-hydroxy-2-(1H-pyrazol-1-yl)pyrimidin-5-yl)urea | ¹H NMR (DMSO-d6, 300 MHz,): δ 12.78(br, 1H), 8.47(s, 1H), 8.34(s, 1H), 8.08(s, 1H), 7.94(s, 1H), 6.98(s, 1H), 6.62(s, 1H), 1.23 (s, 9H). (M + H)+ = 277.2. | 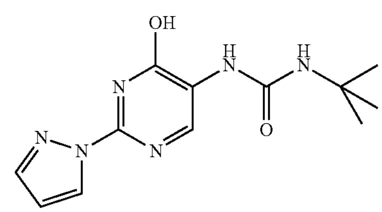 [SMILES: CC(C)(C)NC(=O)Nc1cnc(-n2cccn2)nc1O] |
| 5-7 | 3-(4-hydroxy-2-(1H-pyrazol-1-yl)pyrimidin-5-yl)-1,1-diphenylurea | ¹H NMR (DMSO-d6, 300 MHz,): δ 12.85(br, 1H), 8.50(d, 1H), 8.32(s, 1H), 7.95(s, 1H), 7.30(m, 10H), 6.62(m, 1H). (M + H)⁺ = 373.1. | 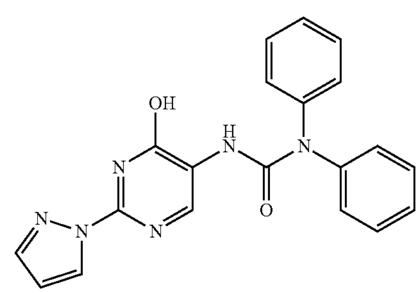 [SMILES: O=C(Nc1cnc(-n2cccn2)nc1O)N(c1ccccc1)c1ccccc1] |

TABLE 3-continued

| Example | Name | $^1$H NMR | Structure |
|---|---|---|---|
| 5-8 | 3-(4-hydroxy-2-(1H-pyrazol-1-yl)pyrimidin-5-yl)-1-isopropyl-1-phenylurea | $^1$H NMR (DMSO-d6, 300 MHz,): δ 12.71(br, 1H), 8.46(d, 1H), 8.31(s, 1H), 7.84(s, 1H), 7.50(m, 3H), 7.31(m, 2H), 6.77(s, 1H), 6.61(s, 1H), 4.69 (m, 1H), 1.02(d, 6H),. (M + H)$^+$ = 339.0. | 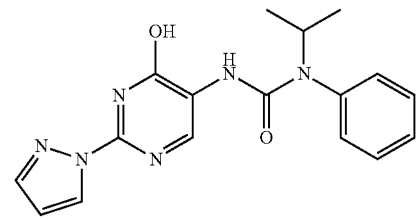 |
| 5-9 | phenyl 4-hydroxy-2-(1H-pyrazol-1-yl)pyrimidin-5-ylcarbamate | $^1$H NMR (DMSO-d$_6$, 300 MHz,): δ 13.03(br, 1H), 9.21(s, 1H), 8.55(s, 1H), 8.20(s, 1H), 7.90(s, 1H), 7.20(m, 4H), 6.66 (s, 1H). (M + H)$^+$ = 298.2. | 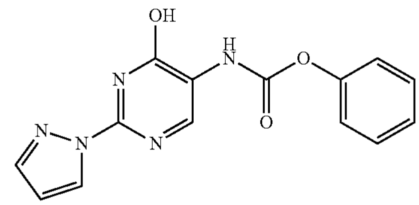 [SMILES: O=C(Nc1cnc(-n2cccn2)nc1O)Oc1ccccc1] |
| 5-10 | cyclohexyl 4-hydroxy-2-(1H-pyrazol-1-yl)pyrimidin-5-ylcarbamate | $^1$H NMR (DMSO-d$_6$, 300 MHz,): δ 12.96(br, 1H), 8.52(s, 1H), 8.18(m, 2H), 7.95(s, 1H), 6.64(s, 1H), 4.63(m, 1H), 1.42(m, 4H), 1.23 (m, 6H). (M + H)$^+$ = 304.2. | 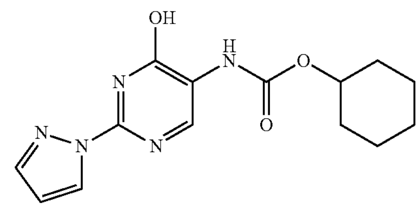 |
| 5-11 | cyclopentyl 4-hydroxy-2-(1H-pyrazol-1-yl)pyrimidin-5-ylcarbamate | $^1$H NMR (DMSO-d$_6$, 300 MHz,): δ 12.96(br, 1H), 8.52(s, 1H), 8.18(m, 2H), 7.95(s, 1H), 6.64(s, 1H), 5.05(m, 1H), 1.56 (m, 8H). (M + H)$^+$ = 290.2. | 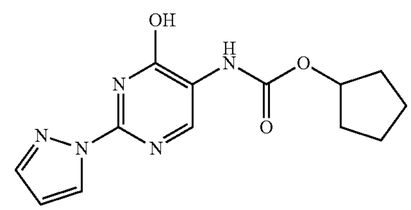 [SMILES: O=C(Nc1cnc(-n2cccn2)nc1O)OC1CCCC1] |
| 5-12 | tert butyl 4-hydroxy-2-(1H-pyrazol-1-yl)pyrimidin-5-ylcarbamate | $^1$H NMR (DMSO-d$_6$, 300 MHz): δ 8.48(s, 1H), 8.12(s, 1H), 7.91(d, 2H), 6.60(s, 1H), 1.45(m, 9H). (M + H)$^+$ = 278.1 | 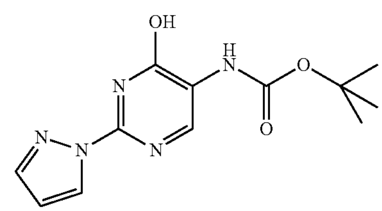 [SMILES: CC(C)(C)OC(=O)Nc1cnc(-n2cccn2)nc1O] |
| 5-13 | butyl 4-hydroxy-2-(1H-pyrazol-1-yl)pyrimidin-5-ylcarbamate | $^1$H-NMR (DMSO-d6, 300 MHz,): δ 8.36(m, 1H), 8.16(s, 1H), 7.56-7.59(m, 2H), 6.35(s, 1H), 4.02-4.07(t, 2H), 1.58(m, 2H), 1.35(m, 2H), 0.91(t, 3H). (M + H)$^+$ = 278.1 | 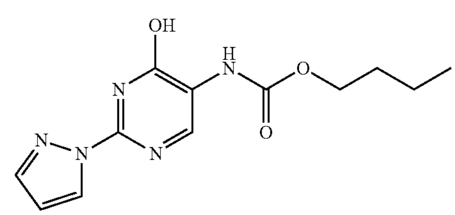 [SMILES: CCCCOC(=O)Nc1cnc(-n2cccn2)nc1O] |
| 5-14 | 4-methoxyphenyl 4-hydroxy-2-(1H-pyrazol-1-yl)pyrimidin-5-ylcarbamate | $^1$H-NMR (DMSO-d6, 300 MHz,): δ 13.03(s, 1H), 9.15(m, 1H), 8.54(s, 1H), 8.20(m, 1H), 7.96(s, 1H), 7.13(m, 2H), 6.97(m, 2H), 6.66(s, 1H), 3.75(s, 3H). (M + H)$^+$ = 328.1 | 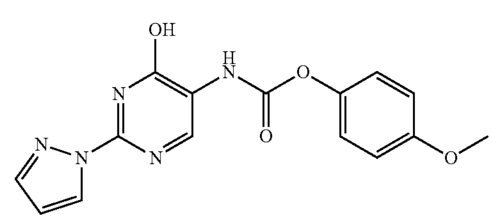 [SMILES: COc1ccc(OC(=O)Nc2cnc(-n3cccn3)nc2O)cc1] |

TABLE 3-continued

| Example | Name | $^1$H NMR | Structure |
|---|---|---|---|
| 5-15 | 3,3-dimethylbutyl 4-hydroxy-2-(1H-pyrazol-1-yl)pyrimidin-5-ylcarbamate | $^1$H-NMR (CDCl3-d6, 300 MHz,): δ 8.60(s, 1H), 8.39(s, 1H), 7.73(s, 1H), 7.31(s, 1H), 6.53(s, 1H), 4.22-4.27(t, 2H), 1.60-1.65(t, 2H), 0.97(s, 9H). (M + H)$^+$ = 306.2 | 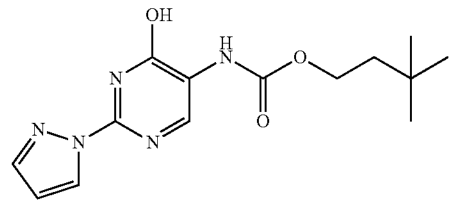 [SMILES: CC(C)(C)CCOC(=O)Nc1cnc(-n2cccn2)nc1O] |
| 5-16 | phenethyl 4-hydroxy-2-(1H-pyrazol-1-yl)pyrimidin-5-ylcarbamate | $^1$H-NMR (DMSO-d6, 300 MHz,): δ 12.91(s, 1H), 8.51(m, 1H), 8.41(s, 1H), 8.17(m, 1H), 7.94(s, 1H), 7.28(m, 5H), 6.63(s, 1H), 4.25-4.29(t, 2H), 2.90-2.94(t, 2H). (M + H)$^+$ = 326.1 | 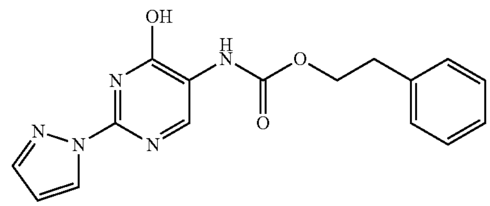 [SMILES: O=C(Nc1cnc(-n2cccn2)nc1O)OCCc1ccccc1] |
| 5-17 | biphenyl-4-yl 4-hydroxy-2-(1H-pyrazol-1-yl)pyrimidin-5-ylcarbamate | $^1$H-NMR (DMSO-d6, 300 MHz,): δ 12.88(s, 1H), 9.27(s, 1H), 8.54(s, 1H), 8.22(s, 1H), 7.96(m, 1H), 7.65-7.71(m, 4H), 7.27-7.48(m, 5H), 6.66(s, 1H). (M + H)$^+$ = 374.0 | 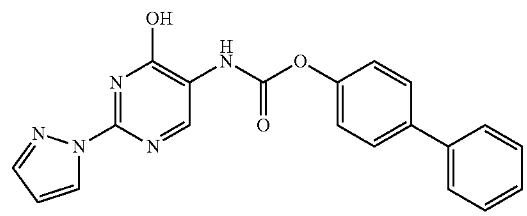 [SMILES: O=C(Nc1cnc(-n2cccn2)nc1O)Oc1ccc(-c2ccccc2)cc1] |
| 5-18 | naphthalen-2-yl 4-hydroxy-2-(1H-pyrazol-1-yl)pyrimidin-5-ylcarbamate | $^1$H-NMR (DMSO-d6, 300 MHz,): δ 12.91(s, 1H), 9.33 (s, 1H), 8.54(s, 1H), 8.21(s, 1H), 7.91-7.99(m, 4H), 7.74(s, 1H), 7.37-7.55(m, 5H), 6.65(s, 1H). (M + H)$^+$ = 348.2 | 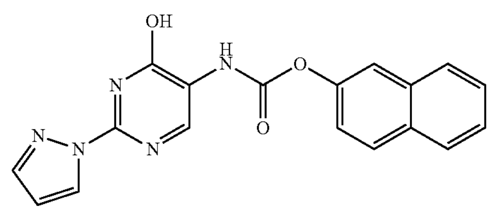 [SMILES: O=C(Nc1cnc(-n2cccn2)nc1O)Oc1ccc2ccccc2c1] |

Example 6-1

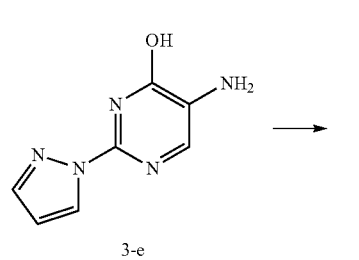

1-benzhydryl-3-(4-hydroxy-2-(1H-pyrazol-1-yl)pyrimidin-5-yl)thiourea(6-1)

5-amino-2-(1H-pyrazol-1-yl)pyrimidin-4-ol, 3-e(Sigma-Aldrich), (44 mg, 0.25 mmol) and isothiocyanatodiphenylmethane (56 mg, 0.25 mmol) were dissolved in dry THF and the mixture was stirred at reflux for 60 hours. Then the mixture was filtered. The solid was washed with MeOH and purified by pre-HPLC to give the title compound, 6-1. $^1$H NMR (DMSO-d$_6$, 300 MHz): δ 12.72 (br, 1H), 9.29 (br, 3H), 8.50 (d, 1H), 7.96 (s, 1H), 7.23 (m, 10H), 6.65 (m, 2H). (M+H)$^+$=403.1.

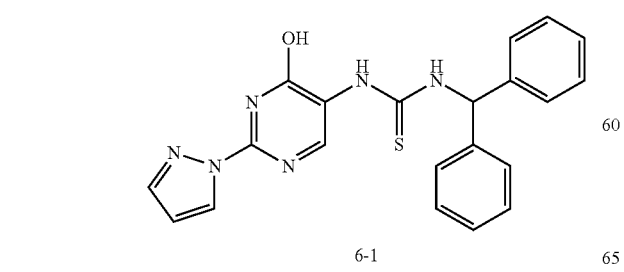

Example 7-1

1-(4-hydroxy-2-(1H-pyrazol-1-yl)pyrimidin-5-yl)-3-(1-phenylethyl)thiourea(7-1)

5-amino-2-(1H-pyrazol-1-yl)pyrimidin-4-ol, 3-e, (100 mg, 0.56 mmol) and alpha-methylbenzyl isothiocyanate (Sigma-Aldrich) (92 mg, 0.56=01) were dissolved in dry THF and the mixture was stirred at reflux for 60 hours. Then the mixture was filtered. The solid was washed with MeOH and purified by pre-HPLC to give the title compound, 7-1. $^1$H NMR (DMSO-d$_6$, 300 MHz): δ 9.21 (br, 3H), 8.50 (d, 1H), 7.95 (s, 1H), 7.22 (m, 5H), 6.65 (s, 2H), 5.41 (m, 1H), 1.41 (d, 3H). (M+H)$^+$=341.1.

Example 8-1

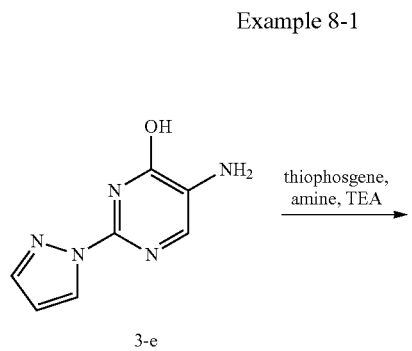

3-e 8-1

1-(4-hydroxy-2-(1H-pyrazol-1-yl)pyrimidin-5-yl)-3-(2-phenylpropan-2-yl)thiourea(8-1)

2-phenylpropan-2-amine (500 mg, 3.7 mmol) and Et$_3$N (747 mg, 7.4 mmol) was dissolved in dry ethyl acetate (10 ml), thiophosgene (425 mg, 3.7 mmol) was added dropwise to the mixture at 0° C. The reaction mixture was warmed to room temperature and stirred for 2 hours. The mixture was washed with water and brine, dried and concentrated. The residue was dissolved in THF (10 ml) and 5-amino-2-(1H-pyrazol-1-yl)pyrimidin-4-ol, 3-e, (655 mg, 3.7 mmol) was added. The resulting mixture was refluxed for 60 hours. Then it was filtered and the solid was washed with MeOH and purified by pre-HPLC to give the title compound, 8-1. NMR (DMSO-d$_6$, 300 MHz): δ 12.62 (br, 1H), 9.23 (br, 1H), 8.49 (m, 1H), 7.93 (s, 1H), 7.13 (m, 5H), 6.64 (m, 1H), 1.70 (s, 6H). (M+H)$^+$=355.1.

Example 9-1

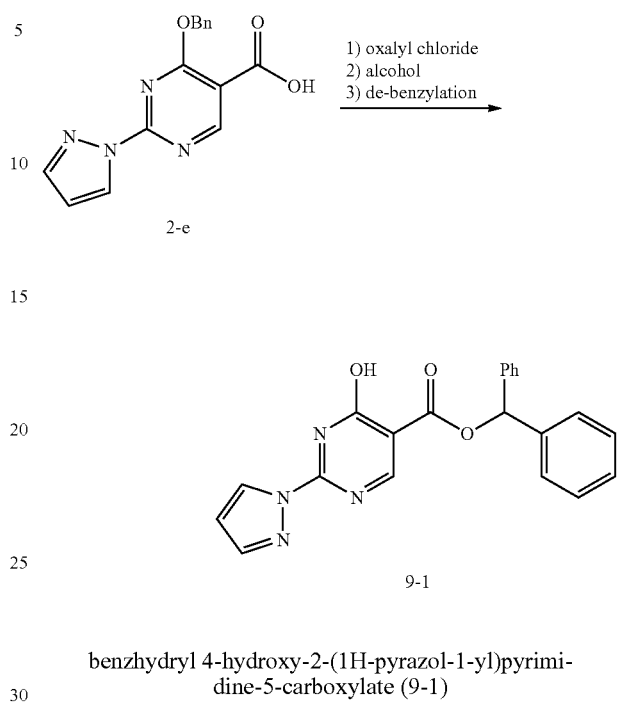

2-e 9-1 benzhydryl 4-hydroxy-2-(1H-pyrazol-1-yl)pyrimidine-5-carboxylate (9-1)

To a solution of 4-(benzyloxy)-2-(1H-pyrazol-1-yl)pyrimidine-5-carboxylic acid, 2-e, (1 g, 3.38 mmol) in dry DCM (20 ml) was added dropwise oxalyl chloride (0.44 ml, 5.07 mmol) at 0° C. and catalytic DMF. The reaction mixture was stirred for 0.3 hours at room temperature. Then it was concentrated under vacuum and the residue was dissolve in DCM (10 ml). To the mixture was added dropwise a solution of diphenylmethanol (685 mg, 3.72 mmol) and Et$_3$N (1.02 g, 10.1 mmol) in DCM (20 ml) at 0° C. The resulting mixture was stirred at room temperature for 3 hours. The resulting mixture was then concentrated and the residue was purified on silica gel (petroleum ether/ethyl acetate=3/1) to give an ester (0.9 g, 58%).

The ester (200 mg, 0.43 mmol) was dissolved in dry THF (10 ml) and Pd(OH)$_2$/C (30 mg) was added. The reaction mixture was stirred under H$_2$ balloon at room temperature for 5 hours. The mixture was filtered and the filtrate was concentrate under vacuum. The residue was purified by pre-HPLC to give the title compound, 9-1. $^1$H NMR (DMSO-d$_6$, 300 MHz): δ 8.76 (br, 1H), 8.60 (d, 1H), 7.99 (s, 1H), 7.27 (m, 11H), 6.98 (s, 1H), 6.68 (m, 1H). (M+Na)$^+$=395.1.

Example 10

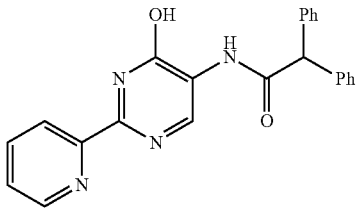

10-1

-continued
Synthesis of 10-1

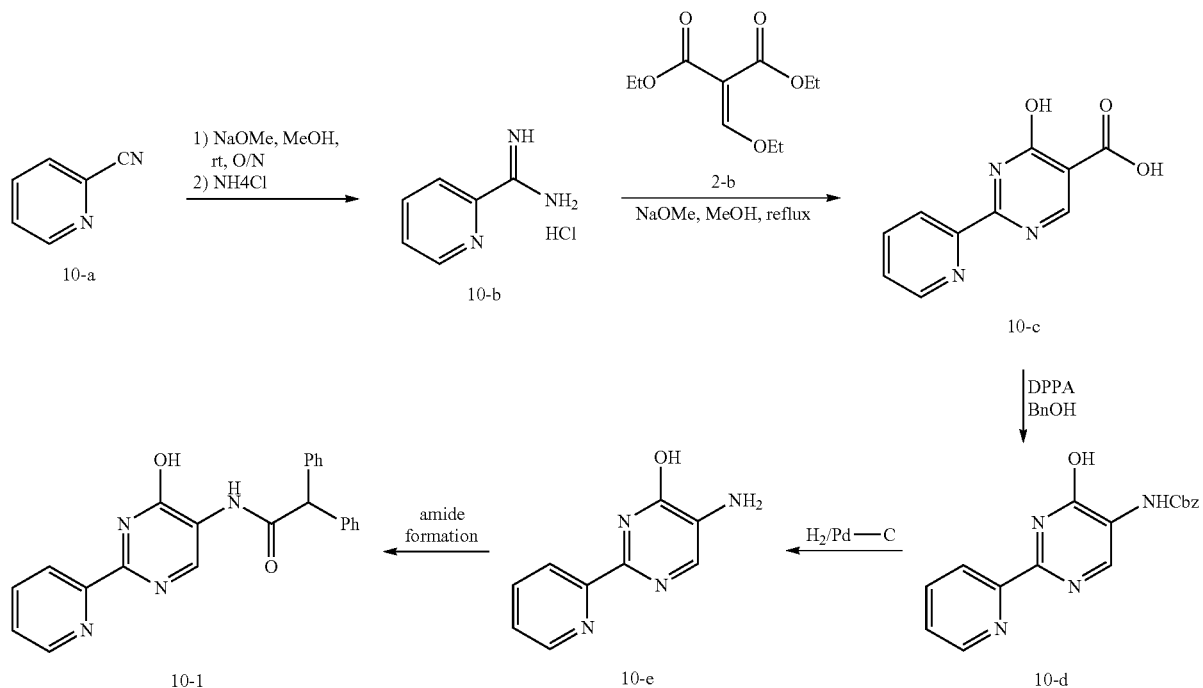

Step A: Picolinamidine hydrochloride (10-b)

To a solution of 2-cyanopyridine (10-a) (Sigma-Aldrich) (100 g, 0.95 mol) in methanol (1.5 L) under nitrogen was added sodium methoxide (2.5 g, 44 mmol). The reaction mixture was stirred at room temperature for 24 hours. Ammonium chloride (53.5 g, 1 mol) was added to the reaction mixture. The mixture was stirred at room temperature for 4 h and the solvent was removed in vacuo. The residue was washed with ipropanol/ethyl acetate=1/10 and dried in vacuo to provide compound 10-b (100 g, 66%).

Step B: 4-hydroxy-2-(pyridin-2-yl)pyrimidine-5-carboxylic acid (10-c)

To picolinamidine hydrochloride (10-b) (112 g, 0.71 mol) in MeOH (1.1 L) was added sodium methoxide (39.4 g, 0.71 mol) and diethyl ethoxymethylenemalonate (2-b) (142 g, 0.71 mol). The reaction was heated at reflux overnight and then cooled to room temperature. The resulting mixture was filtered and to the filtrate was added potassium hydroxide (71.4 g, 1.37 mol) in water (265 mL). The reaction was heated at reflux for 2 h. The reaction mixture was cooled to room temperature before adding conc. HCl (37%, 180 mL, 2.35 mol) in portions. The reaction aged for 2 h. The solids were filtered and rinsed with EtOH, $Et_2O$ and then hexane to provide compound 10-c (110 g, 65%).

Step C: Benzyl 4-hydroxy-2-(pyridin-2-yl)pyrimidin-5-ylcarbamate (10-d)

To a solution of 4-hydroxy-2-(pyridin-2-yl)pyrimidine-5-carboxylic acid (10-c) (10 g, 46 mmol) in toluene (150 ml) was added DPPA (13.94 g, 50.6 mmol), $Et_3N$ (9.31 g, 92.1 mmol) and benzyl alcohol (14.93 g, 0.14 mol). The resulting mixture was heated at reflux overnight. Then the mixture was concentrated under vacuum and the residue was purified on silica gel chromatography with the eluent of petroleum ether/ethyl acetate=1/5, v/v, (Rf=0.3) to afford the crude compound 10-d (3.2 g). The sample delivered was re-purified on prep-HPLC. $^1$H NMR (DMSO-$d_6$, 300 MHz): δ 8.73 (m, 1H), 8.40 (m, 2H), 8.00 (m, 1H), 7.37 (m, 6H), 5.19 (s, 1H). $(M+H)^+=323.1$.

Step D: 5-amino-2-(pyridin-2-yl)pyrimidin-4-ol (10-e)

Benzyl 4-hydroxy-2-(pyridin-2-yl)pyrimidin-5-ylcarbamate (10-d) (1 g, 3.1 mmol) in methanol (20 ml) was hydrogenated under 1 atm of hydrogen in the presence of Pd/C (500 mg) overnight. The mixture was filtered and the filtrate was concentrated to provide the crude product, 10-e (240 mg).

Step E: N-(4-hydroxy-2-(pyridin-2-yl)pyrimidin-5-yl)-2,2-diphenylacetamide (10-1)

To a solution of 5-amino-2-(pyridin-2-yl)pyrimidin-4-ol (10-e) (120 mg, 0.64 mmol) in MeCN (5 ml) were added HATU (254 mg, 0.67 mmol), $Et_3N$ (130 mg, 1.28 mmol) and 2,2-diphenylacetic acid (135 mg, 0.64 mmol). The resulting mixture was stirred at room temperature for 1 hour. Then the mixture was diluted with water and followed by extraction with dichloromethane. The organic layer was washed with brine, dried over sodium sulfate and concentrated under vacuum. The residue was purified by prep-HPLC to provide compound 10-1. $^1$H NMR (DMSO-$d_6$, 300 MHz): δ 12.50 (br, 1H), 9.85 (br, 1H), 8.73 (m, 2H), 8.10 (m, 1H), 8.00 (m, 1H), 7.60 (m, 1H), 7.35 (m, 10H), 5.75 (s, 1H). $(M+H)^+=383.2$.

Example 11
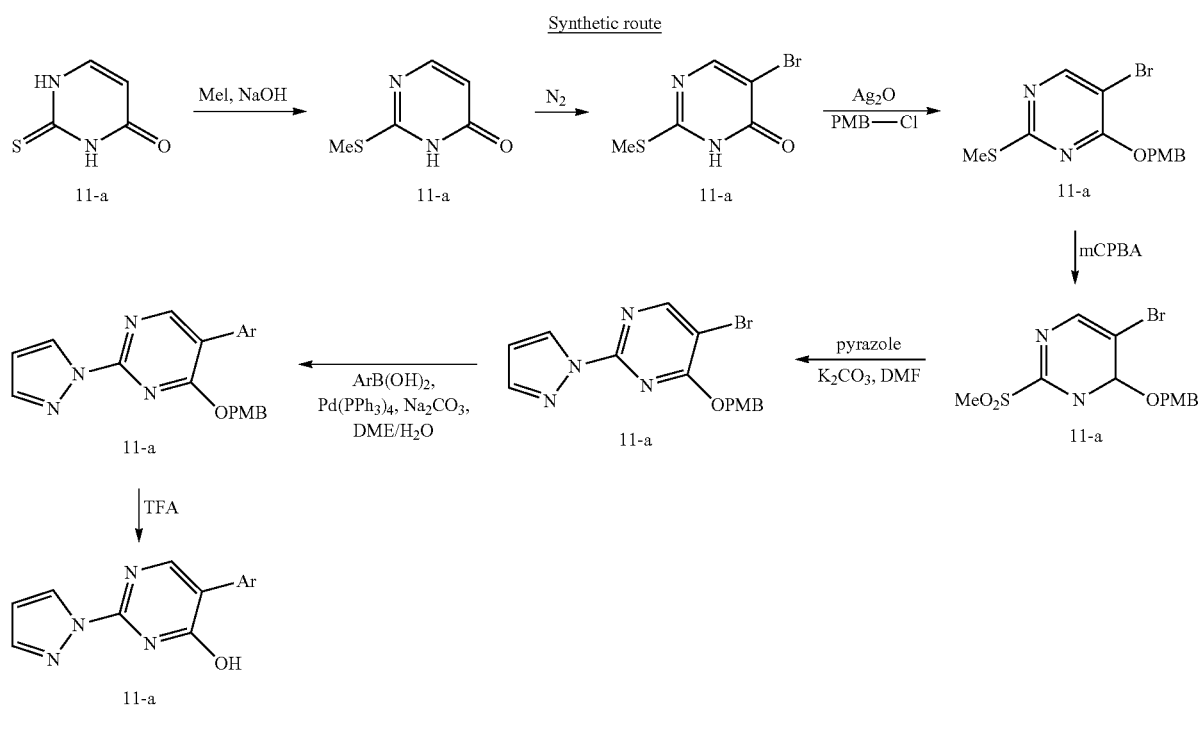
Synthetic route
TABLE 4
| Example | Name | ¹H NMR | Structure |
|---|---|---|---|
| 11-1 | 5-(1-phenyl-1H-pyrazol-4-yl)-2-(1H-pyrazol-1-yl)pyrimidin-4-ol | | 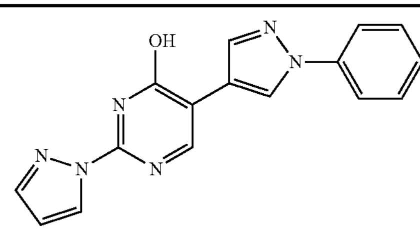 |
| 11-2 | 5-(1-benzyl-1H-pyrazol-4-yl)-2-(1H-pyrazol-1-yl)pyrimidin-4-ol | | 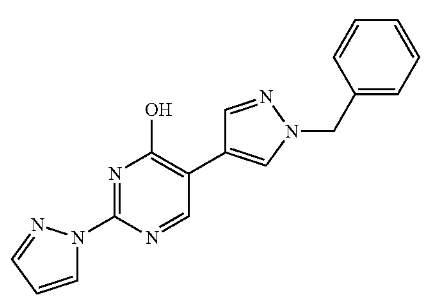 [SMILES: Oc1nc(-n2cccn2)ncc1-c1cnn(Cc2ccccc2)c1] |
| 11-3 | 5-phenyl-2-(1H-pyrazol-1-yl)pyrimidin-4-ol | | 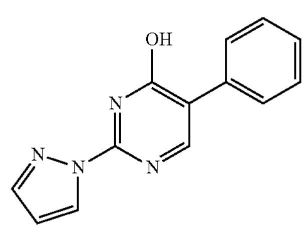 [SMILES: Oc1nc(-n2cccn2)ncc1-c1ccccc1] |

Example 12

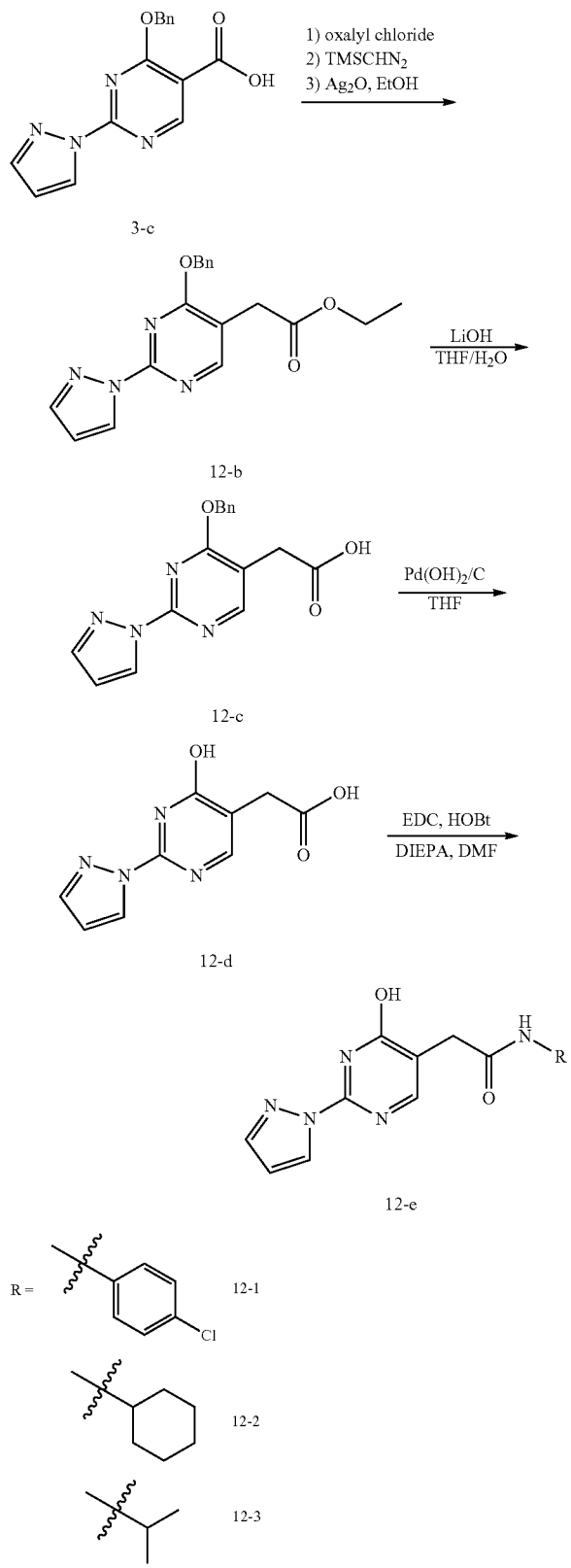

Step A Ethyl 2-(4-(benzyloxy)-2-(1H-pyrazol-1yl)pyrimidin-5-yl)acetate (12-b)

To a solution of 4-(benzyloxy)-2-(1H-pyrazol-1-yl)pyrimidine-5-carboxylic acid, (3-e), (500 mg, 1.69 mmol) in dry DCM (10 ml) was added dropwise oxalyl chloride (0.29 ml, 3.38 mmol) at 0° C. Subsequently, one drop of DMF was added. The reaction mixture was stirred for 3 hours at room temperature. The mixture was concentrated under vacuum and the residue was dissolved in ACM (5 ml). The resulting solution was added dropwise to a solution of TMSCHN$_2$ (193 mg, 8.45 mmol) and Et$_3$N (512 mg, 5.07 mmol) in DCM (20 ml) at 0° C. The mixture was stirred at room temperature overnight. The mixture was then concentrated under vacuum to give the diazo compound as a brown solid (crude product).

To a solution of the diazo compound (397 mg, 1.24 mmol) in EtOH (5 ml) was added Ag$_2$O (287 mg, 1.24 mmol). The mixture was then stirred at room temperature for 2 hours. The mixture was heated to 50° C. and stirred for 1 hour. The mixture was filtered and the filtrate was concentrated under vacuum. The residue was purified by silica gel (PE/EA=5:1) to give compound 12-b as a yellow oil (90 mg, 21.5%). $^1$H NMR (CDCl$_3$-d$_6$, 300 MHz): δ 8.51 (s, 1H), 8.34 (s, 1H), 7.81 (s, 1H), 7.32-7.44 (m, 5H), 6.46 (s, 2H), 5.54 (s, 2H), 4.07-4.14 (q, 2H), 3.58 (s, 2H), 1.15-1.20 (t, 3H). (M+H)$^+$=339.2.

Step B 2-(4-(benzyloxy)-2-(1H-pyrazol-1-yl)pyrimidin-5-yl)acetic acid (12-c)

To a solution of ethyl 2-(4-(benzyloxy)-2-(1H-pyrazol-1-yl)pyrimidin-5-yl)acetate, 12-b, (90 mg, 0.27 mmol) in TRF (6 ml) was added LiOH monohydrate (19 mg, 0.8 mmol) in H$_2$O (3 ml). The mixture was stirred at room temperature for 3 hours. The mixture was concentrated under vacuum and the remaining aqueous solution was extracted with ethyl acetate (5 ml). The separated aqueous phase was adjusted to pH=2 with Conc. HCl. The solid crashed out and was filtered to give compound 12-c (40 mg, 48.5%). $^1$HNMR (DMSO-d$_6$, 300 MHz): δ 12.56 (s, 1H), 8.66 (s, 1H), 8.47 (s, 1H), 7.84 (s, 1H), 7.32-7.52 (M, 5H), 6.59 (s, 1H), 5.57 (S, 2H), 3.61 (s, 2H). (M+H)$^+$=311.1.

Step C 2-(4-hydroxy-2-(1H-pyrazol-1-yl)pyrimidin-5-yl) acetic acid (12-d)

To a solution of 2-(4-(benzyloxy)-2-(1H-pyrazol-1-yl)pyrimidin-5-yl)acetic acid, 12-c, (1.239 g, 4 mmol) in THF (40 ml) was added Pd(OH)$_2$/C (0.14 g). The resulting mixture was hydrogenated at room temperature at 1 atm overnight. The mixture was filtered and the filtrate was concentrate under vacuum to give compound 12-d (800 mg, 91%). $^1$H NMR (DMSO-d$_6$, 300 MHz): δ 12.59 (s, 2H), 8.53 (s, 1H), 7.89 (s, 2H), 6.61 (s, 1H), 3.37 (s, 2H). (M+H)$^+$=221.1.

Step D N-(4-chlorophenyl)-2-(4-hydroxy-2-(1H-pyrazol-1-yl)pyrimidin-5-yl)acetamide (12-1)

To a solution of 2-(4-hydroxy-2-(1H-pyrazol-1-yl)pyrimidin-5-yl)acetic acid, 12-d, (150 mg, 0.68 mmol) and HOBt (101.2 mg, 0.75 mmol) in DMF (5 ml) was added EDC.HCl (144 mg, 0.75 mmol) and DIEPA (264 mg, 2.05 mmol). The solution was stirred at room temperature for 5 mins before the addition of the chlorophenyl amine (0.75 mmol) (Sigma-Aldrich). The mixture was stirred at room temperature for 24 hours. The mixture was then diluted with water and extracted with ethyl acetate. The organic layer was concentrated under vacuum and the residue was purified by silica gel column or Prep-HPLC to give the final compound 12-1. $^1$H NMR (DMSO-d$_6$, 300 MHz): δ 10.23 (s, 1H), 8.56 (d, 1H), 7.92 (s, 1H), 7.63 (d, 2H), 7.37 (d, 2H), 6.64 (s, 1H), 3.53 (s, 2H). (M+H)$^+$=330.1.

In addition to compound 12-1, Table 5 discloses compounds 12-2 and 12-3 that were made in accordance to the general procedure outlined in Example 13 and by utilizing the appropriate amine.

TABLE 5

| Example | Name | ¹H NMR | Structure |
|---|---|---|---|
| 12-1 | N-(4-chlorophenyl)-2-(4-hydroxy-2-(1H-pyrazol-1-yl)pyrimidin-5-yl)acetamide | ¹H NMR (DMSO-$d_6$, 300 MHz,): δ 10.23 (s, 1H), 8.56 (d, 1H), 7.92 (s, 1H), 7.63 (d, 2H), 7.37 (d, 2H), 6.64 (s, 1H), 3.53 (s, 2H). $(M+H)^+ = 330.1$ | 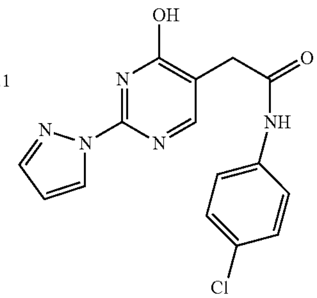 |
| 12-2 | N-cyclohexyl-2-(4-hydroxy-2-(1H-pyrazol-1-yl)pyrimidin-5-yl)acetamide | ¹H NMR (DMSO-$d_6$, 300 MHz,): δ 12.77 (s, 1H), 8.54 (d, 1H), 7.82-7.89 (m, 2H), 7.61 (s, 1H), 3.53 (m, 1H), 3.22 (s, 2H), 1.13-1.74 (m, 10H). $(M+H)^+ = 302.2$ | 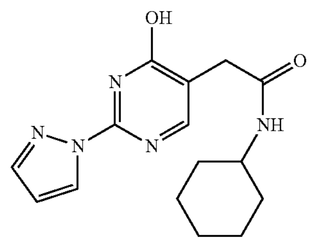 [SMILES: O=C(Cc1cnc(-n2cccn2)nc1O)NC1CCCCC1] |
| 12-3 | 2-(4-hydroxy-2-(1H-pyrazol-1-yl)pyrimidin-5-yl)-N-isopropylacetamide | ¹H NMR (DMSO-$d_6$, 300 MHz,): δ 8.54 (s, 1H), 7.82-7.91 (m, 3H), 6.63 (s, 1H), 3.83 (m, 1H), 3.22 (s, 2H), 1.06 (d, 6H). $(M+H)^+ = 262.0$ | 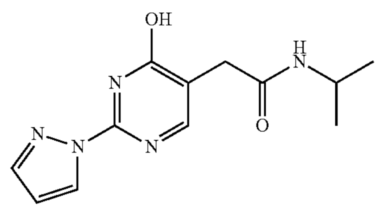 [SMILES: CC(C)NC(=O)Cc1cnc(-n2cccn2)nc1O] |

Example 13

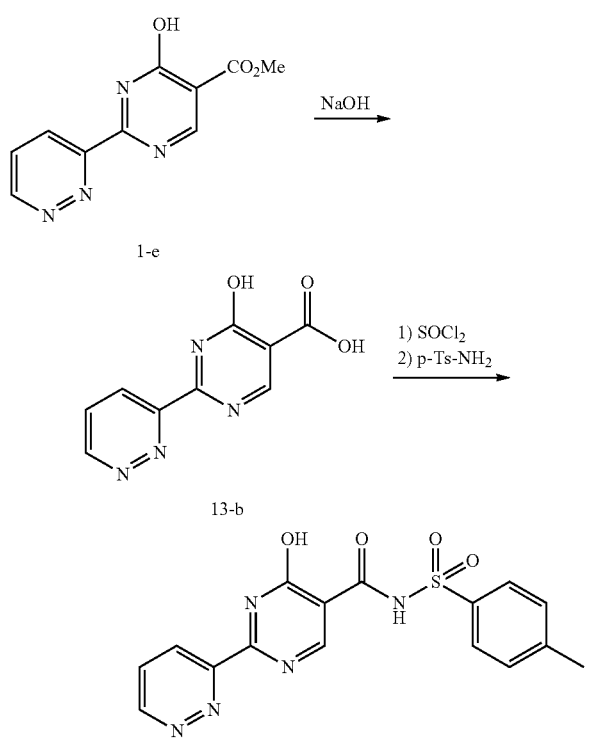

4-hydroxy-2-(pyridazin-3-yl)-N-tosylpyrimidine-5-carboxamide (13-1)

4-hydroxy-2-(pyridazin-3-yl)pyrimidine-5-carboxylic acid, 13-b, (350 mg, 1.6 mmol, which was prepared from compound 1-e via sodium hydroxide hydrolysis in a similar manner as the conversion of 3-b to 3-c) in thionyl chloride (10 ml) was heated at reflux for 4 h. The mixture was concentrated under vacuum and the residue was co-evaporated with dichloromethane twice. The remaining oil was dissolved in dichloromethane (10 ml). p-toluenesulfonamide (329 mg, 1.93 mmol), triethylamine (486 mg, 4.82 mmol) and DMAP (390 mg, 3.2 mmol) were added to the solution at room temperature. The mixture was subsequently stirred at room temperature overnight. The mixture was then concentrated under vacuum and the residue was diluted with water (10 ml). The solid crashed out and then filtered out of the solution. The solids were then recrystallization in methanol/ethyl acetate to afford compound 13-1 (300 mg, 50%). ¹H NMR (DMSO-$d_6$, 300 MHz): δ 12.92 (br, 1H), 9.51 (s, 1H), 8.53 (s, 2H), 8.00 (m, 3H), 7.46 (s, 2H), 2.41 (s, 3H). $(M+H)^+=372.1$.

Biological Assays

The exemplified compounds, Examples 1 through 13 of the present invention, have been found to inhibit the interaction between PHD2 and a HIF peptide and exhibit $IC_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 96-well plate was added 1 μL of test compound in DMSO and 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 30 min preincubation at room temperature, the enzymatic reactions were initiated by the addition of 4 μt of substrates (final concentrations of 0.2 μM 2-oxoglutarate and 0.5 μM HIF-1α peptide biotinyl-DLDLEMLAPYIPMDDDFQL (SEQ ID NO:1)). After 2 hr at room temperature, the reactions were terminated and signals were developed by the addition of a 25 μL quench/detection mix to a final concentration of 1 mM ortho-phenanthroline, 0.1 mM EDTA, 0.5 nM anti-(His)6 LANCE reagent (Perkin-Elmer Life Sciences), 100 nM AF647-labeled streptavidin (Invitrogen), and 2 μg/ml (His)-6-VHL complex (S. Tan(2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

Table 6 depicts the inhibition of HIF PHD2 activity expressed as $IC_{50}$ (nM), for the exemplified compounds, 1-1, 1-2, 2-1, 3-1 to 3-6, 4-1, and 5-1 of the present invention.

TABLE 6

PHD2 Inhibition Activity

| Cmp. No. | Compound IUPAC name | $IC_{50}$ (nM) |
|---|---|---|
| 2-1 | N-(4-hydroxy-2-(1H-pyrazol-1-yl)pyrimidin-5-yl)-2,2-diphenylacetamide | + |
| 3-1 | 2-chloro-N-(4-hydroxy-2-(1H-pyrazol-1-yl)pyrimidin-5-yl)benzamide | + |
| 3-2 | 3-chloro-N-(4-hydroxy-2-(1H-pyrazol-1-yl)pyrimidin-5-yl)benzamide | + |
| 3-3 | 4-chloro-N-(4-hydroxy-2-(1H-pyrazol-1-yl)pyrimidin-5-yl)benzamide | ++ |
| 3-4 | 3-(trifluoromethyl)-N-(4-hydroxy-2-(1H-pyrazol-1-yl)pyrimidin-5-yl)benzamide | + |
| 3-5 | 4-(trifluoromethyl)-N-(4-hydroxy-2-(1H-pyrazol-1-yl)pyrimidin-5-yl)benzamide | ++ |
| 3-6 | N-(4-hydroxy-2-(1H-pyrazol-1-yl)pyrimidin-5-yl)-2-(naphthalen-3-yl)acetamide | + |
| 3-7 | 2-cyano-N-(4-hydroxy-2-(1H-pyrazol-1-yl)pyrimidin-5-yl)benzamide | +++ |
| 3-8 | 3-cyano-N-(4-hydroxy-2-(1H-pyrazol-1-yl)pyrimidin-5-yl)benzamide | ++ |
| 3-9 | 4-cyano-N-(4-hydroxy-2-(1H-pyrazol-1-yl)pyrimidin-5-yl)benzamide | ++ |
| 3-10 | 2-(trifluoromethyl)-N-(4-hydroxy-2-(1H-pyrazol-1-yl)pyrimidin-5-yl)benzamide | + |
| 3-11 | N-(4-hydroxy-2-(1H-pyrazol-1-yl)pyrimidin-5-yl)-2-methoxybenzamide | ++ |
| 3-12 | N-(4-hydroxy-2-(1H-pyrazol-1-yl)pyrimidin-5-yl)-3-methoxybenzamide | ++ |
| 3-13 | N-(4-hydroxy-2-(1H-pyrazol-1-yl)pyrimidin-5-yl)-4-methoxybenzamide | ++ |
| 3-14 | N-(4-hydroxy-2-(1H-pyrazol-1-yl)pyrimidin-5-yl)-2-(methylsulfonyl)benzamide | +++ |
| 3-15 | N-(4-hydroxy-2-(1H-pyrazol-1-yl)pyrimidin-5-yl)-3-(methylsulfonyl)benzamide | ++ |
| 3-16 | N-(4-hydroxy-2-(1H-pyrazol-1-yl)pyrimidin-5-yl)-4-(methylsulfonyl)benzamide | ++ |
| 3-17 | N-[4-hydroxy-2-(1H-pyrazol-1-yl)pyrimidin-5-yl]biphenyl-2-carboxamide | ++ |
| 3-18 | N-[4-hydroxy-2-(1H-pyrazol-1-yl)pyrimidin-5-yl]biphenyl-3-carboxamide | ++ |
| 3-19 | N-[4-hydroxy-2-(1H-pyrazol-1-yl)pyrimidin-5-yl]biphenyl-4-carboxamide | + |
| 3-20 | N-(4-hydroxy-2-(1H-pyrazol-1-yl)pyrimidin-5-yl)-2-phenoxybenzamide | ++ |
| 3-21 | N-(4-hydroxy-2-(1H-pyrazol-1-yl)pyrimidin-5-yl)-3-phenoxybenzamide | + |
| 3-22 | N-(4-hydroxy-2-(1H-pyrazol-1-yl)pyrimidin-5-yl)-4-phenoxybenzamide | + |
| 3-23 | 2-(2-chlorophenyl)-N-(4-hydroxy-2-(1H-pyrazol-1-yl)pyrimidin-5-yl)acetamide | + |
| 3-24 | 2-(3-chlorophenyl)-N-(4-hydroxy-2-(1H-pyrazol-1-yl)pyrimidin-5-yl)acetamide | + |
| 3-25 | 2-(4-chlorophenyl)-N-(4-hydroxy-2-(1H-pyrazol-1-yl)pyrimidin-5-yl)acetamide | + |
| 3-26 | 2-(3-cyanophenyl)-N-(4-hydroxy-2-(1H-pyrazol-1-yl)pyrimidin-5-yl)acetamide | + |
| 3-27 | 2-(2-(trifluoromethyl)phenyl)-N-(4-hydroxy-2-(1H-pyrazol-1-yl)pyrimidin-5-yl)acetamide | + |
| 3-28 | 2-(3-(trifluoromethyl)phenyl)-N-(4-hydroxy-2-(1H-pyrazol-1-yl)pyrimidin-5-yl)acetamide | + |
| 3-29 | 2-(4-(trifluoromethyl)phenyl)-N-(4-hydroxy-2-(1H-pyrazol-1-yl)pyrimidin-5-yl)acetamide | + |
| 3-30 | N-(4-hydroxy-2-(1H-pyrazol-1-yl)pyrimidin-5-yl )-2-(2-methoxyphenyl)acetamide | + |
| 3-31 | N-(4-hydroxy-2-(1H-pyrazol-1-yl)pyrimidin-5-yl)-2-(3-methoxyphenyl)acetamide | + |
| 3-32 | N-(4-hydroxy-2-(1H-pyrazol-1-yl)pyrimidin-5-yl)-2-(4-methoxyphenyl)acetamide | + |
| 3-33 | N-(4-hydroxy-2-(1H-pyrazol-1-yl)pyrimidin-5-yl)-2-phenylpropanamide | + |
| 3-34 | N-(4-hydroxy-2-(1H-pyrazol-1-yl)pyrimidin-5-yl)-2-phenylbutanamide | + |
| 3-35 | N-(4-hydroxy-2-(1H-pyrazol-1-yl)pyrimidin-5-yl)-3-methyl-2-phenylbutanamide | ++ |
| 3-36 | N-(4-hydroxy-2-(1H-pyrazol-1-yl)pyrimidin-5-yl)-3-methyl-2-phenylpentanamide | + |
| 3-37 | N-(4-hydroxy-2-(1H-pyrazol-1-yl)pyrimidin-5-yl)-2-methyl-2-phenylpropanamide | + |
| 3-38 | N-(4-hydroxy-2-(1H-pyrazol-1-yl)pyrimidin-5-yl)-1-phenylcyclopropanecarboxamide | ++ |
| 3-39 | N-(4-hydroxy-2-(1H-pyrazol-1-yl)pyrimidin-5-yl)-2-(naphthalen-1-yl)acetamide | + |
| 3-40 | 2-(benzo[d][1,3]dioxol-5-yl)-N-(4-hydroxy-2-(1H-pyrazol-1-yl)pyrimidin-5-yl)acetamide | + |
| 3-41 | N-(4-hydroxy-2-(1H-pyrazol-1-yl)pyrimidin-5-yl)-2-(pyridin-4-yl)acetamide | ++ |
| 3-42 | 2-(biphenyl-4-yl)-N-(4-hydroxy-2-(1H-pyrazol-1-yl)pyrimidin-5-yl)acetamide | + |
| 3-43 | N-(4-hydroxy-2-(1H-pyrazol-1-yl)pyrimidin-5-yl)heptanamide | + |
| 3-44 | N-(4-hydroxy-2-(1H-pyrazol-1-yl)pyrimidin-5-yl)-3-phenylpropanamide | ++ |
| 3-45 | N-(4-hydroxy-2-(1H-pyrazol-1-yl)pyrimidin-5-yl)-4-phenylbutanamide | + |
| 3-46 | N-(4-hydroxy-2-(1H-pyrazol-1-yl)pyrimidin-5-yl)cyclohexanecarboxamide | ++ |
| 3-47 | tert-butyl4-(4-hydroxy-2-(1H-pyrazol-1-yl)pyrimidin-5-ylcarbamoyl)piperidine-1-carboxylate | + |
| 3-48 | 2-cyclohexyl-N-(4-hydroxy-2-(1H-pyrazo101.01-1-yl)pyrimidin-5-yl)acetamide | + |
| 3-49 | tert-butyl 3-(4-hydroxy-2-(1H-pyrazol-1-yl)pyrimidin-5-ylcarbamoyl)piperidine-1-carboxylate | +++ |
| 3-50 | tert-butyl4-((4-hydroxy-2-(1H-pyrazol-1-yl)pyrimidin-5-ylcarbamoyl)methyl)piperidine-1-carboxylate | ++ |
| 3-51 | tert-butyl 3-(4-hydroxy-2-(1H-pyrazol-1-yl)pyrimidin-5-ylcarbamoyl)pyrrolidine-1-carboxylate | ++ |
| 3-52 | 1,2,3,4-tetrahydro-N-(4-hydroxy-2-(1H-pyrazol-1-yl)pyrimidin-5-yl)naphthalene-1-carboxamide | + |

TABLE 6-continued

PHD2 Inhibition Activity

| Cmp. No. | Compound IUPAC name | IC$_{50}$ (nM) |
|---|---|---|
| 3-53 | 2,3-dihydro-N-(4-hydroxy-2-(1H-pyrazol-1-yl)pyrimidin-5-yl)-1H-indene-1-carboxamide | + |
| 3-54 | 1,2,3,4-tetrahydro-N-(4-hydroxy-2-(1H-pyrazol-1-yl)pyrimidin-5-yl)naphthalene-2-carboxamide | ++ |
| 3-55 | 2,3-dihydro-N-(4-hydroxy-2-(1H-pyrazol-1-yl)pyrimidin-5-yl)-1H-indene-2-carboxamide | + |
| 4-1 | 4-chloro-N-[4-hydroxy-2-(1H-pyrazol-1-yl)pyrimidin-5-yl]benzenesulfonamide | ++ |
| 4-2 | 1-(4-chlorophenyl)-N-[4-hydroxy-2-(1H-pyrazol-1-yl)pyrimidin-5-yl]methanesulfonamide | ++ |
| 4-3 | 3-chloro-N-[4-hydroxy-2-(1H-pyrazol-1-yl)pyrimidin-5-yl]benzenesulfonamide | +++ |
| 4-4 | N-[4-hydroxy-2-(1H-pyrazol-1-yl)pyrimidin-5-yl]-1-[4-(trifluoromethyl)phenyl]methanesulfonamide | +++ |
| 5-1 | 1-(4-hydroxy-2-(1H-pyrazol-1-yl)pyrimidin-5-yl)-3-phenylurea | +++ |
| 5-2 | 1-benzyl-3-(4-hydroxy-2-(1H-pyrazol-1-yl)pyrimidin-5-yl)urea | + |
| 5-3 | 1-(4-hydroxy-2-(1H-pyrazol-1-yl)pyrimidin-5-yl)-3-(1-phenylethyl)urea | + |
| 5-4 | 1-cyclohexyl-3-(4-hydroxy-2-(1H-pyrazol-1-yl)pyrimidin-5-yl)urea | ++ |
| 5-5 | 1-cyclopentyl-3-(4-hydroxy-2-(1H-pyrazol-1-yl)pyrimidin-5-yl)urea | +++ |
| 5-6 | ert-butyl-3-(4-hydroxy-2-(1H-pyrazol-1-yl)pyrimidin-5-yl)urea | +++ |
| 5-7 | 3-(4-hydroxy-2-(1H-pyrazol-1-yl)pyrimidin-5-yl)-1,1-diphenylurea | + |
| 5-8 | 3-(4-hydroxy-2-(1H-pyrazol-1-yl)pyrimidin-5-yl)-1-isopropyl-1-phenylurea | ++ |
| 5-9 | phenyl 4-hydroxy-2-(1H-pyrazol-1-yl)pyrimidin-5-yl carbamate | +++ |
| 5-10 | cyclohexyl 4-hydroxy-2-(1H-pyrazol-1-yl)pyrimidin-5-yl carbamate | ++ |
| 5-11 | cyclopentyl 4-hydroxy-2-(1H-pyrazol-1-yl)pyrimidin-5-yl carbamate | ++ |
| 5-12 | tert-butyl 4-hydroxy-2-(1H-pyrazol-1-yl)pyrimidin-5-yl carbamate | +++ |
| 5-13 | butyl 4-hydroxy-2-(1H-pyrazol-1-yl)pyrimidin-5-yl carbamate | +++ |
| 5-14 | 4-methoxyphenyl 4-hydroxy-2-(1H-pyrazol-1-yl)pyrimidin-5-yl carbamate | ++ |
| 5-15 | 3,3-dimethylbutyl 4-hydroxy-2-(1H-pyrazol-1-yl)pyrimidin-5-yl carbamate | ++ |
| 5-16 | phenethyl 4-hydroxy-2-(1H-pyrazol-1-yl)pyrimidin-5-yl carbamate | ++ |
| 5-17 | biphenyl-4-yl 4-hydroxy-2-(1H-pyrazol-1-yl)pyrimidin-5-yl carbamate | +++ |
| 5-18 | naphthalen-2-yl 4-hydroxy-2-(1H-pyrazol-1-yl)pyrimidin-5-yl carbamate | +++ |
| 6-1 | 1-benzhydryl-3-(4-hydroxy-2-(1H-pyrazol-1-yl)pyrimidin-5-yl)thiourea | + |
| 7-1 | 1-(4-hydroxy-2-(1H-pyrazol-1-yl)pyrimidin-5-yl)-3-(1-phenylethyl)thiourea | + |
| 8-1 | 1-(4-hydroxy-2-(1H-pyrazol-1-yl)pyrimidin-5-yl)-3-(2-phenylpropan-2-yl)thiourea | ++ |
| 9-1 | benzhydryl 4-hydroxy-2-(1H-pyrazol-1-yl)pyrimidine-5-carboxylate | +++ |
| 10-1 | N-(4-hydroxy-2-(pyridin-2-yl)pyrimidin-5-yl)-2,2-diphenylacetamide | ++ |
| 11-1 | 5-(1-phenyl-1H-pyrazol-4-yl)-2-(1H-pyrazol-1-yl)pyrimidin-4-ol | +++ |
| 11-2 | 5-(1-benzyl-1H-pyrazol-4-yl)-2-(1H-pyrazol-1-yl)pyrimidin-4-ol | +++ |
| 11-3 | 5-phenyl-2-(1H-pyrazol-1-yl)pyrimidin-4-ol | +++ |
| 12-1 | N-(4-chlorophenyl)-2-(4-hydroxy-2-(1H-pyrazol-1-yl)pyrimidin-5-yl)acetamide | +++ |
| 12-2 | N-cyclohexyl-2-(4-hydroxy-2-(1H-pyrazol-1-yl)pyrimidin-5-yl)acetamide | +++ |
| 12-3 | 2-(4-hydroxy-2-(1H-pyrazol-1-yl)pyrimidin-5-yl)-N-isopropylacetamide | +++ |
| 13-1 | 4-hydroxy-2-(pyridazin-3-yl)-N-tosylpyrimidine-5-carboxamide | +++ |

+ = 0.5 ≤ IC$_{50}$ ≤ 20 (nM)
++ = 20 < IC$_{50}$ ≤ 100 (nM)
+++ = 100 < IC$_{50}$ ≤ 10000 (nM)

What is claimed is:

1. A compound selected from:

N-(4-hydroxy-2-(1H-pyrazol-1-yl)pyrimidin-5-yl)-2,2-diphenylacetamide;
2-chloro-N-(4-hydroxy-2-(1H-pyrazol-1-yl)pyrimidin-5-yl)benzamide;
3-chloro-N-(4-hydroxy-2-(1H-pyrazol-1-yl)pyrimidin-5-yl)benzamide;
4-chloro-N-(4-hydroxy-2-(1H-pyrazol-1-yl)pyrimidin-5-yl)benzamide;
3-(trifluoromethyl)-N-(4-hydroxy-2-(1H-pyrazol-1-yl)pyrimidin-5-yl)benzamide;
4-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-(naphthalen-3-yl)acetamide;
2-cyano-N-(4-hydroxy-2-(1H-pyrazol-1-yl)pyrimidin-5-yl)benzamide;
3-cyano-N-(4-hydroxy-2-(1H-pyrazol-1-yl)pyrimidin-5-yl)benzamide;
4-cyano-N-(4-hydroxy-2-(1H-pyrazol-1-yl)pyrimidin-5-yl)benzamide;
2-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-methoxybenzamide;
N-(4-hydroxy-2-(1H-pyrazol-1-yl)pyrimidin-5-yl)-3-methoxybenzamide;
N-(4-hydroxy-2-(1H-pyrazol-1-yl)pyrimidin-5-yl)-4-methoxybenzamide;
N-(4-hydroxy-2-(1H-pyrazol-1-yl)pyrimidin-5-yl)-2-(methylsulfonyl)benzamide;
N-(4-hydroxy-2-(1H-pyrazol-1-yl)pyrimidin-5-yl)-3-(methylsulfonyl)benzamide;
N-(4-hydroxy-2-(1H-pyrazol-1-yl)pyrimidin-5-yl)-4-(methylsulfonyl)benzamide;
N-[4-hydroxy-2-(1H-pyrazol-1-yl)pyrimidin-5-yl]biphenyl-2-carboxamide;
N-[4-hydroxy-2-(1H-pyrazol-1-yl)pyrimidin-5-yl]biphenyl-3-carboxamide;
N-[4-hydroxy-2-(1H-pyrazol-1-yl)pyrimidin-5-yl]biphenyl-4-carboxamide;
N-(4-hydroxy-2-(1H-pyrazol-1-yl)pyrimidin-5-yl)-2-phenoxybenzamide;
N-(4-hydroxy-2-(1H-pyrazol-1-yl)pyrimidin-5-yl)-3-phenoxybenzamide;
N-(4-hydroxy-2-(1H-pyrazol-1-yl)pyrimidin-5-yl)-4-phenoxybenzamide;
2-(2-chlorophenyl)-N-(4-hydroxy-2-(1H-pyrazol-1-yl)pyrimidin-5-yl)acetamide;
2-(3-chlorophenyl)-N-(4-hydroxy-2-(1H-pyrazol-1-yl)pyrimidin-5-yl)acetamide;
2-(4-chlorophenyl)-N-(4-hydroxy-2-(1H-pyrazol-1-yl)pyrimidin-5-yl)acetamide;
2-(3-cyanophenyl)-N-(4-hydroxy-2-(1H-pyrazol-1-yl)pyrimidin-5-yl)acetamide;
2-(2-(trifluoromethyl)phenyl)-N-(4-hydroxy-2-(1H-pyrazol-1-yl)pyrimidin-5-yl)acetamide;
2-(3-(trifluoromethyl)phenyl)-N-(4-hydroxy-2-(1H-pyrazol-1-yl)pyrimidin-5-yl)acetamide;
2-(4-(trifluoromethyl)phenyl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(2-methoxyphenyl)acetamide;
N-(4-hydroxy-2-(1H-pyrazol-1-yl)pyrimidin-5-yl)-2-(3-methoxyphenyl)acetamide;
N-(4-hydroxy-2-(1H-pyrazol-1-yl)pyrimidin-5-yl)-2-(4-methoxyphenyl)acetamide;
N-(4-hydroxy-2-(1H-pyrazol-1-yl)pyrimidin-5-yl)-2-phenylpropanamide;
N-(4-hydroxy-2-(1H-pyrazol-1-yl)pyrimidin-5-yl)-2-phenylbutanamide;
N-(4-hydroxy-2-(1H-pyrazol-1-yl)pyrimidin-5-yl)-3-methyl-2-phenylbutanamide;
N-(4-hydroxy-2-(1H-pyrazol-1-yl)pyrimidin-5-yl)-3-methyl-2-phenylpentanamide;
N-(4-hydroxy-2-(1H-pyrazol-1-yl)pyrimidin-5-yl)-2-methyl-2-phenylpropanamide;
N-(4-hydroxy-2-(1H-pyrazol-1-yl)pyrimidin-5-yl)-1-phenylcyclopropanecarboxamide;
N-(4-hydroxy-2-(1H-pyrazol-1-yl)pyrimidin-5-yl)-2-(naphthalen-1-yl)acetamide;
2-(benzo[d][1,3]dioxol-5-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(pyridin-4-yl)acetamide;
2-(biphenyl-4-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)heptanamide;
N-(4-hydroxy-2-(1H-pyrazol-1-yl)pyrimidin-5-yl)-3-phenylpropanamide;
N-(4-hydroxy-2-(1H-pyrazol-1-yl)pyrimidin-5-yl)-4-phenylbutanamide;
N-(4-hydroxy-2-(1H-pyrazol-1-yl)pyrimidin-5-yl)cyclohexanecarboxamide;
tert-butyl 4-(4-hydroxy-2-(1H-pyrazol-1-yl)pyrimidin-5-ylcarbamoyl)piperidine-1-carboxylate;
2-cyclohexyl-N-(4-hydroxy-2-(1H-pyrazo101.01-1-yl)pyrimidin-5-yl)acetamide;
tert-butyl 3-(4-hydroxy-2-(1H-pyrazol-1-yl)pyrimidin-5-ylcarbamoyl)piperidine-1-carboxylate;
tert-butyl 4-((4-hydroxy-2-(1H-pyrazol-1-yl)pyrimidin-5-ylcarbamoyl)methyl)piperidine-1-carboxylate;
tert-butyl 3-(4-hydroxy-2-(1H-pyrazol-1-yl)pyrimidin-5-ylcarbamoyl)pyrrolidine-1-carboxylate;
1,2,3,4-tetrahydro-N-(4-hydroxy-2-(1H-pyrazol-1-yl)pyrimidin-5-yl)naphthalene-1-carboxamide;
2,3-dihydro-N-(4-hydroxy-2-(1H-pyrazol-1-yl)pyrimidin-5-yl)-1H-indene-1-carboxamide;
1,2,3,4-tetrahydro-N-(4-hydroxy-2-(1H-pyrazol-1-yl)pyrimidin-5-yl)naphthalene-2-carboxamide;
2,3-dihydro-N-(4-hydroxy-2-(1H-pyrazol-1-yl)pyrimidin-5-yl)-1H-indene-2-carboxamide;
4-chloro-N-[4-hydroxy-2-(1H-pyrazol-1-yl)pyrimidin-5-yl]benzenesulfonamide;
1-(4-chlorophenyl)-N-[4-hydroxy-2-(1H-pyrazol-1-yl)pyrimidin-5-yl]methanesulfonamide;
3-chloro-N-[4-hydroxy-2-(1H-pyrazol-1-yl)pyrimidin-5-yl]benzenesulfonamide;
N-[4-hydroxy-2-(1H-pyrazol-1-yl)pyrimidin-5-yl]-1-[4-(trifluoromethyl)phenyl]methanesulfonamide;
1-(4-hydroxy-2-(1H-pyrazol-1-yl)pyrimidin-5-yl)-3-phenylurea;
1-benzyl-3-(4-hydroxy-2-(1H-pyrazol-1-yl)pyrimidin-5-yl)urea;
1-(4-hydroxy-2-(1H-pyrazol-1-yl)pyrimidin-5-yl)-3-(1-phenylethyl)urea;
1-cyclohexyl-3-(4-hydroxy-2-(1H-pyrazol-1-yl)pyrimidin-5-yl)urea;
1-cyclopentyl-3-(4-hydroxy-2-(1H-pyrazol-1-yl)pyrimidin-5-yl)urea;

tert-butyl-3-(4-hydroxy-2-(1H-pyrazol-1-yl)pyrimidin-5-yl)urea;
3-(4-hydroxy-2-(1H-pyrazol-1-yl)pyrimidin-5-yl)-1,1-diphenylurea;
3-(4-hydroxy-2-(1H-pyrazol-1-yl)pyrimidin-5-yl)-1-isopropyl-1-phenylurea;
phenyl 4-hydroxy-2-(1H-pyrazol-1-yl)pyrimidin-5-yl carbamate;
cyclohexyl 4-hydroxy-2-(1H-pyrazol-1-yl)pyrimidin-5-yl carbamate;
cyclopentyl 4-hydroxy-2-(1H-pyrazol-1-yl)pyrimidin-5-yl carbamate;
tert-butyl 4-hydroxy-2-(1H-pyrazol-1-yl)pyrimidin-5-yl carbamate;
butyl 4-hydroxy-2-(1H-pyrazol-1-yl)pyrimidin-5-yl carbamate;
4-methoxyphenyl 4-hydroxy-2-(1H-pyrazol-1-yl)pyrimidin-5-yl carbamate;
3,3-dimethylbutyl 4-hydroxy-2-(1H-pyrazol-1-yl)pyrimidin-5-yl carbamate;
phenethyl 4-hydroxy-2-(1H-pyrazol-1-yl)pyrimidin-5-yl carbamate;
biphenyl-4-yl 4-hydroxy-2-(1H-pyrazol-1-yl)pyrimidin-5-yl carbamate;
naphthalen-2-yl 4-hydroxy-2-(1H-pyrazol-1-yl)pyrimidin-5-yl carbamate;
1-benzhydryl-3-(4-hydroxy-2-(1H-pyrazol-1-yl)pyrimidin-5-yl)thiourea;
1-(4-hydroxy-2-(1H-pyrazol-1-yl)pyrimidin-5-yl)-3-(1-phenylethyl)thiourea;
1-(4-hydroxy-2-(1H-pyrazol-1-yl)pyrimidin-5-yl)-3-(2-phenylpropan-2-yl)thiourea;
benzhydryl 4-hydroxy-2-(1H-pyrazol-1-yl)pyrimidine-5-carboxylate;
N-(4-hydroxy-2-(pyridin-2-yl)pyrimidin-5-yl)-2,2-diphenylacetamide;
5-(1-phenyl-1H-pyrazol-4-yl)-2-(1H-pyrazol-1-yl)pyrimidin-4-ol;
5-(1-benzyl-1H-pyrazol-4-yl)-2-(1H-pyrazol-1-yl)pyrimidin-4-ol;
5-phenyl-2-(1H-pyrazol-1-yl)pyrimidin-4-ol;
N-(4-chlorophenyl)-2-(4-hydroxy-2-(1H-pyrazol-1-yl)pyrimidin-5-yl)acetamide;
N-cyclohexyl-2-(4-hydroxy-2-(1H-pyrazol-1-yl)pyrimidin-5-yl)acetamide;
2-(4-hydroxy-2-(1H-pyrazol-1-yl)pyrimidin-5-yl)-N-isopropylacetamide;
4-hydroxy-2-(pyridazin-3-yl)-N-tosylpyrimidine-5-carboxamide;
and pharmaceutically acceptable salts and solvates thereof.

2. A compound selected from:
N-(4-hydroxy-2-(1H-pyrazol-1-yl)pyrimidin-5-yl)-2,2-diphenylacetamide;
2-chloro-N-(4-hydroxy-2-(1H-pyrazol-1-yl)pyrimidin-5-yl)benzamide;
3-chloro-N-(4-hydroxy-2-(1H-pyrazol-1-yl)pyrimidin-5-yl)benzamide;
3-(trifluoromethyl)-N-(4-hydroxy-2-(1H-pyrazol-1-yl)pyrimidin-5-yl)benzamide;
N-(4-hydroxy-2-(1H-pyrazol-1-yl)pyrimidin-5-yl)-2-(naphthalen-3-yl)acetamide;
2-(trifluoromethyl)-N-(4-hydroxy-2-(1H-pyrazol-1-yl)pyrimidin-5-yl)benzamide;
N-[4-hydroxy-2-(1H-pyrazol-1-yl)pyrimidin-5-yl]biphenyl-4-carboxamide;
N-(4-hydroxy-2-(1H-pyrazol-1-yl)pyrimidin-5-yl)-3-phenoxybenzamide;
N-(4-hydroxy-2-(1H-pyrazol-1-yl)pyrimidin-5-yl)-4-phenoxybenzamide;
2-(2-chlorophenyl)-N-(4-hydroxy-2-(1H-pyrazol-1-yl)pyrimidin-5-yl)acetamide;
2-(3-chlorophenyl)-N-(4-hydroxy-2-(1H-pyrazol-1-yl)pyrimidin-5-yl)acetamide;
2-(4-chlorophenyl)-N-(4-hydroxy-2-(1H-pyrazol-1-yl)pyrimidin-5-yl)acetamide;
2-(3-cyanophenyl)-N-(4-hydroxy-2-(1H-pyrazol-1-yl)pyrimidin-5-yl)acetamide;
2-(2-(trifluoromethyl)phenyl)-N-(4-hydroxy-2-(1H-pyrazol-1-yl)pyrimidin-5-yl)acetamide;
2-(3-(trifluoromethyl)phenyl)-N-(4-hydroxy-2-(1H-pyrazol-1-yl)pyrimidin-5-yl)acetamide;
2-(4-(trifluoromethyl)phenyl)-N-(4-hydroxy-2-(1H-pyrazol-1-yl)pyrimidin-5-yl)acetamide;
N-(4-hydroxy-2-(1H-pyrazol-1-yl)pyrimidin-5-yl)-2-(2-methoxyphenyl)acetamide;
N-(4-hydroxy-2-(1H-pyrazol-1-yl)pyrimidin-5-yl)-2-(3-methoxyphenyl)acetamide;
N-(4-hydroxy-2-(1H-pyrazol-1-yl)pyrimidin-5-yl)-2-(4-methoxyphenyl)acetamide;
N-(4-hydroxy-2-(1H-pyrazol-1-yl)pyrimidin-5-yl)-2-phenylpropanamide;
N-(4-hydroxy-2-(1H-pyrazol-1-yl)pyrimidin-5-yl)-2-phenylbutanamide;
N-(4-hydroxy-2-(1H-pyrazol-1-yl)pyrimidin-5-yl)-3-methyl-2-phenylpentanamide;
N-(4-hydroxy-2-(1H-pyrazol-1-yl)pyrimidin-5-yl)-2-methyl-2-phenylpropanamide;
N-(4-hydroxy-2-(1H-pyrazol-1-yl)pyrimidin-5-yl)-2-(naphthalen-1-yl)acetamide;
2-(benzo[d][1,3]dioxol-5-yl)-N-(4-hydroxy-2-(1H-pyrazol-1-yl)pyrimidin-5-yl)acetamide;
2-(biphenyl-4-yl)-N-(4-hydroxy-2-(1H-pyrazol-1-yl)pyrimidin-5-yl)acetamide;
N-(4-hydroxy-2-(1H-pyrazol-1-yl)pyrimidin-5-yl)heptanamide;
N-(4-hydroxy-2-(1H-pyrazol-1-yl)pyrimidin-5-yl)-4-phenylbutanamide;
tert-butyl4-(4-hydroxy-2-(1H-pyrazol-1-yl)pyrimidin-5-ylcarbamoyl)piperidine-1-carboxylate;
2-cyclohexyl-N-(4-hydroxy-2-(1H-pyrazo101.01-1-yl)pyrimidin-5-yl)acetamide;
1,2,3,4-tetrahydro-N-(4-hydroxy-2-(1H-pyrazol-1-yl)pyrimidin-5-yl)naphthalene-1-carboxamide;
2,3-dihydro-N-(4-hydroxy-2-(1H-pyrazol-1-yl)pyrimidin-5-yl)-1H-indene-1-carboxamide;
2,3-dihydro-N-(4-hydroxy-2-(1H-pyrazol-1-yl)pyrimidin-5-yl)-1H-indene-2-carboxamide;
1-benzyl-3-(4-hydroxy-2-(1H-pyrazol-1-yl)pyrimidin-5-yl)urea;
1-(4-hydroxy-2-(1H-pyrazol-1-yl)pyrimidin-5-yl)-3-(1-phenylethyl)urea;
3-(4-hydroxy-2-(1H-pyrazol-1-yl)pyrimidin-5-yl)-1,1-diphenylurea;
1-benzhydryl-3-(4-hydroxy-2-(1H-pyrazol-1-yl)pyrimidin-5-yl)thiourea;
1-(4-hydroxy-2-(1H-pyrazol-1-yl)pyrimidin-5-yl)-3-(1-phenylethyl)thiourea;
and pharmaceutically acceptable salts and solvates thereof.

* * * * *

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: PHD2 Substrate

<400> SEQUENCE: 1

Asp Leu Asp Leu Glu Met Leu Ala Pro Tyr Ile Pro Met Asp Asp
 1               5                  10                  15

Phe Gln Leu
```